(12) United States Patent
Inoue et al.

(10) Patent No.: US 8,921,549 B2
(45) Date of Patent: Dec. 30, 2014

(54) ORGANOMETALLIC COMPLEX, LIGHT-EMITTING ELEMENT, LIGHT-EMITTING DEVICE, ELECTRONIC DEVICE, AND LIGHTING DEVICE

(71) Applicant: Semiconductor Energy Laboratory Co., Ltd., Kanagawa-ken (JP)

(72) Inventors: Hideko Inoue, Kanagawa (JP); Tomoya Yamaguchi, Kanagawa (JP); Hiromi Seo, Kanagawa (JP); Satoshi Seo, Kanagawa (JP)

(73) Assignee: Semiconductor Energy Laboratory Co., Ltd. (JP)

(*) Notice: Subject to any disclaimer, the term of this patent is extended or adjusted under 35 U.S.C. 154(b) by 0 days.

(21) Appl. No.: 13/905,783

(22) Filed: May 30, 2013

(65) Prior Publication Data
US 2013/0324721 A1  Dec. 5, 2013

(30) Foreign Application Priority Data
Jun. 1, 2012  (JP) ................................. 2012-126045

(51) Int. Cl.
H01L 51/00  (2006.01)
(52) U.S. Cl.
CPC ................................. H01L 51/0071 (2013.01)
USPC ........................................................ 544/250
(58) Field of Classification Search
CPC .................................................... H01L 51/0071
USPC ....................................................... 544/250
See application file for complete search history.

(56) References Cited

U.S. PATENT DOCUMENTS

| | | | |
|---|---|---|---|
| 6,097,147 A | 8/2000 | Baldo et al. |
| 6,803,720 B2 | 10/2004 | Kwong et al. |
| 6,830,828 B2 | 12/2004 | Thompson et al. |
| 6,902,830 B2 | 6/2005 | Thompson et al. |
| 6,953,628 B2 | 10/2005 | Kamatani et al. |
| 7,001,536 B2 | 2/2006 | Thompson et al. |
| 7,220,495 B2 | 5/2007 | Tsuboyama et al. |
| 7,291,406 B2 | 11/2007 | Thompson et al. |
| 7,537,844 B2 | 5/2009 | Thompson et al. |
| 7,589,203 B2 | 9/2009 | Stossel et al. |
| 7,883,787 B2 | 2/2011 | Thompson et al. |
| 7,955,716 B2 | 6/2011 | Nomura et al. |
| 7,960,038 B2 | 6/2011 | Ohsawa et al. |
| 7,993,494 B2 | 8/2011 | Inoue et al. |
| 8,084,145 B2 | 12/2011 | Inoue et al. |
| 8,164,090 B2 | 4/2012 | Iwasaki et al. |
| 2002/0063516 A1 | 5/2002 | Tsuboyama et al. |
| 2005/0221123 A1 | 10/2005 | Inoue et al. |
| 2006/0127696 A1 | 6/2006 | Stossel et al. |
| 2007/0128466 A1 | 6/2007 | Nomura et al. |
| 2007/0129545 A1 | 6/2007 | Inoue et al. |
| 2007/0244320 A1 | 10/2007 | Inoue et al. |
| 2008/0149923 A1 | 6/2008 | Ohsawa et al. |
| 2008/0233432 A1 | 9/2008 | Inoue et al. |
| 2008/0286604 A1 | 11/2008 | Inoue et al. |
| 2008/0305361 A1 | 12/2008 | Inoue et al. |
| 2008/0312437 A1 | 12/2008 | Inoue et al. |
| 2009/0015143 A1 | 1/2009 | Inoue et al. |
| 2009/0033209 A1 | 2/2009 | Seo et al. |
| 2009/0039776 A1 | 2/2009 | Yamada et al. |
| 2010/0105902 A1 | 4/2010 | Inoue et al. |
| 2010/0145044 A1 | 6/2010 | Inoue et al. |
| 2010/0181905 A1 | 7/2010 | Inoue et al. |
| 2010/0219407 A1 | 9/2010 | Kamatani et al. |
| 2011/0082296 A1 | 4/2011 | Inoue et al. |
| 2011/0112296 A1 | 5/2011 | Thompson et al. |
| 2011/0187265 A1 | 8/2011 | De Cola et al. |
| 2011/0210316 A1 | 9/2011 | Kadoma et al. |
| 2011/0245495 A1 | 10/2011 | Inoue et al. |
| 2011/0309345 A1 | 12/2011 | Balaganesan et al. |
| 2012/0061707 A1 | 3/2012 | Seo et al. |
| 2012/0098417 A1 | 4/2012 | Inoue et al. |
| 2012/0104373 A1 | 5/2012 | Inoue et al. |
| 2012/0193613 A1 | 8/2012 | Kadoma et al. |
| 2012/0197020 A1 | 8/2012 | Osaka et al. |

(Continued)

FOREIGN PATENT DOCUMENTS

| | | | |
|---|---|---|---|
| JP | 2007284432 | * | 1/2007 |
| JP | 2007-284432 | | 11/2007 |

OTHER PUBLICATIONS

Accession No. (AN): 17126600, Basic Pref. RN (BPR):91155-27-0, CAS Reg. No. (RN):91155-27-0 Lin. Struct. Formula (LSF): Co(C10H5ON2(NHNH2))C12, Molec. Formula (MF): C10 H8 Cl2 Co N4 O Formula Weight (FW): 330.099, Entry Date (DED): Oct. 17, 2008.*

Accession No. (AN): 17126900, Basic Pref. RN (BPR): 91155-30-5, CAS Reg. No. (RN): 91155-30-5 Lin. Struct. Formula (LSF): Hg(C10H5ON2(NHNH2))C12, Molec. Formula (MF): C10 H8 Cl2 Hg N4 O Formula Weight (FW): 471.696, Entry Date (DED): Oct. 17, 2008.*

(Continued)

*Primary Examiner* — Erich A Leeser
(74) *Attorney, Agent, or Firm* — Husch Blackwell LLP

(57) ABSTRACT

Provided are a light-emitting element including a novel organometallic complex as an emission center, the organometallic complex, a light-emitting device, an electronic device, and a lighting device each using the light-emitting element. One embodiment of the present invention is a light-emitting element including, as an emission center, an organometallic complex in which a benzofuropyrimidine derivative is coordinated to a metal. In particular, another embodiment is a light-emitting element including, as an emission center, an organometallic complex in which a benzofuropyrimidine derivative having an aryl group at the 4-position is coordinated to a metal. Another embodiment is a light-emitting element including, as an emission center, an organometallic complex in which nitrogen at the 3-position of a benzofuropyrimidine derivative having an aryl group at the 4-position is coordinated to a metal and the aryl group is bonded to the metal.

21 Claims, 21 Drawing Sheets

(56) References Cited

U.S. PATENT DOCUMENTS

| | | |
|---|---|---|
| 2012/0205632 A1 | 8/2012 | Shitagaki et al. |
| 2012/0205687 A1 | 8/2012 | Yamazaki et al. |
| 2012/0206035 A1 | 8/2012 | Shitagaki et al. |
| 2012/0208999 A1 | 8/2012 | Konno |
| 2012/0217487 A1 | 8/2012 | Yamazaki et al. |
| 2012/0242219 A1 | 9/2012 | Seo et al. |
| 2012/0248421 A1 | 10/2012 | Yamazaki et al. |
| 2012/0256535 A1 | 10/2012 | Seo et al. |
| 2012/0264936 A1 | 10/2012 | Inoue et al. |
| 2012/0274201 A1 | 11/2012 | Seo et al. |
| 2012/0277427 A1 | 11/2012 | Inoue et al. |
| 2013/0165653 A1 | 6/2013 | Inoue et al. |

OTHER PUBLICATIONS

Accession No. (AN): 18070774, Chemical Name (CN): (4-methoxybenzofuro<3,2-d>pyrimidino)cadmium(II) chloride, Lin. Struct. Formula (LSF): $Cd(C_6H_4OC_4HN_2OCH_3)Cl_2$, Molec. Formula (MF): $C_{11} H_8 Cd Cl_2 N_2 O_2$ Formula Weight (FW): 383.513, Entry Date (DED): Oct. 22, 2008.*

Accession No. (AN): 18070840, Chemical Name (CN): (4-ethoxybenzofuro<3,2-d>pyrimidino)zinc(II) chloride Lin. Struct. Formula (LSF): $Zn(C_6H_4OC_4HN_2OC_2H_5)Cl_2$, Molec. Formula (MF): $C_{12} H_{10} Cl_2 N_2 O_2 Zn$ Formula Weight (FW): 350.52, Entry Date (DED): Oct. 22, 2008.*

* cited by examiner

- - Fluorescence spectrum of the first organic compound 213 or second organic compound 214
- - - Phosphorescence spectrum of the first organic compound 213 or second organic compound 214
— Absorption spectrum of the third organic compound 215
— Light-emitting spectrum of the exciplex

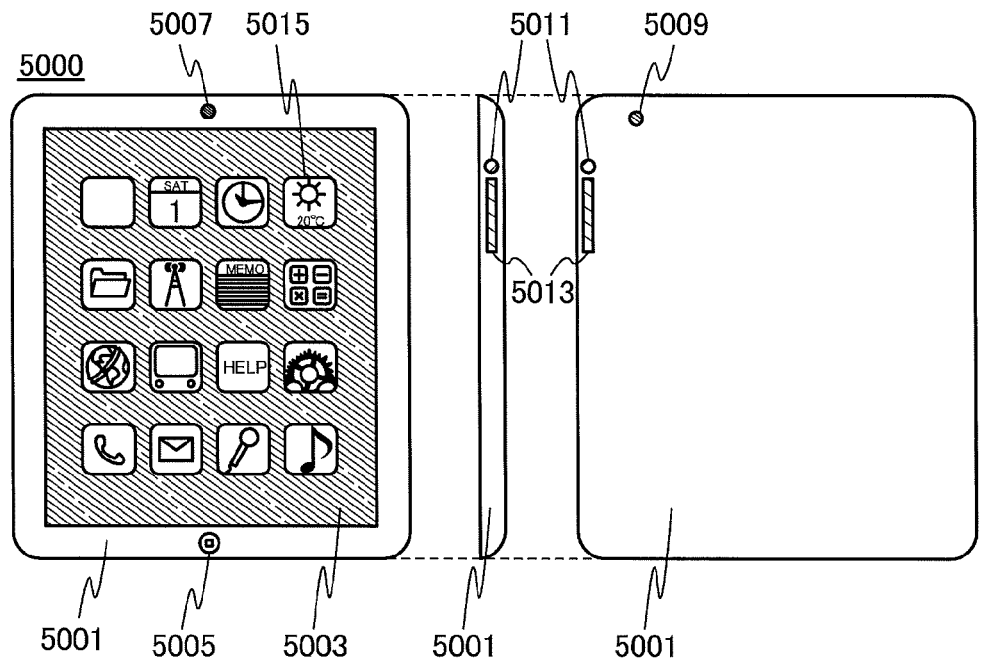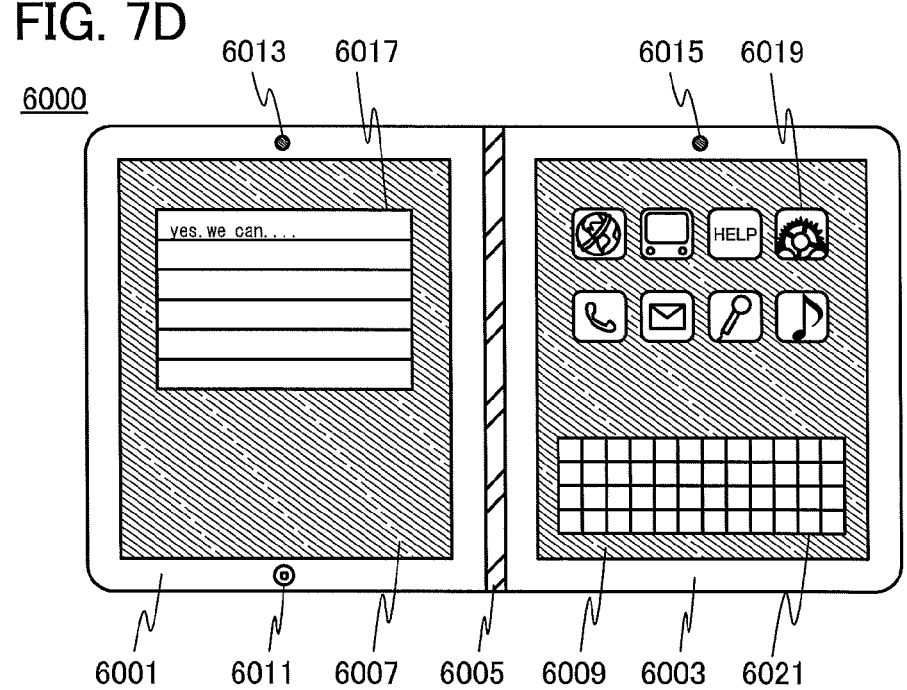

ORGANOMETALLIC COMPLEX, LIGHT-EMITTING ELEMENT, LIGHT-EMITTING DEVICE, ELECTRONIC DEVICE, AND LIGHTING DEVICE

BACKGROUND OF THE INVENTION

1. Field of the Invention

The present invention relates to a light-emitting element including, as an emission center, an organometallic complex capable of converting a triplet excited state into light emission. The present invention also relates to the organometallic complex. In addition, the present invention relates to a light-emitting device, an electronic device, and a lighting device each using the light-emitting element.

2. Description of the Related Art

In recent years, a light-emitting element using a light-emitting organic compound or an inorganic compound as a light-emitting material has been actively developed. In particular, a light-emitting element called an EL (electroluminescence) element has attracted attention as a next-generation flat panel display element because it has a simple structure in which a light-emitting layer containing a light-emitting material is provided between electrodes, and characteristics such as feasibility of being thinner and more lightweight and responsive to input signals and capability of driving with direct current at a low voltage. In addition, a display using such a light-emitting element has a feature that it is excellent in contrast and image quality, and has a wide viewing angle. Further, since such a light-emitting element is a plane light source, the light-emitting element is considered applicable to a light source such as a backlight of a liquid crystal display and lighting.

In the case where the light-emitting substance is an organic compound having a light-emitting property, the emission mechanism of the light-emitting element is a carrier-injection type. That is, by applying a voltage with a light-emitting layer interposed between electrodes, electrons and holes injected from electrodes recombine to make the light-emitting substance excited, and light is emitted when the excited state returns to a ground state. There are two types of the excited states which are possible: a singlet excited state (S*) and a triplet excited state (T*). In addition, the statistical generation ratio thereof in a light-emitting element is considered to be an S*-to-T* ratio of 1:3.

In general, the ground state of a light-emitting organic compound is a singlet state. Light emission from a singlet excited state (S*) is referred to as fluorescence where electron transition occurs between the same multiplicities. In contrast, light emission from a triplet excited state (T*) is referred to as phosphorescence where electron transition occurs between different multiplicities. Here, in a compound emitting fluorescence (hereinafter referred to as fluorescent compound), in general, phosphorescence is not observed at room temperature, and only fluorescence is observed. Accordingly, the internal quantum efficiency (the ratio of generated photons to injected carriers) in a light-emitting element using a fluorescent compound is assumed to have a theoretical limit of 25% based on the S*-to-T* ratio of 1:3.

The use of a phosphorescent compound can increase the internal quantum efficiency to 100% in theory. In other words, emission efficiency can be four times as much as that of the fluorescence compound. Therefore, the light-emitting element using a phosphorescent compound has been actively developed in recent years in order to achieve a highly efficient light-emitting element.

As a phosphorescent compound, an organometallic complex including iridium or the like as a central metal has particularly attracted attention because of its high phosphorescence quantum efficiency. An example of an organometallic complex exhibiting red light emission is an organometallic complex in which a pyrazine derivative is ortho-metalated with an ion of a Group 9 or Group 10 metal (see Patent Document 1, for example).

REFERENCE

Patent Document 1: Japanese Published Patent Application No. 2007-284432

SUMMARY OF THE INVENTION

As reported in Patent Document 1, although light-emitting elements using organometallic complexes have been developed, there is room for improvement in terms of emission efficiency, reliability, light-emitting characteristics, synthesis yield, cost, or the like, and further development is required for obtaining more excellent light-emitting elements.

In view of the above problems, an object of one embodiment of the present invention is to provide a light-emitting element including a novel organometallic complex as an emission center. Another object is to provide the organometallic complex. Another object is to provide a light-emitting device, an electronic device, and a lighting device each using the light-emitting element.

The present inventors have found that an organometallic complex in which a benzofuropyrimidine derivative is coordinated to a metal emits phosphorescence. Further, the present inventors have found that a light-emitting element including the organometallic complex between a pair of electrodes emits phosphorescence by application of a voltage and has high reliability.

Thus, one embodiment of the present invention is a light-emitting element including, as an emission center, an organometallic complex in which a benzofuropyrimidine derivative is coordinated to a metal. In particular, a preferable embodiment is a light-emitting element including, as an emission center, an organometallic complex in which a benzofuropyrimidine derivative having an aryl group at the 4-position is coordinated to a metal. Another preferable embodiment is a light-emitting element including, as an emission center, an organometallic complex in which nitrogen at the 3-position of a benzofuropyrimidine derivative having an aryl group at the 4-position is coordinated to a metal and the aryl group is bonded to the metal.

In each of the above structures, the metal is preferably a Group 9 element or a Group 10 element, more preferably iridium.

Another embodiment of the present invention is an organometallic complex including a structure represented by a general formula (G1). An organometallic complex including the structure represented by the general formula (G1) can emit phosphorescence and thus can be advantageously applied to a light-emitting layer of a light-emitting element.

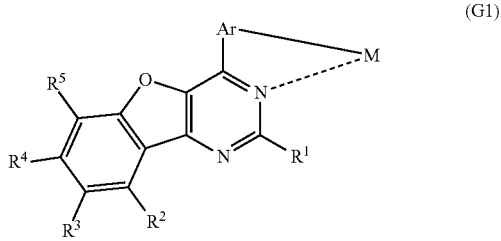

(G1)

In particular, a phosphorescent organometallic complex which includes the structure represented by the general formula (G1) and in which the lowest triplet excited state is formed in the structure is preferable because, in the organometallic complex, a skeleton (another ligand) other than that represented by the general formula (G1) does not cause quenching of the lowest triplet excited state, which contributes to light emission, and therefore phosphorescence can be efficiently emitted. To achieve such a mode, another skeleton (ligand) which is included in the phosphorescent organometallic complex is selected such that the lowest triplet excitation energy of the structure is equal to or lower than the lowest triplet excitation energy of the skeleton (ligand), for example. With such a structure, regardless of what a skeleton (ligand) other than the structure is, the lowest triplet excited state is formed by the structure at last, so that phosphorescence originating from the structure is obtained. Therefore, phosphorescence can be highly efficiently obtained. A typical example is vinyl polymer having the structure as a side chain.

Another embodiment of the present invention is an organometallic complex represented by a general formula (G2).

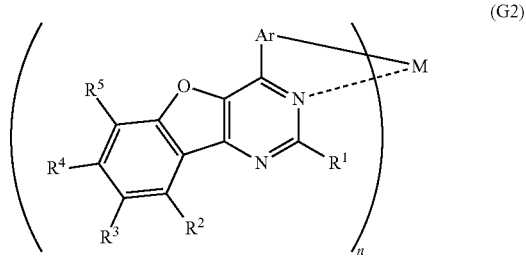

(G2)

A further embodiment of the present invention is an organometallic complex represented by a general formula (G3).

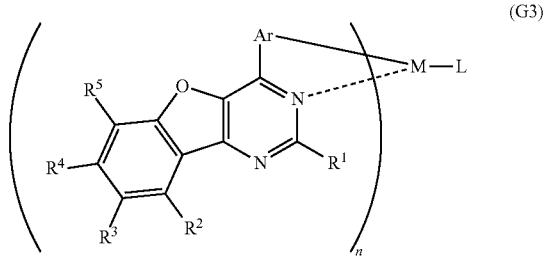

(G3)

In each of the general formulae (G1), (G2), and (G3), $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms, and M represents a Group 9 element or a Group 10 element.

In addition, in the general formula (G2), n is 3 when M is a Group 9 element, and n is 2 when M is a Group 10 element.

In the general formula (G3), n is 2 when M is a Group 9 element, and n is 1 when the central metal M is a Group 10 element. Further, L represents a monoanionic ligand.

In each of the general formulae (G1), (G2), and (G3), M represents a Group 9 element or a Group 10 element; the Group 9 element is preferably iridium and the Group 10 element is preferably platinum. In terms of a heavy atom effect, a heavy metal is preferably used as the central metal of the organometallic complex in order to more efficiently emit phosphorescence.

Note that when M is iridium, the spin-orbit interaction is increased. In addition, since M and a ligand have metal-carbon bonding, charge is likely to be transferred to a benzofuropyrimidine derivative which is the ligand (this transfer is also called triplet metal to ligand charge transfer (triplet MLCT)). As a result, a forbidden transition such as phosphorescence is likely to occur and the triplet excitation lifetime decreases, so that there is an effect of increasing the emission efficiency of the phosphorescent organometallic complex, which is preferable.

Another embodiment of the present invention is a light-emitting element containing any organometallic complex described above. In particular, any organometallic complex described above is preferably contained in a light-emitting layer.

Further, one embodiment of the present invention includes, in its category, a light-emitting device including the above light-emitting element, and an electronic device and a lighting device each including the light-emitting device. Note that the light-emitting device in this specification includes, in its category, an image display device, a light-emitting device, and a light source (e.g., a lighting device). In addition, the light-emitting device includes, in its category, all of a module in which a connector such as a flexible printed circuit (FPC), a tape automated bonding (TAB) tape or a tape carrier package (TCP) is connected to a light-emitting device, a module in which a printed wiring board is provided on the tip of a TAB tape or a TCP, and a module in which an integrated circuit (IC) is directly mounted on a light-emitting element by a chip on glass (COG) method.

According to one embodiment of the present invention, a light-emitting element including a novel organometallic complex as an emission center can be provided. The organometallic complex can also be provided.

According to another embodiment of the present invention, a light-emitting device, an electronic device, and a lighting device each using the above light-emitting element can be provided.

BRIEF DESCRIPTION OF THE DRAWINGS

In the accompanying drawings:

FIGS. 7A to 7D illustrate an electronic device according to one embodiment of the present invention;

DETAILED DESCRIPTION OF THE INVENTION

Figure 1:
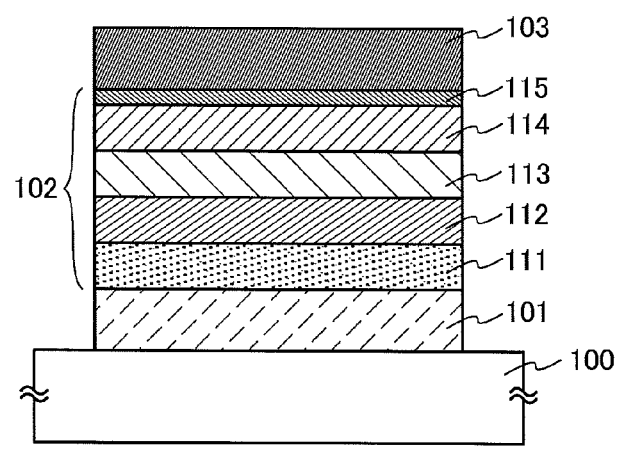
FIG. 1 illustrates a light-emitting element according to one embodiment of the present invention.

Embodiments of the invention will now be described with reference to drawings in detail. Note that the invention is not limited to the following description, and it will be easily understood by those skilled in the art that various changes and modifications can be made without departing from the spirit and scope of the invention. Therefore, the invention should not be construed as being limited to the description in the following embodiments. Note that in the structures of the invention described below, the same portions or portions having similar functions are denoted by the same reference numerals in different drawings, and description of such portions is not repeated.

(Embodiment 1)

A light-emitting element including a novel organometallic complex as an emission center and the organometallic complex are described below.

One embodiment of the present invention is a light-emitting element including, as an emission center, an organometallic complex in which a benzofuropyrimidine derivative is coordinated to a metal. In particular, another embodiment is a light-emitting element including, as an emission center, an organometallic complex in which a benzofuropyrimidine derivative having an aryl group at the 4-position is coordinated to a metal. Another embodiment is a light-emitting element including, as an emission center, an organometallic complex in which nitrogen at the 3-position of a benzofuropyrimidine derivative having an aryl group at the 4-position is coordinated to a metal and the aryl group is bonded to the metal.

In each of the above light-emitting elements, the metal is preferably a Group 9 element or a Group 10 element, more preferably iridium.

Another embodiment of the present invention is an organometallic complex including a structure represented by the general formula (G1), an organometallic complex represented by the general formula (G2), or an organometallic complex represented by the general formula (G3). A phosphorescent organometallic complex which includes the structure represented by the general formula (G1) and in which the lowest triplet excited state is formed in the structure is preferable because, in the organometallic complex, a skeleton (another ligand) other than that represented by the general formula (G1) does not cause quenching of the lowest triplet excited state, which contributes to light emission, and therefore phosphorescence can be efficiently emitted. To achieve such a mode, another skeleton (ligand) which is included in the phosphorescent organometallic complex is selected such that the lowest triplet excitation energy of the structure is equal to or lower than the lowest triplet excitation energy of the skeleton (ligand), for example. With such a structure, regardless of what a skeleton (ligand) other than the structure is, the lowest triplet excited state is formed in the structure at last, so that phosphorescence originating from the structure is obtained. Thus, phosphorescence can be highly efficiently obtained. A typical example is vinyl polymer having the structure as a side chain.

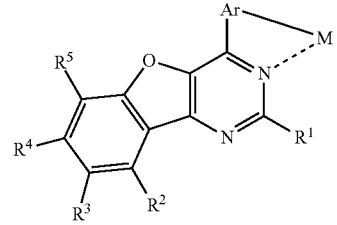

(G1)

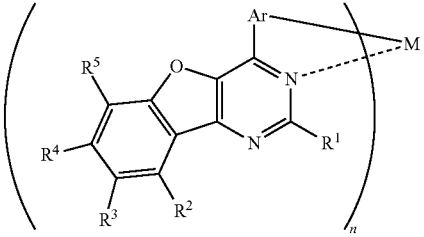

(G2)

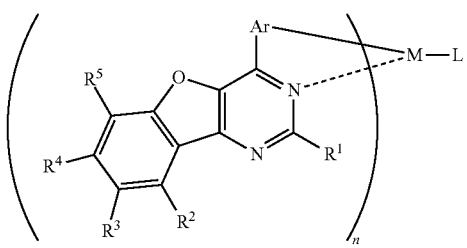
(G3)

In each of the general formulae (G1), (G2), and (G3), $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms, and M represents a Group 9 element or a Group 10 element.

In addition, in the general formula (G2), n is 3 when M is a Group 9 element, and n is 2 when M is a Group 10 element.

In the general formula (G3), n is 2 when M is a Group 9 element, and n is 1 when the central metal M is a Group 10 element. Further, L represents a monoanionic ligand.

In the general formula (G3), the monoanionic ligand is preferably any of a monoanionic bidentate chelate ligand having a beta-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. In particular, the monoanionic ligand is preferably a monoanionic bidentate chelate ligand having a beta-diketone structure because of its stability.

Note that the monoanionic ligand is preferably a ligand represented by any of general formulae (L1) to (L7) below.

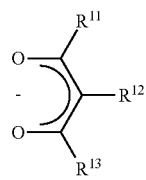
(L1)

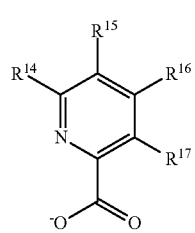
(L2)

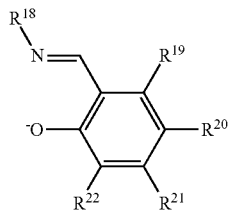
(L3)

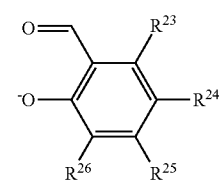
(L4)

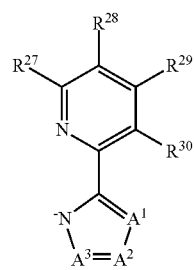
(L5)

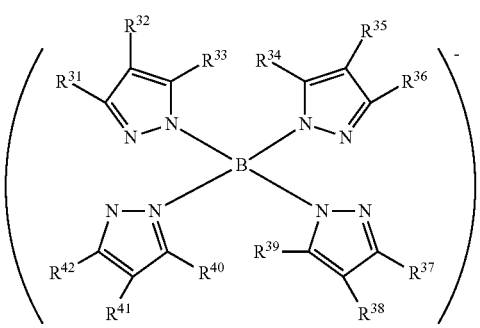
(L6)

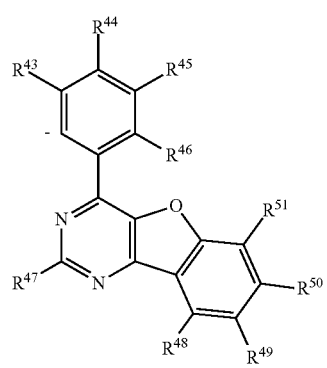
(L7)

In the general formulae (L1) to (L7), $R^{11}$ to $R^{51}$ separately represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms. Further, examples of a substituent that can be used here are an aryl group, an alkyl group, an alkenyl group, an alkynyl group, an alkoxy group, a carbonyl group, a carboxyl group, a hydroxyl group, a mercapto group, a halogen, a sulfonyl group, an amino group, and the like. Further, $A^1$ to $A^3$ separately represent any of nitrogen, $sp^2$ hybridized carbon bonded to hydrogen, and $sp^2$ hybridized carbon bonded to any of an alkyl group having 1 to 6 carbon atoms, a halogen group, a haloalkyl group having 1 to 6 carbon atoms, and a phenyl group.

Note that an organometallic complex including the structure represented by the general formula (G1), the organometallic complex represented by the general formula (G2), and the organometallic complex represented by the general formula (G3) can emit phosphorescence and therefore can be advantageously applied to a light-emitting layer of a light-emitting element. Thus, preferable embodiments of the present invention are an organometallic complex including the structure represented by the general formula (G1), the organometallic complex represented by the general formula (G2), and the organometallic complex represented by the general formula (G3).

In particular, the organometallic complex which includes the structure represented by the general formula (G1) and in which the lowest triplet excited state is formed in the structure is preferable because the organometallic complex can efficiently exhibit phosphorescence. To achieve such a mode, another skeleton (ligand) which is included in the organometallic complex is selected such that the lowest triplet excitation energy of the structure is equal to or lower than the lowest triplet excitation energy of the skeleton (ligand), for example. With such a structure, regardless of what a skeleton (ligand) other than the structure is, the lowest triplet excited state is formed in the structure at last, so that phosphorescence originating from the structure is thus obtained. Thus, phosphorescence can be highly efficiently obtained. A typical example is vinyl polymer having the structure as a side chain.

Here, examples of methods of synthesizing an organometallic complex including the structure represented by the general formula (G1), the organometallic complex represented by the general formula (G2), and the organometallic complex represented by the general formula (G3) are described.

<Method of Synthesizing a 4-Arylbenzofuro[3,2-d]Pyrimidine Derivative Represented by a General Formula (G0)>

A 4-arylbenzofuro[3,2-d]pyrimidine derivative represented by a general formula (G0) below can be synthesized according to a synthesis scheme (a), which is simple as illustrated below.

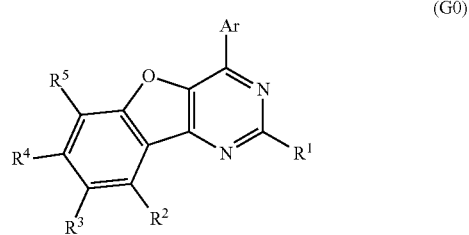

(G0)

In the general formula (G0), $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms.

As shown in the synthesis scheme (a) below, a boronic acid compound of aryl (A1) and a 4-chlorobenzofuro[3,2-d]pyrimidine derivative (A2) react with each other, so that the 4-arylbenzofuro[3,2-d]pyrimidine derivative can be obtained.

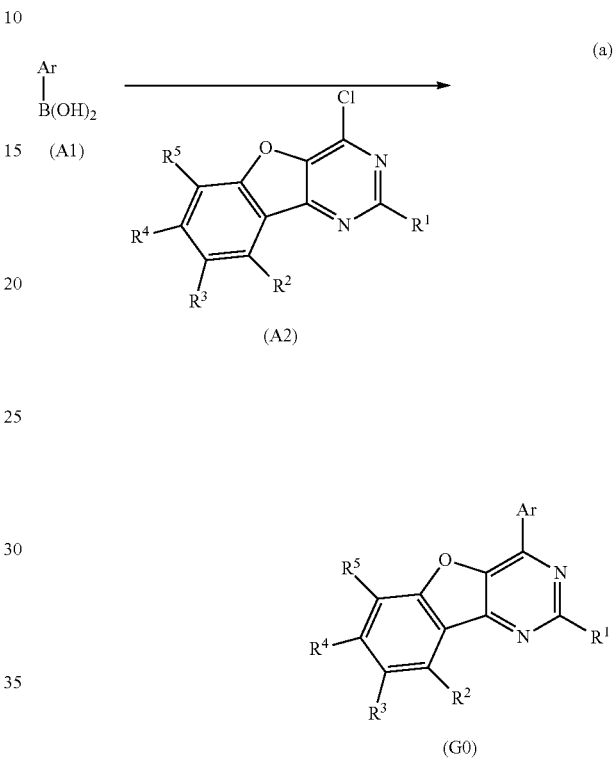

In the synthesis scheme (a), $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms.

Since a wide variety of compounds (A1) and (A2) are commercially available or their synthesis is feasible, a great variety of the 4-arylbenzofuro[3,2-d]pyrimidine derivatives represented by the general formula (G0) can be synthesized. Thus, one of features of the organometallic complex which is one embodiment of the present invention is the abundance of ligand variation.

<Method of Synthesizing the Organometallic Complex of One Embodiment of the Present Invention, Represented by the General Formula (G2)>

The organometallic complex of one embodiment of the invention which is represented by the general formula (G2) can be synthesized according to a synthesis scheme (b) below. Specifically, the 4-arylbenzofuro[3,2-d]pyrimidine derivative represented by the general formula (G0) is mixed with a metal compound of a Group 9 element or a Group 10 element which contains a halogen (e.g., rhodium chloride hydrate, palladium chloride, iridium chloride, iridium bromide, iridium iodide, or potassium tetrachloroplatinate) or with an organometallic compound of a Group 9 element or a Group 10 element (e.g., an acetylacetonate complex or a diethylsulfide complex) and the mixture is then heated, so that the organometallic complex represented by the general formula (G2) can be obtained. This heating process may be performed after the 4-arylbenzofuro[3,2-d]pyrimidine derivative represented by the general formula (G0) and the metal compound of a Group 9 element or a Group 10 element which contains a halogen or the organometallic compound of a Group 9 element or a Group 10 element are dissolved in an alcohol-based solvent (e.g., glycerol, ethylene glycol, 2-methoxyethanol, or 2-ethoxyethanol). There is no particular limitation on a heating means, and an oil bath, a sand bath, or an aluminum block may be used. Alternatively, microwaves can be used as a heating means.

In the synthesis scheme (b), $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms, and M represents a Group 9 element or a Group 10 element. When M is a Group 9 element, n is 3, and when M is a Group 10 element, n is 2.

<Method of Synthesizing the Organometallic Complex of One Embodiment of the Present Invention, Represented by the General Formula (G3)>

The organometallic complex of one embodiment of the invention which is represented by the general formula (G3) can be synthesized as shown in a synthesis scheme (c-1) below. Specifically, the 4-arylbenzofuro[3,2-d]pyrimidine derivative represented by the general formula (G0) and a metal compound of a Group 9 element or a Group 10 element which contains a halogen (e.g., rhodium chloride hydrate, palladium chloride, iridium chloride, iridium bromide, iridium iodide, or potassium tetrachloroplatinate) are heated in an inert gas atmosphere by using no solvent, an alcohol-based solvent (e.g., glycerol, ethylene glycol, 2-methoxyethanol, or 2-ethoxyethanol) alone, or a mixed solvent of water and one or more of the alcohol-based solvents, whereby the dinuclear complex (B), which is one type of an organometallic complex including a halogen-bridged structure and is a novel substance, can be obtained. There is no particular limitation on a heating means, and an oil bath, a sand bath, or an aluminum block may be used. Alternatively, microwaves can be used as a heating means.

(b)

Metal compound of Group 9 element or Group 10 element which contains halogen or +

Organometallic compound of Group 9 element or Group 10 element

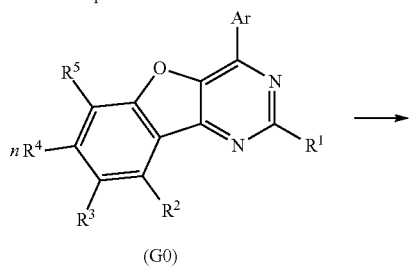

(G0)

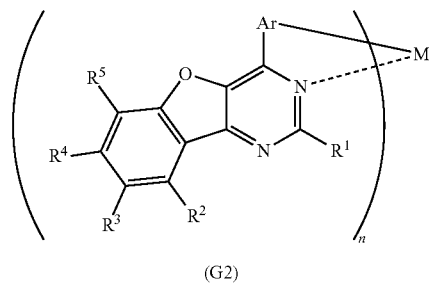

(G2)

(c-1)

Metal compound of Group 9 element or Group 10 element which contains halogen +

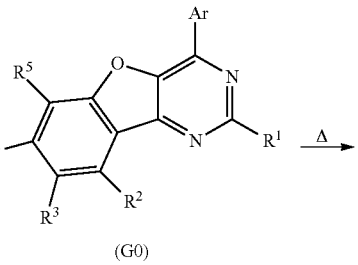

(G0)

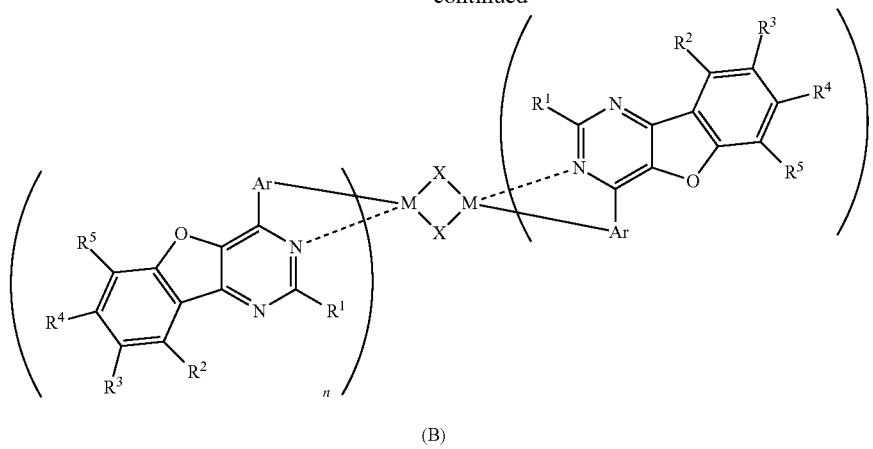

(B)

In the synthesis scheme (c-1), X represents a halogen, $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms, and M represents a Group 9 element or a Group 10 element. Moreover, n is 2 when M is a Group 9 element, and n is 1 when M is a Group 10 element.

Furthermore, as shown in a synthesis scheme (c-2) below, the dinuclear complex (B) obtained in the synthesis scheme (c-1) above is reacted with HL which is a material of a monoanionic ligand in an inert gas atmosphere, whereby a proton of HL is separated and L coordinates to the central metal M. Thus, the organometallic complex of one embodiment of the present invention which is represented by the general formula (G3) can be obtained. There is no particular limitation on a heating means, and an oil bath, a sand bath, or an aluminum block may be used. Alternatively, microwaves can be used as a heating means.

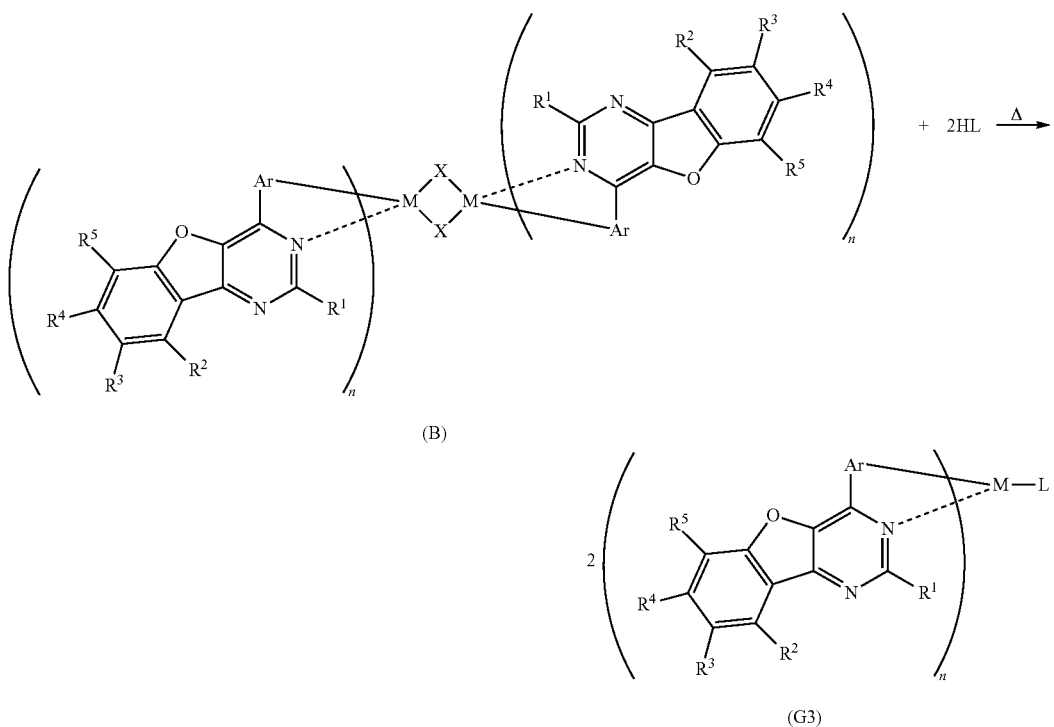

In the synthesis scheme (c-2), L represents a monoanionic ligand, and X represents a halogen. Further, $R^1$ represents hydrogen or a substituted or unsubstituted alkyl group having 1 to 6 carbon atoms, and $R^2$ to $R^5$ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms. Further, Ar represents a substituted or unsubstituted arylene group having 6 to 10 carbon atoms, and M represents a Group 9 element or a Group 10 element. Moreover, n is 2 when M is a Group 9 element, and n is 1 when M is a Group 10 element.

Although examples of the synthesis methods are described above, organometallic complexes according to a disclosed embodiment of the present invention may be synthesized by any other synthesis method.

As specific examples of an organometallic complex including the structure represented by the general formula (G1), the organometallic complex represented by the general formula (G2), and the organometallic complex represented by the general formula (G3), organometallic complexes represented by structural formulae (100) to (141) can be given. Note that the present invention is not limited to the organometallic complexes represented by these structural formulae.

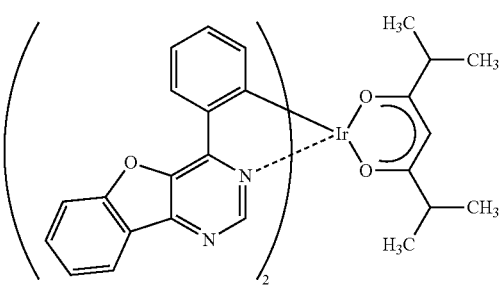

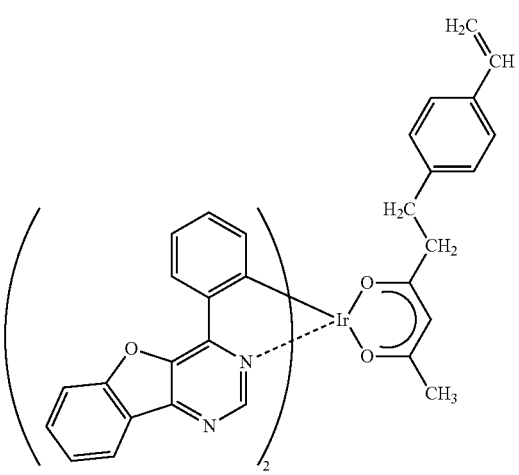

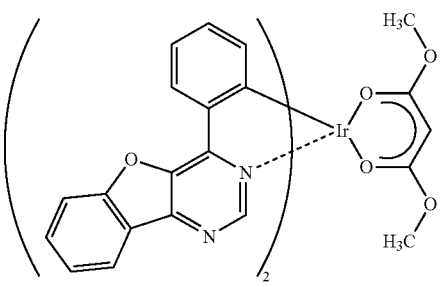

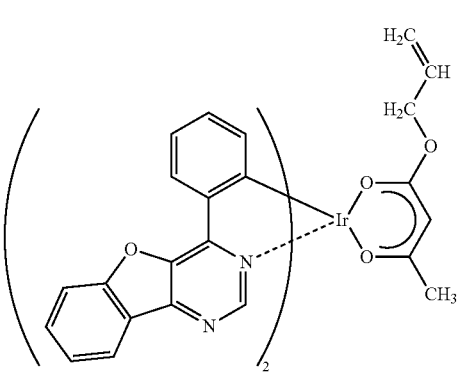

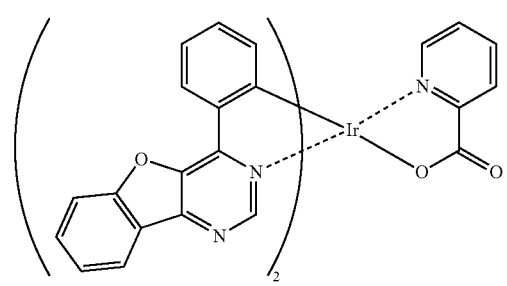
(107)
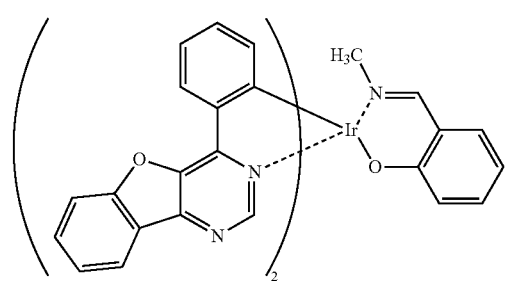
(108)
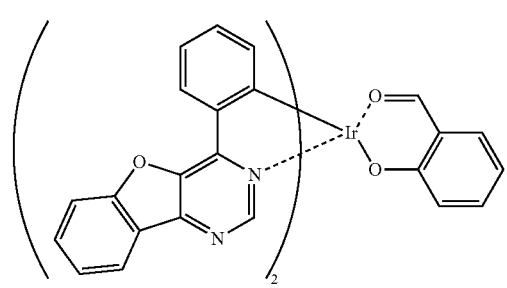
(109)
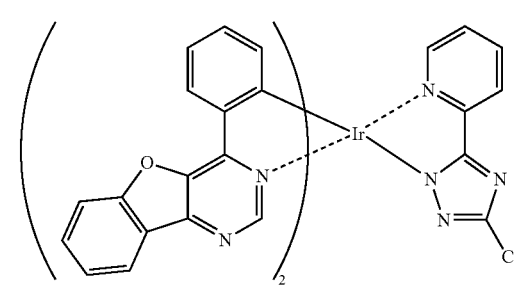
(110)
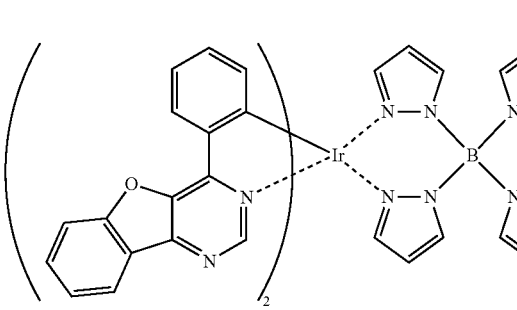
(111)
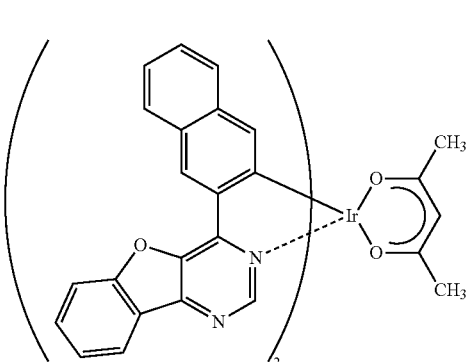
(112)
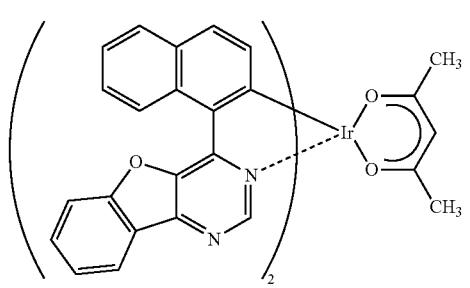
(113)
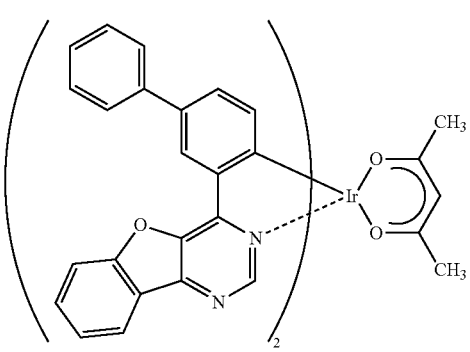
(114)
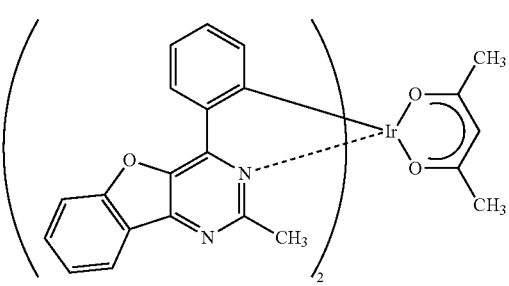
(115)
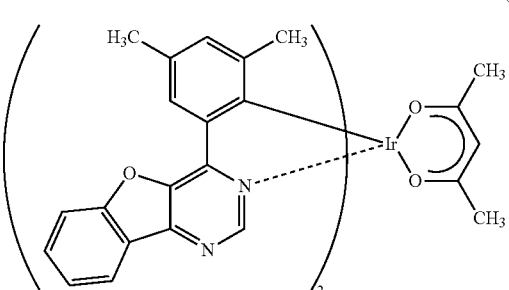
(116)

(117)
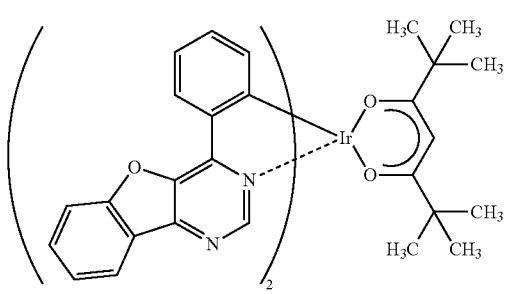
(118)
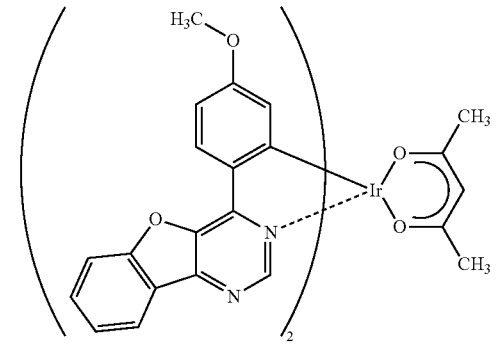
(119)
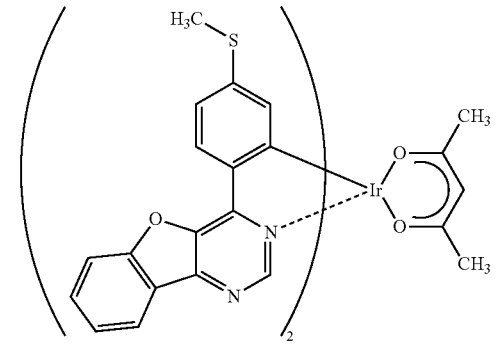
(120)
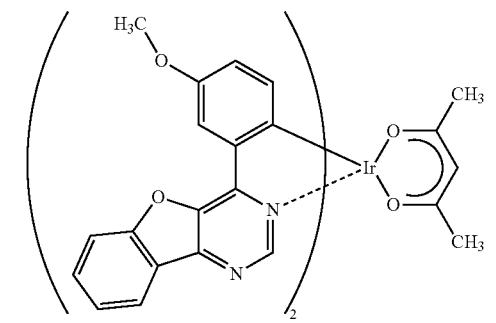
(121)
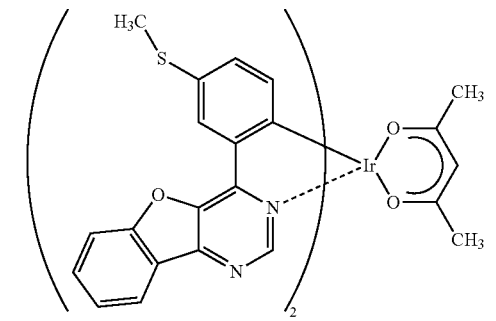
(122)
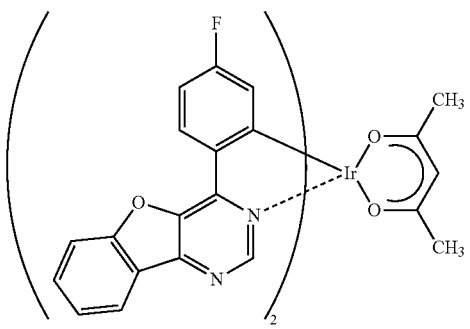
(123)
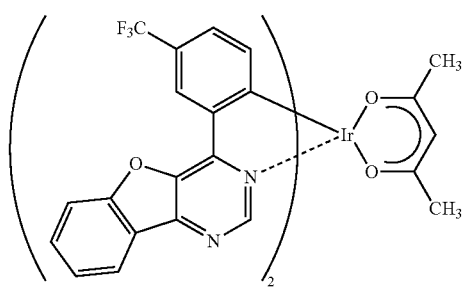
(124)
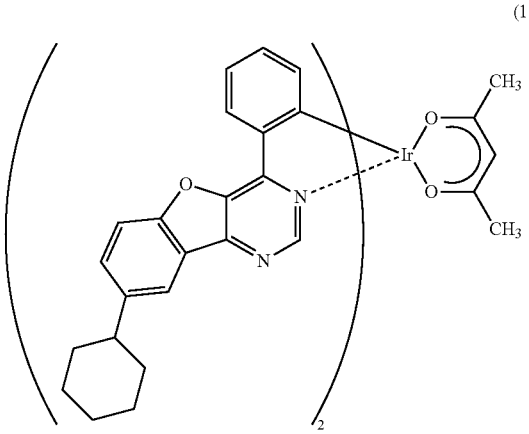
(125)
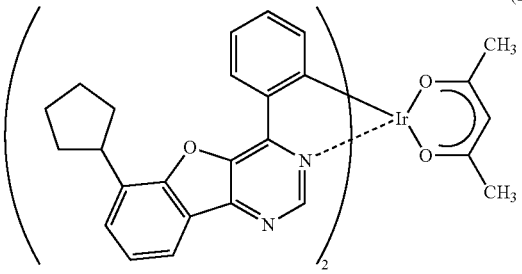
(126)
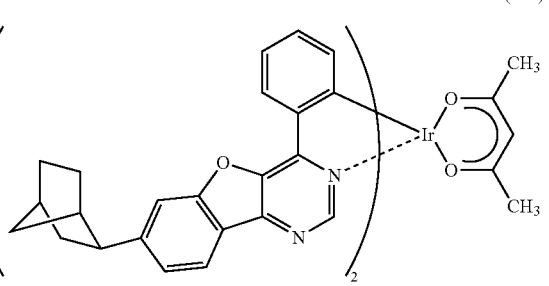

(127)
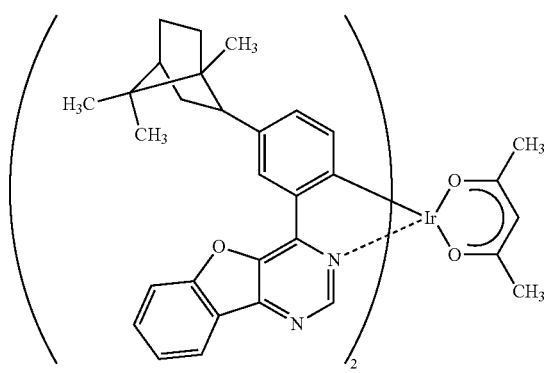
(128)
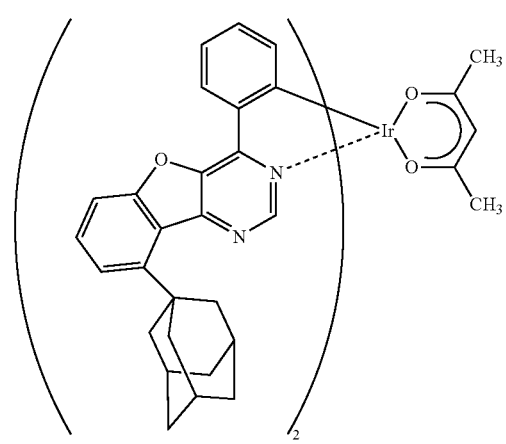
(129)
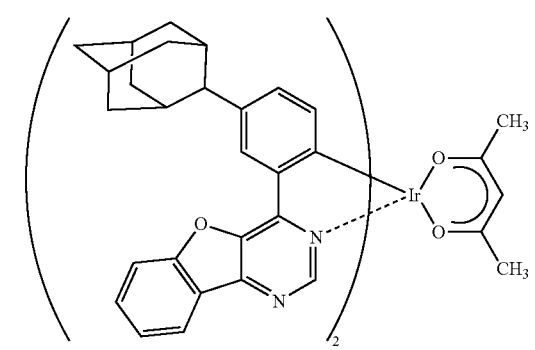
(130)
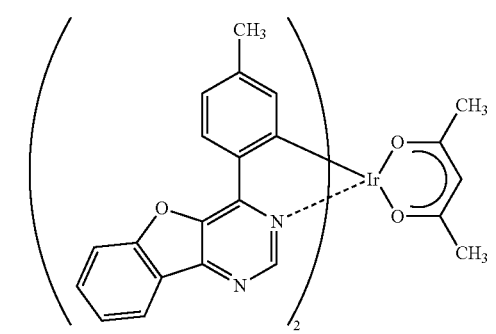
(131)
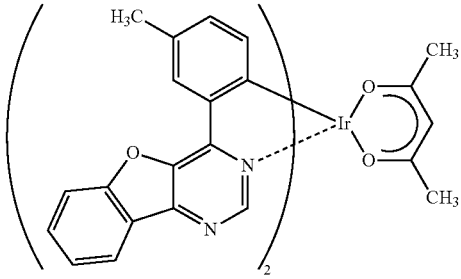
(132)
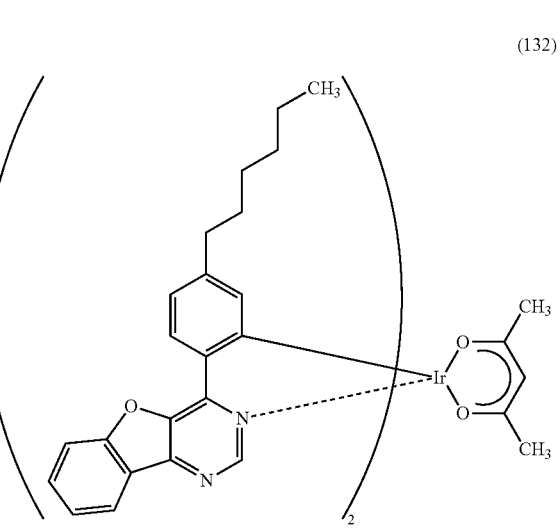
(133)
(134)
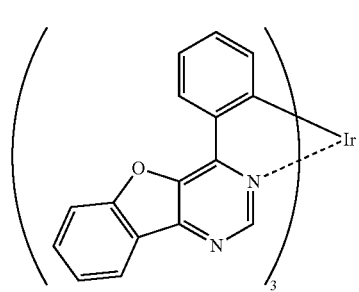

(135) 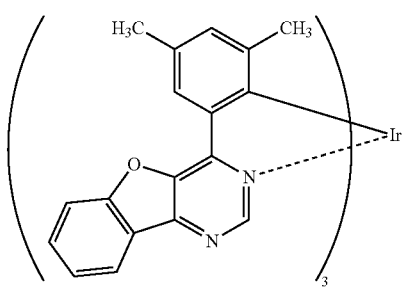

(136) 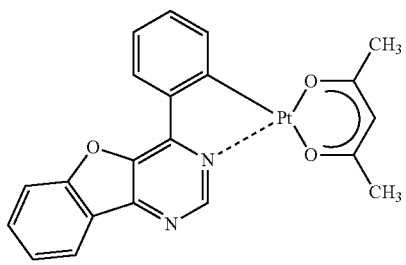

(137) 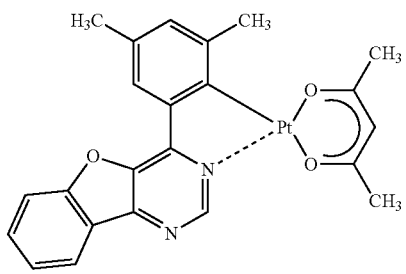

(138) 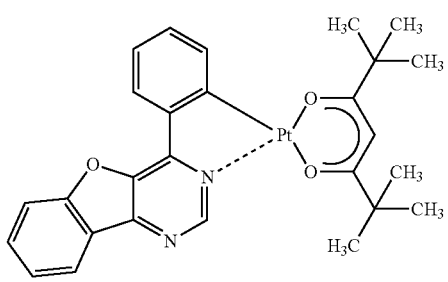

(139) 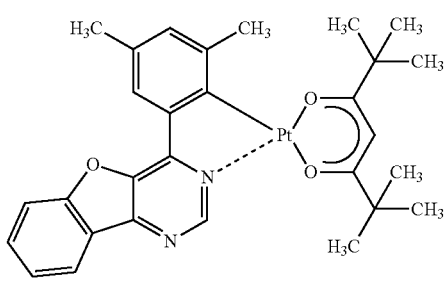

(140) 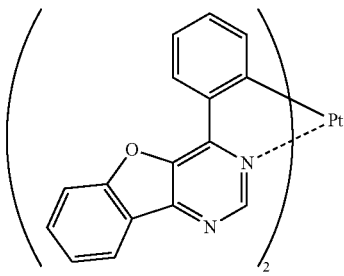

(141) 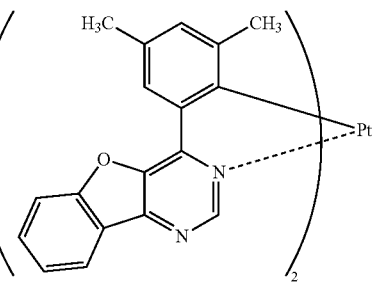

Depending on the type of the ligand, there can be stereoisomers of the organometallic complexes represented by the above structural formulae (100) to (141), and such isomers are included in the category of an organometallic complex of one embodiment of the present invention.

The above-described organometallic complexes each of which is one embodiment of the present invention are novel substances capable of emitting phosphorescence.

This embodiment can be implemented in appropriate combination with any of the other embodiments.

(Embodiment 2)

In this embodiment, an organometallic complex and a light-emitting element including the organometallic complex as an emission center according to one embodiment of the present invention are described with reference to FIG. 1.

In the light-emitting element of this embodiment, an EL layer having at least a light-emitting layer is interposed between a pair of electrodes. The EL layer may also have a plurality of layers in addition to the light-emitting layer. The plurality of layers has a structure in which a layer including a substance having a high carrier-injection property and a layer including a substance having a high carrier-transport property are combined and stacked so that a light-emitting region is formed in a region away from the electrodes, that is, so that carriers recombine in a region away from the electrodes. In this specification, the layer including a substance having a high carrier-injection or -transport property is also referred to as a functional layer which has a function of, for example, injecting or transporting carriers. As the functional layer, a hole-injection layer, a hole-transport layer, an electron-injection layer, an electron-transport layer, or the like can be used.

In the light-emitting element of this embodiment illustrated in FIG. 1, an EL layer 102 having a light-emitting layer 113 is provided between a pair of electrodes, a first electrode 101 and a second electrode 103. The EL layer 102 includes a hole-injection layer 111, a hole-transport layer 112, the light-emitting layer 113, an electron-transport layer 114, and an electron-injection layer 115. The light-emitting element in FIG. 1 includes the first electrode 101 formed over a substrate 100; the hole-injection layer 111, the hole-transport layer 112, the light-emitting layer 113, the electron-transport layer 114, and the electron-injection layer 115 which are stacked over the first electrode 101 in this order; and the second electrode 103 provided over the electron-injection layer 115. Note that, in the light-emitting element described in this embodiment, the first electrode 101 functions as an anode and the second electrode 103 functions as a cathode.

An organometallic complex which is one embodiment of the present invention can be used for the EL layer 102, and specifically, is preferably included in at least any one of the hole-injection layer 111, the hole-transport layer 112, the light-emitting layer 113, the electron-transport layer 114, and the electron-injection layer 115 described above. In particular, an organometallic complex which is one embodiment of the present invention is suitably used for the light-emitting layer 113.

A specific example in which the light-emitting element described in this embodiment is manufactured is described.

The substrate 100 is used as a support of the light-emitting element. For example, glass, quartz, plastic, or the like can be used for the substrate 100. Furthermore, a flexible substrate may be used. The flexible substrate is a substrate that can be bent, such as a plastic substrate made of polycarbonate, polyarylate, or polyether sulfone, for example. A film (made of polypropylene, a polyester, poly(vinyl fluoride), poly(vinyl chloride), or the like), an inorganic film formed by evaporation, or the like can be used. Note that another substrate may be used as long as it can function as a support in a process of manufacturing the light-emitting element.

As the first electrode 101 and the second electrode 103, a metal, an alloy, an electrically conductive compound, a mixture thereof, and the like can be used. Specifically, indium oxide-tin oxide (ITO: indium tin oxide), indium oxide-tin oxide containing silicon or silicon oxide, indium oxide-zinc oxide, indium oxide containing tungsten oxide and zinc oxide, gold (Au), platinum (Pt), nickel (Ni), tungsten (W), chromium (Cr), molybdenum (Mo), iron (Fe), cobalt (Co), copper (Cu), palladium (Pd), and titanium (Ti) can be used. In addition, an element belonging to Group 1 or Group 2 of the periodic table, for example, an alkali metal such as lithium (Li) or cesium (Cs), an alkaline earth metal such as calcium (Ca) or strontium (Sr), magnesium (Mg), an alloy containing such an element (MgAg or AlLi), a rare earth metal such as europium (Eu) or ytterbium (Yb), an alloy containing such an element, graphene, and the like can be used. The first electrode 101 and the second electrode 103 can be formed by, for example, a sputtering method, an evaporation method (including a vacuum evaporation method), or the like.

As the substance having a high hole-transport property used for the hole-injection layer 111 and the hole-transport layer 112, a π-electron rich heteroaromatic compound (e.g., a carbazole derivative or an indole derivative) or an aromatic amine compound is preferable. For example, any of the following substances can be used: a compound having an aromatic amine skeleton such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF); a compound having a carbazole skeleton such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP); a compound having a thiophene skeleton such as 4,4',4''-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV); and a compound having a furan skeleton such as 4,4',4''-(benzene-1,3,5-triyl)tri(dibenzofuran) (abbreviation: DBF3P-II), or 4-{3-[3-(9-phenyl-9H-fluoren-9-yl)phenyl]phenyl}dibenzofuran (abbreviation: mmDBFFLBi-II). Among the above materials, a compound having an aromatic amine skeleton and a compound having a carbazole skeleton are preferable because these compounds are highly reliable and have high hole-transport properties to contribute to a reduction in drive voltage.

Further, as a material that can be used for the hole-injection layer 111 and the hole-transport layer 112, a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD) can be used.

As each of the hole-injection layer 111 and the hole-transport layer 112, a layer in which any of the substances having a high hole-transport property given above and a substance having an acceptor property are mixed is preferably used, in which case a favorable carrier-injection property is obtained. As examples of the acceptor substance used, a transition metal oxide or an oxide of a metal belonging to any of Group 4 to Group 8 of the periodic table can be given. Specifically, molybdenum oxide is particularly preferable.

The light-emitting layer 113 is preferably a layer which includes, for example, an electron-transport material as a host material, a hole-transport material as an assist material, and a light-emitting material, which converts triplet-excitation energy into light emission, as a guest material.

As the electron-transport material that can be used as the above-described host material in the light-emitting layer 113, a π-electron deficient heteroaromatic compound such as a nitrogen-containing heteroaromatic compound is preferable. For example, the following can be given: heterocyclic compounds (e.g., an oxadiazole derivative, an imidazole derivative, and a triazole derivative) having polyazole skeletons, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds (e.g., a pyrazine derivative, a pyrimidine derivative, a pyridazine derivative, a quinoxaline derivative, and a dibenzoquinoxaline derivative) having diazine skeletons, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl] pyrimidine (abbreviation: 4,6mPnP2Pm), and 4,6-bis[3-(4-dibenzothienyl)phenyl]pyrimidine (abbreviation: 4,6mDBTP2Pm-II); and heterocyclic compounds (e.g., a pyridine derivative, a quinoline derivative, and a dibenzoquinoline derivative) having pyridine skeletons, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above materials, a heterocyclic compound having a diazine skeleton and a heterocyclic compound having a pyridine skeleton are highly reliable and thus preferable. Specifically, a heterocyclic compound having a diazine (pyrimidine or pyrazine) skeleton has a high electron-transport property to contribute to a reduction in drive voltage.

As the hole-transport material that can be used as the assist material in the light-emitting layer 113, a substance having a high hole-transport property, which can be used for the hole-injection layer 111 and the hole-transport layer 112, can be used.

Note that it is preferable that these electron-transport materials and hole-transport materials do not have an absorption spectrum in the blue wavelength region. Specifically, an absorption edge of the absorption spectrum is preferably at 440 nm or less.

An example of the light-emitting material which converts triplet excitation energy into light emission in the light-emitting layer 113 is an organometallic complex of one embodiment of the present invention. Another example of such a material is a thermally activated delayed fluorescent (TADF) material exhibiting thermally activated delayed fluorescence.

As the light-emitting material which converts triplet excitation energy into light emission, any of the phosphorescent materials given below can also be used instead of an organometallic complex of one embodiment of the present invention. For example, a phosphorescent material having an emission peak at 440 nm to 520 nm is given, examples of which include organometallic iridium complexes having 4H-triazole skeletons, such as tris{2-[5-(2-methylphenyl)-4-(2,6-dimethylphenyl)-4H-1,2,4-triazol-3-yl-kN$^2$]phenyl-kC}iridium(III) (abbreviation: Ir(mpptz-dmp)$_3$), tris(5-methyl-3,4-diphenyl-4H-1,2,4-triazolato)iridium(III) (abbreviation: Ir(Mptz)$_3$), and tris[4-(3-biphenylyl)-5-isopropyl-3-phenyl-4H-1,2,4-triazolato]iridium(III) (abbreviation: Ir(iPrptz-3b)$_3$); organometallic iridium complexes having 1H-triazole skeletons, such as tris[3-methyl-1-(2-methylphenyl)-5-phenyl-1H-1,2,4-triazolato]iridium(III) (abbreviation: Ir(Mptz1-mp)$_3$) and tris(1-methyl-5-phenyl-3-propyl-1H-1,2,4-triazolato)iridium(III) (abbreviation: Ir(Prptz1-Me)$_3$); organometallic iridium complexes having imidazole skeletons, such as fac-tris[1-(2,6-diisopropylphenyl)-2-phenyl-1H-imidazole]iridium(III) (abbreviation: Ir(iPrpmi)$_3$) and tris[3-(2,6-dimethylphenyl)-7-methylimidazo[1,2-f]phenanthridinato]iridium(III) (abbreviation: Ir(dmpimpt-Me)$_3$); and organometallic iridium complexes in which aphenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$] iridium(III) picolinate (abbreviation: FIrpic), bis{2-[3',5'-bis(trifluoromethyl)phenyl]pyridinato-N,C$^{2'}$}iridium(III) picolinate (abbreviation: Ir(CF$_3$ppy)$_2$(pic)), and bis[2-(4',6'-difluorophenyl)pyridinato-N,C$^{2'}$]iridium(III) acetylacetonate (abbreviation: Firacac). Among the materials given above, the organometallic iridium complex having a 4H-triazole skeleton has high reliability and high emission efficiency and is thus especially preferable.

Examples of the phosphorescent material having an emission peak at 520 nm to 600 nm include organometallic iridium complexes having pyrimidine skeletons, such as tris(4-methyl-6-phenylpyrimidinato)iridium(III) (abbreviation: Ir(mppm)$_3$), tris(4-t-butyl-6-phenylpyrimidinato)iridium(III) (abbreviation: Ir(tBuppm)$_3$), (acetylacetonato)bis(6-methyl-4-phenylpyrimidinato)iridium(III) (abbreviation: Ir(mppm)$_2$(acac)], (acetylacetonato)bis(6-tert-butyl-4-phenylpyrimidinato)iridium(III) (abbreviation: Ir(tBuppm)$_2$(acac)), (acetylacetonato)bis[6-(2-norbornyl)-4-phenylpyrimidinato]iridium(III) (abbreviation: Ir(nbppm)$_2$(acac)), (acetylacetonato)bis[5-methyl-6-(2-methylphenyl)-4-phenylpyrimidinato]iridium(III) (abbreviation: Ir(mpmppm)$_2$(acac)), and (acetylacetonato)bis(4,6-diphenylpyrimidinato)iridium (III) (abbreviation: Ir(dppm)$_2$(acac)); organometallic iridium complexes having pyrazine skeletons, such as (acetylacetonato)bis(3,5-dimethyl-2-phenylpyrazinato)iridium(III) (abbreviation: Ir(mppr-Me)$_2$(acac)) and (acetylacetonato)bis(5-isopropyl-3-methyl-2-phenylpyrazinato)iridium(III) (abbreviation: Ir(mppr-iPr)$_2$(acac)); organometallic iridium complexes having pyridine skeletons, such as tris(2-phenylpyridinato-N,C$^{2'}$)iridium(III) (abbreviation: Ir(ppy)$_3$), bis(2-phenylpyridinato-N,C$^{2'}$)iridium(III) acetylacetonate (abbreviation: Ir(ppy)$_2$acac)), bis(benzo[h]quinolinato)iridium (III) acetylacetonate (abbreviation: Ir(bzq)$_2$(acac)), tris(benzo[h]quinolinato)iridium(III) (abbreviation: Ir(bzq)$_3$), tris(2-phenylquinolinato-N,C$^{2'}$)iridium(III) (abbreviation: Ir(pq)$_3$), and bis(2-phenylquinolinato-N,C$^{2'}$)iridium(III) acetylacetonate (abbreviation: Ir(pq)$_2$(acac)); and a rare earth metal complex such as tris(acetylacetonato) (monophenanthroline)terbium(III) (abbreviation: Tb(acac)$_3$(Phen)).

Examples of the phosphorescent material having an emission peak at 600 nm to 700 nm include organometallic iridium complexes having pyrimidine skeletons, such as bis[4,6-bis(3-methylphenyl)pyrimidinato](diisobutylylmethano)iridium(III) (abbreviation: Ir(5mdppm)$_2$(dibm)), bis[4,6-bis(3-methylphenyl)pyrimidinato](dipivaloylmethanato)iridium (III) (abbreviation: Ir(5mdppm)$_2$(dpm)), and bis[4,6-di(naphthalen-1-yl)pyrimidinato](dipivaloylmethanato) iridium(III) (abbreviation: Ir(dlnpm)$_2$(dpm)); organometallic iridium complexes having pyrazine skeletons, such as (acetylacetonato)bis(2,3,5-triphenylpyrazinato)iridium(III) (abbreviation: Ir(tppr)$_2$(acac)), bis(2,3,5-triPhenylpyrazinato) (dipivaloylmethanato)iridium(III) (abbreviation: Ir(tppr)$_2$(dpm)), or (acetylacetonato)bis[2,3-bis(4-fluorophenyl) quinoxalinato]iridium(III) (abbreviation: Ir(Fdpq)$_2$(acac)); organometallic iridium complexes having pyridine skeletons, such as tris(1-phenylisoquinolinato-N,C$^{2'}$)iridium(III) (abbreviation: Ir(piq)$_3$) and bis(1-phenylisoquinolinato-N,C$^{2'}$) iridium(III)acetylacetonate (abbreviation: Ir(piq)$_2$acac)); a platinum complex such as 2,3,7,8,12,13,17,18-octaethyl-21H,23H-porphyrin platinum(II) (abbreviation: PtOEP); and rare earth metal complexes such as tris(1,3-diphenyl-1,3-propanedionato) (monophenanthroline)europium(III) (abbreviation: Eu(DBM)$_3$(Phen)) and tris[1-(2-thenoyl)-3,3,3-trifluoroacetonato] (monophenanthroline)europium(III) (abbreviation: Eu(TTA)$_3$(Phen)). Alternatively, an organometallic complex which is one embodiment of the present invention can be used.

The electron-transport layer 114 includes a substance having a high electron-transport property. For the electron-transport layer 114, it is possible to use, in addition to the electron-transport materials given above, a metal complex such as tris(8-quinolinolato)aluminum (abbreviation: Alq$_3$), tris(4-methyl-8-quinolinolato)aluminum (abbreviation: Almq$_3$), bis(10-hydroxybenzo[h]quinolinato)beryllium (abbreviation: BeBq$_2$), BAlq, Zn(BOX)$_2$, or bis[2-(2-hydroxyphenyl)berizothiazolato]zinc (abbreviation: Zn(BTZ)$_2$). Alternatively, a heteroaromatic compound such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), or 4,4'-bis(5-methylbenzoxazol-2-yl)stilbene (abbreviation: BzOs) can be used. Further alternatively, a high molecular compound such as poly(2,5-pyridinediyl) (abbreviation: PPy), poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy) can be used. The substances mentioned here are mainly ones that have an electron mobility of $10^{-6}$ cm$^2$/V·s or higher. Note that any substance other than the above substances may be used for the electron-transport layer 114 as long as the electron-transport property is higher than the hole-transport property.

Furthermore, the electron-transport layer 114 is not limited to a single layer, and two or more layers including the aforementioned substances may be stacked.

The electron-injection layer 115 includes a substance having a high electron-injection property. For the electron-injection layer 115; a compound of an alkali metal, an alkaline earth metal, such as lithium fluoride (LiF), cesium fluoride (CsF), calcium fluoride (CaF$_2$), or lithium oxide (LiO$_x$) can be used. Alternatively, a rare earth metal compound like erbium fluoride (ErF$_3$) can be used. Further alternatively, the above-described substances for forming the electron-transport layer 114 can be used.

Alternatively, a composite material in which an organic compound and an electron donor (donor) are mixed may be used for the electron-injection layer 115. The composite material is superior in an electron-injection property and an electron-transport property, since electrons are generated in the organic compound by the electron donor. In this case, the organic compound is preferably a material excellent in transporting the generated electrons. Specifically, for example, the above-described substances for forming the electron-transport layer 114 (e.g., a metal complex and a heteroaromatic compound) can be used. As the electron donor, any substance which shows an electron-donating property with respect to an organic compound can be used. Specifically, an alkali metal, an alkaline earth metal or a rare earth metal is preferable, and for example, lithium, cesium, erbium, or ytterbium, can be given. Further, an alkali metal oxide or an alkaline earth metal oxide is preferable, and for example, lithium oxide, calcium oxide, barium oxide, and the like can be given. Alternatively, magnesium can also be used. Alternatively, Lewis base such as magnesium oxide can be used. Further alternatively, an organic compound such as tetrathiafulvalene (abbreviation: TTF) can be used.

Note that each of the above-described hole-injection layer 111, hole-transport layer 112, light-emitting layer 113, electron-transport layer 114, and electron-injection layer 115, can be formed by a method such as an evaporation method (e.g., a vacuum evaporation method), an inkjet method, or a coating method.

In the above-described light-emitting element, current flows due to a potential difference generated between the first electrode 101 and the second electrode 103 and holes and electrons recombine in the EL layer 102, so that light is emitted. Then, the emitted light is extracted outside through one or both of the first electrode 101 and the second electrode 103. Therefore, one or both of the first electrode 101 and the second electrode 103 are electrodes having a light-transmitting property.

Note that the structure described in this embodiment can be used in combination with any of the structures described in the other embodiments, as appropriate.

(Embodiment 3)

In this embodiment, modes of an organometallic complex and a light-emitting element including the organometallic complex as an emission center according to one embodiment of the present invention, which are different from those in Embodiment 2, are described with reference to FIGS. 2A and 2B.

Figure 2A:
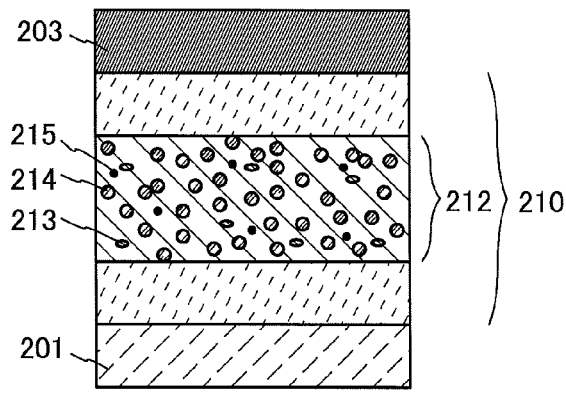
FIGS. 2A and 2B illustrate a light-emitting element according to one embodiment of the present invention.
Figure 2B:
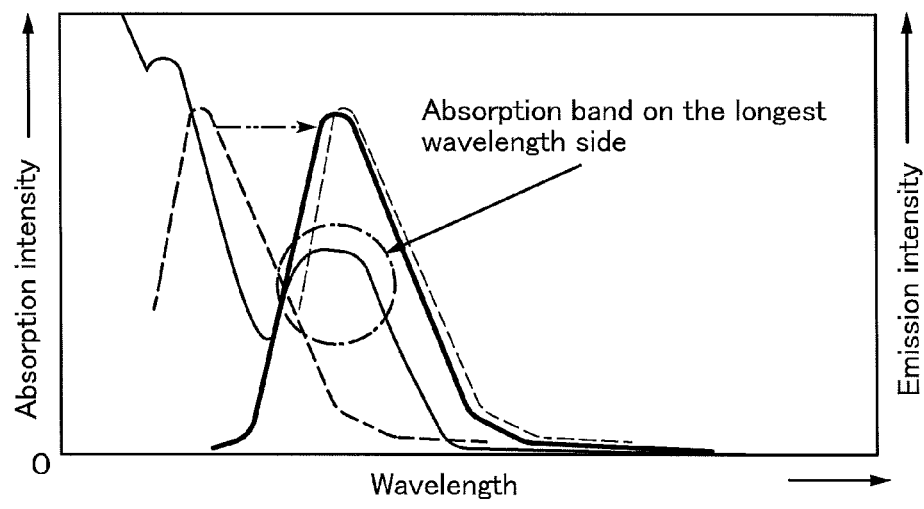

A light-emitting element described in this embodiment includes an EL layer 210 between a pair of electrodes (a first electrode 201 and a second electrode 203) as illustrated in FIG. 2A. Note that the EL layer 210 includes at least a light-emitting layer 212 and may include a hole-injection layer, an electron-transport layer, an electron-injection layer, and the like. Note that for the hole-injection layer, the electron-transport layer, and the electron-injection layer, the substances described in Embodiment 2 can be used. Furthermore, the first electrode 201 is used as an anode and the second electrode 203 is used as a cathode in this embodiment.

The EL layer 210 in this embodiment includes an organometallic complex of one embodiment of the present invention.

The light-emitting layer 212 includes a first organic compound 213, a second organic compound 214, and a third organic compound 215. In this embodiment, the first organic compound 213, the second organic compound 214, and the third organic compound 215 are used as a host material, an assist material, and a guest material, respectively. An organometallic complex of one embodiment of the present invention can be used, for example, as the third organic compound 215 used as the guest material.

When the light-emitting layer 212 has the structure in which the guest material is dispersed in the host material, crystallization of the light-emitting layer can be suppressed. Further, it is possible to suppress concentration quenching due to high concentration of the guest material, and thus the light-emitting element can have higher emission efficiency.

Note that it is preferable that the triplet excited energy level (T$_1$ level) of each of the first organic compound 213 (host material) and the second organic compound 214 (assist material) be higher than the T$_1$ level of the third organic compound 215 (guest material). This is because, when the T$_1$ level of the first organic compound 213 (or the second organic compound 214) is lower than the T$_1$ level of the third organic compound 215, the triplet excited energy of the third organic compound 215, which is to contribute to light emission, is quenched by the first organic compound 213 (or the second organic compound 214) and accordingly the emission efficiency decreases.

Here, for improvement in the efficiency of energy transfer from the host material to the guest material, Förster mechanism (dipole-dipole interaction) and Dexter mechanism (electron exchange interaction), which are known as mechanisms of energy transfer between molecules, are considered. According to the mechanisms, it is preferable that an emission spectrum of a host material (a fluorescence spectrum in energy transfer from a singlet excited state, and a phosphorescence spectrum in energy transfer from a triplet excited state) largely overlap with an absorption spectrum of a guest material (specifically, a spectrum in an absorption band on the longest wavelength (lowest energy) side). However, in the case of a general phosphorescent guest material, it is difficult to obtain an overlap between a fluorescence spectrum of the host material and an absorption spectrum in an absorption band on the longest wavelength (lowest energy) side of the guest material. The reason for this is as follows: if the fluorescence spectrum of the host material overlaps with the absorption spectrum in the absorption band on the longest wavelength (lowest energy) side of the guest material, since a phosphorescence spectrum of the host material is located on a longer wavelength (lower energy) side than the fluorescence spectrum, the $T_1$ level of the host material becomes lower than the $T_1$ level of the phosphorescent compound and the above-described problem of quenching occurs; yet, when the host material is designed so that the $T_1$ level of the host material is higher than the $T_1$ level of the phosphorescent compound to avoid the problem of quenching, the fluorescence spectrum of the host material is shifted to the shorter wavelength (higher energy) side, and thus the fluorescence spectrum does not have any overlap with the absorption spectrum in the absorption band on the longest wavelength (lowest energy) side of the guest material. For that reason, in general, it is difficult to obtain an overlap between a fluorescence spectrum of the host material and an absorption spectrum in an absorption band on the longest wavelength (lowest energy) side of the guest material so as to maximize energy transfer from a singlet excited state of the host material.

Thus, in this embodiment, a combination of the first organic compound 213 and the second organic compound 214 preferably forms an excited complex (also referred to as exciplex). Such a combination allows, in the light-emitting layer 212, a fluorescence spectrum of the first organic compound 213 and that of the second organic compound 214 to be converted into an emission spectrum of the exciplex which is located on a longer wavelength side. Moreover, when the first organic compound 213 and the second organic compound 214 are selected so that the emission spectrum of the exciplex largely overlaps with the absorption spectrum of the guest material (third organic compound 215), energy transfer from a singlet excited state can be maximized (see FIG. 2B).

As for a triplet excited state, energy transfer from the exciplex, not from the host material, is assumed to occur.

An electron-transport material described in Embodiment 2 is preferably used as the first organic compound 213. A hole-transport material described in Embodiment 2 is preferably used as the second organic compound 214. An organometallic complex which is one embodiment of the present invention is preferably used as the third organic compound 215.

The above-described combination of the first organic compound 213 and the second organic compound 214 is an example of the combination which enables an exciplex to be formed. The combination is determined so that the emission spectrum of the exciplex overlaps with the absorption spectrum of the third organic compound 215 and that the peak of the emission spectrum of the exciplex has a longer wavelength than the peak of the absorption spectrum of the third organic compound 215.

Since the electron-transport material and the hole-transport material form the first organic compound 213 and the second organic compound 214, adjusting the mixture ratio therebetween can control the carrier balance. Specifically, the ratio of the first organic compound to the second organic compound is preferably 1:9 to 9:1.

In the light-emitting element described in this embodiment, energy transfer efficiency can be improved owing to energy transfer utilizing an overlap between an emission spectrum of the exciplex and an absorption spectrum of the phosphorescent compound; thus, it is possible to achieve high external quantum efficiency of the light-emitting element.

Note that the structure described in this embodiment can be used in combination with any of the structures described in the other embodiments, as appropriate.

(Embodiment 4)

In this embodiment, as one embodiment of the present invention, a light-emitting element (hereinafter referred to as a tandem light-emitting element) in which a plurality of EL layers is included so that a charge generation layer is sandwiched therebetween is described.

Figure 3A:
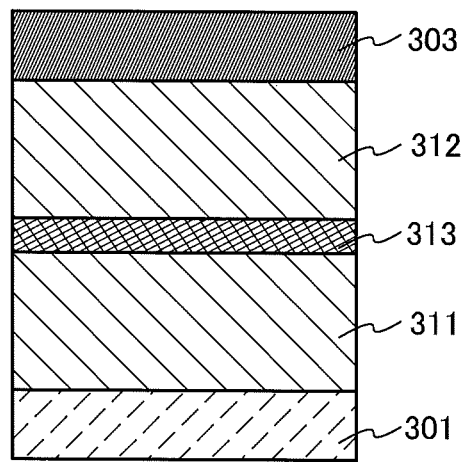
FIGS. 3A and 3B each illustrate a light-emitting element according to one embodiment of the present invention.

The light-emitting element described in this embodiment is a tandem light-emitting element including a plurality of light-emitting layers (a first light-emitting layer 311 and a second light-emitting layer 312) between a pair of electrodes (a first electrode 301 and a second electrode 303), as illustrated in FIG. 3A.

In this embodiment, the first electrode 301 functions as an anode, and the second electrode 303 functions as a cathode. Note that the first electrode 301 and the second electrode 303 can have structures similar to those described in Embodiment 2. In addition, although the plurality of light-emitting layers (the first light-emitting layer 311 and the second light-emitting layer 312) may have structures similar to those described in Embodiment 2, any of the light-emitting layers may have a structure similar to that described in Embodiment 2. In other words, the structures of the first light-emitting layer 311 and the second light-emitting layer 312 may be the same or different from each other and can be similar to those described in Embodiment 2.

Further, a charge generation layer 313 is provided between the plurality of light-emitting layers (the first light-emitting layer 311 and the second light-emitting layer 312). The charge generation layer 313 has a function of injecting electrons into one of the light-emitting layers and injecting holes into the other of the light-emitting layers when a voltage is applied to the first electrode 301 and the second electrode 303. In this embodiment, when a voltage is applied such that the potential of the first electrode 301 is higher than that of the second electrode 303, the charge generation layer 313 injects electrons into the first light-emitting layer 311 and injects holes into the second light-emitting layer 312.

Note that in terms of light extraction efficiency, the charge generation layer 313 preferably has a light-transmitting property with respect to visible light (specifically, the average visible light transmittance greater than or equal to 40% and less than or equal to 100%). Further, the charge generation layer 313 functions even if it has lower conductivity than the first electrode 301 or the second electrode 303.

The charge generation layer 313 may have either a structure in which an electron acceptor (acceptor) is added to an organic compound having a high hole-transport property or a structure in which an electron donor (donor) is added to an organic compound having a high electron-transport property. Alternatively, both of these structures may be stacked.

In the case of the structure in which an electron acceptor is added to an organic compound having a high hole-transport property, as the organic compound having a high hole-transport property, for example, an aromatic amine compound such as NPB, TPD, TDATA, MTDATA, or 4,4'-bis[N-(spiro-9,9'-bifluoren-2-yl)-N-phenylamino]biphenyl (abbreviation: BSPB), or the like can be used. The substances mentioned here are mainly ones that have a hole mobility of $10^{-6}$ cm$^2$/V·s or higher. However, substances other than the above substances may be used as long as they are organic compounds in which a hole-transport property is higher than an electron-transport property.

Further, as the electron acceptor, 7,7,8,8-tetracyano-2,3,5,6-tetrafluoroquinodimethane (abbreviation: F4-TCNQ), chloranil, and the like can be given. In addition, a transition metal oxide can be given. In addition, an oxide of metals that belong to Group 4 to Group 8 of the periodic table can be given. Specifically, vanadium oxide, niobium oxide, tantalum oxide, chromium oxide, molybdenum oxide, tungsten oxide, manganese oxide, and rhenium oxide are preferable since their electron-accepting property is high. Among these, molybdenum oxide is especially preferable since it is stable in the air, its hygroscopic property is low, and it is easily treated.

On the other hand, in the case of the structure in which an electron donor is added to an organic compound having a high electron-transport property, as the organic compound having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based ligand or a thiazole-based ligand, such as Zn(BOX)$_2$ or Zn(BTZ)$_2$ can be used. Further alternatively, other than such a metal complex, PBD, OXD-7, TAZ, BPhen, BCP, or the like can be used. The substances mentioned here are mainly ones that have an electron mobility of $10^{-6}$ cm$^2$/V·s or higher. Note that any substance other than the above substances may be used as long as the electron-transport property is higher than the hole-transport property.

As the electron donor, it is possible to use an alkali metal, an alkaline earth metal, a rare earth metal, a metal belonging to Group 13 of the periodic table, or an oxide or a carbonate thereof. Specifically, it is preferable to use lithium (Li), cesium (Cs), calcium (Ca), ytterbium (Yb), indium (In), lithium oxide, cesium carbonate, or the like. Alternatively, magnesium (Mg), may be used. Alternatively, an organic compound such as tetrathianaphthacene may be used as the electron donor.

Note that forming the charge generation layer 313 by using any of the above materials can suppress an increase in driving voltage caused by the stack of the light-emitting layers.

Figure 3B:
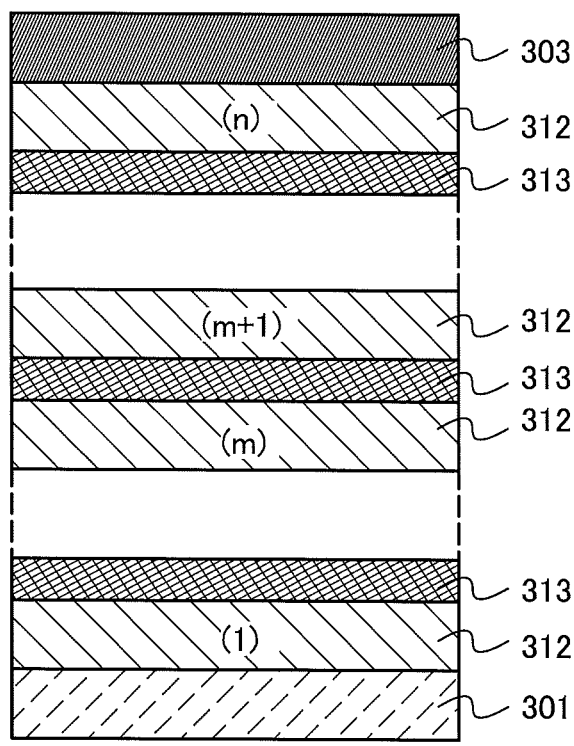

Although the light-emitting element having the two light-emitting layers is illustrated in FIG. 3A, the present invention can also be applied to a light-emitting element in which n light-emitting layers (n is an integer of three or more) are stacked as illustrated in FIG. 3B. In the case where a plurality of light-emitting layers is included between a pair of electrodes as in the light-emitting element according to this embodiment, by provision of the charge generation layer 313 between the light-emitting layers, light emission in a high luminance region can be obtained with current density kept low. Since the current density can be kept low, the element can have a long lifetime. When the light-emitting element is used for lighting, voltage drop due to resistance of an electrode material can be reduced, thereby achieving uniform light emission in a large area. Moreover, a light-emitting device which has low power consumption and can be driven at a low voltage can be achieved.

Further, by forming light-emitting layers to emit light of different colors, a light-emitting element that can provide light emission of a desired color as a whole can be obtained. For example, by forming a light-emitting element having two light-emitting layers so that the emission color of the first light-emitting layer and the emission color of the second light-emitting layer are complementary colors, the light-emitting element can provide white light emission as a whole. Note that the team "complementary" means color relationship in which an achromatic color is obtained when colors are mixed. In other words, white light emission can be obtained by mixture of light from substances, of which the light emission colors are complementary colors.

Further, the same can be applied to a light-emitting element having three light-emitting layers. For example, the light-emitting element as a whole can provide white light emission when the emission color of a first light-emitting layer is red, the emission color of a second light-emitting layer is green, and the emission color of a third light-emitting layer is blue.

Note that the structure described in this embodiment can be used in combination with any of the structures described in the other embodiments, as appropriate.

(Embodiment 5)

In this embodiment, a light-emitting device which is one embodiment of the present invention is described.

Figure 4:
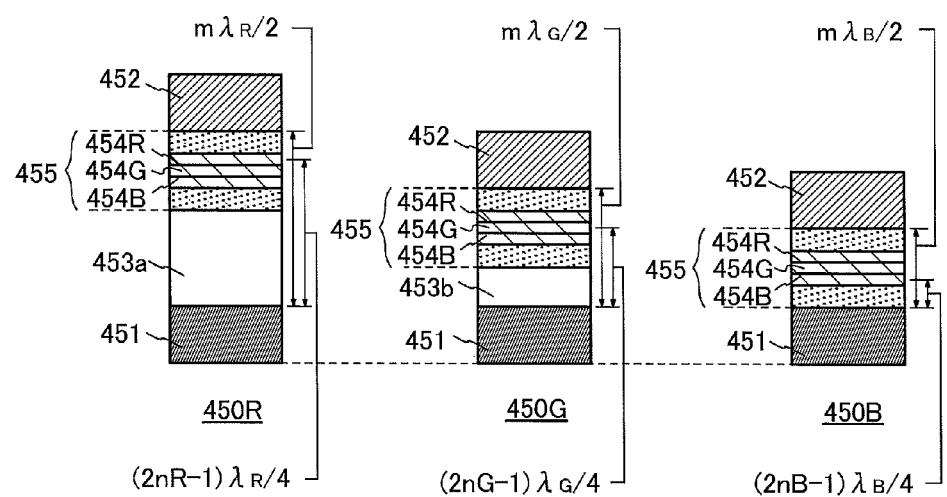
FIG. 4 illustrates a light-emitting element and a light-emitting device according to one embodiment of the present invention.

A light-emitting device described in this embodiment has a micro optical resonator (microcavity) structure in which a light resonant effect between a pair of electrodes is utilized. The light-emitting device includes a plurality of light-emitting elements each of which includes at least an EL layer 455 between a pair of electrodes (a reflective electrode 451 and a semi-transmissive and semi-reflective electrode 452) as illustrated in FIG. 4. Further, the EL layer 455 includes at lest light-emitting layers 454 (454R, 454G, and 454B), and may further include a hole-transport layer, a hole-injection layer, an electron-transport layer, an electron-injection layer, a charge generation layer, and the like.

An organometallic complex according to the present invention can be used for the EL layer 455. The use of an organometallic complex according to the present invention for the EL layer 455 enables the light-emitting device to have excellent light-emitting characteristics and high reliability.

The first light-emitting element 450R has a structure in which a first transparent conductive layer 453a, the EL layer 455 part of which includes a first light-emitting layer 454B, a second light-emitting layer 454E and a third light-emitting layer 454R, the semi-transmissive and semi-reflective electrode 452 are sequentially stacked over the reflective electrode 451. The second light-emitting element 450G has a structure in which a second transparent conductive layer 453b, the EL layer 455, and the semi-transmissive and semi-reflective electrode 452 are sequentially stacked over the reflective electrode 451. The third light-emitting element 450B has a structure in which the EL layer 455 and the semi-transmissive and semi-reflective electrode 452 are sequentially stacked over the reflective electrode 451.

Note that the reflective electrode 451, the EL layer 455, and the semi-transmissive and semi-reflective electrode 452 are common to the light-emitting elements (the first light-emitting element. 450R, the second light-emitting element 450G and the third light-emitting element 450B). The first light-emitting layer 454B emits light ($\lambda_B$) having a peak in the wavelength region from 420 nm to 480 nm, the second light-emitting layer 454G emits light ($\lambda_G$) having a peak in the wavelength region from 500 nm to 550 nm, and the third light-emitting layer 454R emits light ($\lambda_R$) having a peak in the wavelength region from 600 nm to 760 nm. Thus, in each of the light-emitting elements (the first light-emitting element 450R, the second light-emitting element 450G and the third light-emitting element 450B), light emitted from the first light-emitting layer 454B, light emitted from the second light-emitting layer 454G, and light emitted from the third light-emitting layer 454R overlap with each other; accordingly, light having a broad emission spectrum that covers a visible light range can be emitted. Note that the above wavelengths satisfy the following relation: $\lambda_B < \lambda_G < \lambda_R$.

Each of the light-emitting elements described in this embodiment has a structure in which the EL layer 455 is interposed between the reflective electrode 451 and the semi-transmissive and semi-reflective electrode 452. Light emitted in all directions from the light-emitting layers included in the EL layer 455 are resonated by the reflective electrode 451 and the semi-transmissive and semi-reflective electrode 452 which function as a micro optical resonator (microcavity). Note that the reflective electrode 451 is formed using a conductive material having reflectivity, and a film whose visible light reflectivity is 40% to 100%, preferably 70% to 100%, and whose resistivity is $1\times10^{-2}$ Ωcm or lower is used. In addition, the semi-transmissive and semi-reflective electrode 452 is formed using a conductive material having reflectivity and a conductive material having a light-transmitting property, and a film whose visible light reflectivity is 20% to 80%, preferably 40% to 70%, and whose resistivity is $1\times10^{-2}$ Ω/cm or lower is used.

In this embodiment, the thicknesses of the transparent conductive layers (the first transparent conductive layer 453*a* and the second transparent conductive layer 453*b*) provided in the first light-emitting element 450R and the second light-emitting element 450G, respectively, are varied between the light-emitting elements, whereby the light-emitting elements differ in the optical path length from the reflective electrode 451 to the semi-transmissive and semi-reflective electrode 452. In other words, in light having a broad emission spectrum, which is emitted from the light-emitting layers of each of the light-emitting elements, light with a wavelength that is resonated between the reflective electrode 451 and the semi-transmissive and semi-reflective electrode 452 can be enhanced while light with a wavelength that is not resonated therebetween can be attenuated. Thus, when the elements differ in the optical path length from the reflective electrode 451 to the semi-transmissive and semi-reflective electrode 452, light with different wavelengths can be extracted.

Note that the optical path length (also referred to as optical distance) is expressed as a product of an actual distance and a refractive index, and means in this embodiment, is a product of an actual thickness and n (refractive index). That is, the following relation is satisfied: optical path length=actual thickness×n.

Further, the optical path length from the reflective electrode 451 to the semi-transmissive and semi-reflective electrode 452 is set to $m\lambda_R/2$ (m is a natural number of 1 or more) in the first light-emitting element 450R; the optical path length from the reflective electrode 451 to the semi-transmissive and semi-reflective electrode 452 is set to $m\lambda_G/2$ (m is a natural number of 1 or more) in the second light-emitting element 450G; and the optical path length from the reflective electrode 451 to the semi-transmissive and semi-reflective electrode 452 is set to $m\lambda_B/2$ (m is a natural number of 1 or more) in the third light-emitting element 450B.

Thus, light ($\lambda_R$) emitted from the first light-emitting layer 454R included in the EL layer 455 is mainly extracted from the first light-emitting element 450R, light ($\lambda_G$) emitted from the second light-emitting layer 454G included in the EL layer 455 is mainly extracted from the second light-emitting element 450G and light ($\lambda_B$) emitted from the third light-emitting layer 454B included in the EL layer 455 is mainly extracted from the third light-emitting element 450B. Note that light extracted from each of the light-emitting elements is emitted through the semi-transmissive and semi-reflective electrode 452 side.

Further, strictly speaking, the optical path length from the reflective electrode 451 to the semi-transmissive and semi-reflective electrode 452 can be the distance from a reflection region in the reflective electrode 451 to a reflection region in the semi-transmissive and semi-reflective electrode 452. However, it is difficult to precisely determine the positions of the reflection regions in the reflective electrode 451 and the semi-transmissive and semi-reflective electrode 452; hence, it is assumed that the above effect can be sufficiently obtained wherever the reflection regions may be set in the reflective electrode 451 and the semi-transmissive and semi-reflective electrode 452.

Next, the optical path length from the reflective electrode 451 to the third light-emitting layer 454R is adjusted to $(2n_R-1)\lambda_R/4$ ($n_R$ is a natural number of 1 or more) because in the first light-emitting element 450R, light (first reflected light) that is reflected by the reflective electrode 451 of light emitted from the third light-emitting layer 454R interferes with light (first incident light) that directly enters the semi-transmissive and semi-reflective electrode 452 from the third light-emitting layer 454R. By adjusting the optical path length, the phases of the first reflected light and the first incident light can be aligned with each other and light emitted from the third light-emitting layer 454R can be amplified.

Note that, strictly speaking, the optical path length from the reflective electrode 451 to the third light-emitting layer 454R can be the optical path length from a reflection region in the reflective electrode 451 to a light-emitting region in the third light-emitting layer 454R. However, it is difficult to precisely determine the positions of the reflection region in the reflective electrode 451 and the light-emitting region in the third light-emitting layer 454R; hence, it is assumed that the above effect can be sufficiently obtained wherever the reflection region and the light-emitting region may be set in the reflective electrode 451 and the third light-emitting layer 454R, respectively.

Next, the optical path length from the reflective electrode 451 to the second light-emitting layer 454G is adjusted to $(2n_G-1)\lambda_G/4$ ($n_G$ is a natural number of 1 or more) because in the second light-emitting element 450G light (second reflected light) that is reflected by the reflective electrode 451 of light emitted from the second light-emitting layer 454G interferes with light (second incident light) that directly enters the semi-transmissive and semi-reflective electrode 452 from the second light-emitting layer 454G. By adjusting the optical path length, the phases of the second reflected light and the second incident light can be aligned with each other and light emitted from the second light-emitting layer 454G can be amplified.

Note that, strictly speaking, the optical path length from the reflective electrode 451 to the second light-emitting layer 454G can be the optical path length from a reflection region in the reflective electrode 451 to a light-emitting region in the second light-emitting layer 454G. However, it is difficult to precisely determine the positions of the reflection region in the reflective electrode 451 and the light-emitting region in the second light-emitting layer 454G; hence, it is assumed that the above effect can be sufficiently obtained wherever the reflection region and the light-emitting region may be set in the reflective electrode 451 and the second light-emitting layer 454G respectively.

Next, the optical path length from the reflective electrode 451 to the first light-emitting layer 454B is adjusted to $(2n_B-1)\lambda_B/4$ ($n_B$ is a natural number of 1 or more) because in the third light-emitting element 450B, light (third reflected light) that is reflected by the reflective electrode 451 of light emitted from the first light-emitting layer 454B interferes with light (third incident light) that directly enters the semi-transmissive and semi-reflective electrode 452 from the first light-emitting layer 454B. By adjusting the optical path length, the phases of the third reflected light and the third incident light can be aligned with each other and light emitted from the first light-emitting layer 454B can be amplified.

Note that, strictly speaking, the optical path length from the reflective electrode 451 to the first light-emitting layer 454B can be the optical path length from a reflection region in the reflective electrode 451 to a light-emitting region in the first light-emitting layer 454B. However, it is difficult to precisely determine the positions of the reflection region in the reflective electrode 451 and the light-emitting region in the first light-emitting layer 454B; hence, it is assumed that the above effect can be sufficiently obtained wherever the reflection region and the light-emitting region may be set in the reflective electrode 451 and the first light-emitting layer 454B, respectively.

Note that although each of the light-emitting elements in the above-described structure includes a plurality of light-emitting layers in the EL layer, the present invention is not limited thereto. For example, the structure of the tandem (stacked type) light-emitting element which is described in Embodiment 4 can be combined, in which case a plurality of light-emitting layers is provided so as to sandwich a charge generation layer in one light-emitting element.

The light-emitting device described in this embodiment has a microcavity structure, in which light with wavelengths which differ among the light-emitting elements can be extracted even when they include the EL layers having the same structure, so that it is not necessary to form light-emitting elements for the colors of R, G and B. Thus, this structure is advantageous for full color display owing to easiness in achieving higher resolution display or the like. In addition, emission intensity with a predetermined wavelength in the front direction can be increased, whereby power consumption can be reduced. This structure is particularly useful in the case of being used for a color display (image display device) including pixels of three or more colors but may also be used for lighting or the like.

Note that the structure described in this embodiment can be used in combination with any of the structures described in the other embodiments, as appropriate.

(Embodiment 6)

In this embodiment, a light-emitting device including a light-emitting element which is one embodiment of the present invention is described.

The light-emitting device can be either a passive matrix light-emitting device or an active matrix light-emitting device. In this embodiment, an active matrix light-emitting device is described with reference to FIGS. 5A and 5B.

Figure 5A:
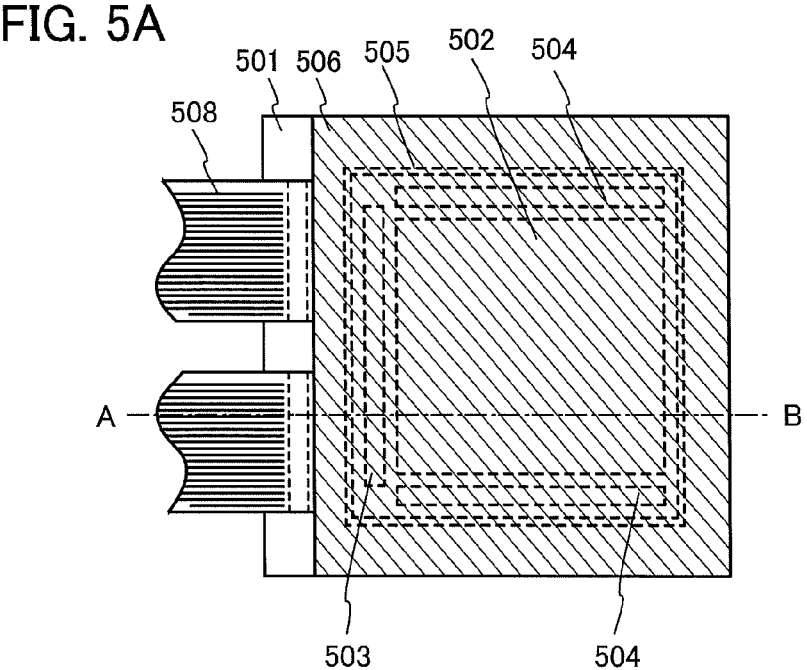
FIGS. 5A and 5B illustrate a light-emitting device according to one embodiment of the present invention.
Figure 5B:
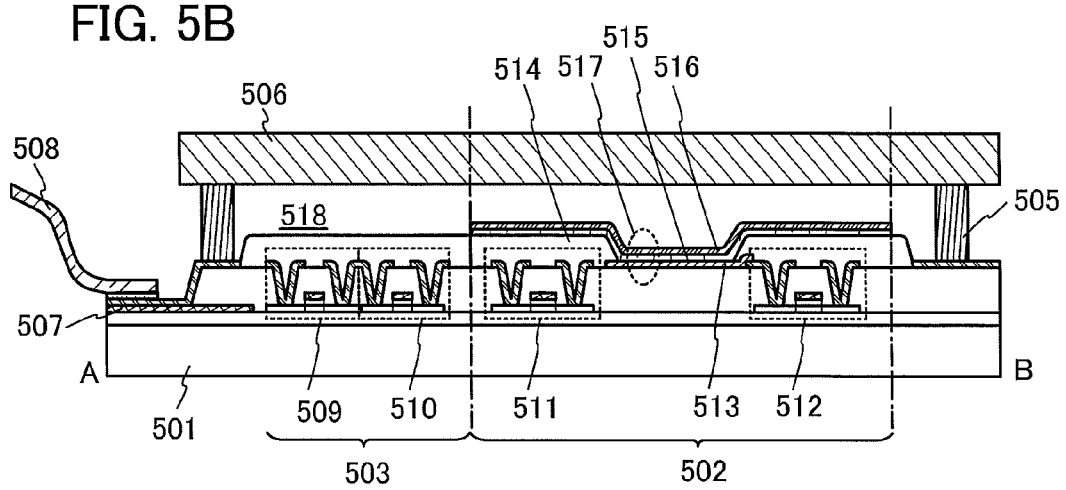

Note that FIG. 5A is a top view illustrating a light-emitting device and FIG. 5B is a cross-sectional view taken along the chain line A-B in FIG. 5A. The active matrix light-emitting device according to this embodiment includes a pixel portion 502 provided over an element substrate 501, a driver circuit portion (a source line driver circuit) 503, and driver circuit portions (gate line driver circuits) 504 (504a and 504b). The pixel portion 502, the driver circuit portion 503, and the driver circuit portions 504 are sealed between the element substrate 501 and a sealing substrate 506 by a sealant 505.

In addition, a lead wiring 507 is provided over the element substrate 501 to connect an external input terminal through which a signal (e.g., a video signal, a clock signal, a start signal, and a reset signal) or a potential from the outside is transmitted to the driver circuit portion 503 and the driver circuit portions 504. Here is shown an example in which a flexible printed circuit (FPC) 508 is provided as the external input terminal. Although the FPC 508 is illustrated alone, this FPC may be provided with a printed wiring board (PWB). The light-emitting device in the present specification includes, in its category, not only the light-emitting device itself but also the light-emitting device provided with the FPC or the PWB.

Next, a cross-sectional structure is described with reference to FIG. 5B. The driver circuit portion and the pixel portion are formed over the element substrate 501; here are illustrated the driver circuit portion 503 which is the source line driver circuit and the pixel portion 502.

The driver circuit portion 503 is an example where a CMOS circuit is formed, which is a combination of an n-channel TFT 509 and a p-channel TFT 510. Note that a circuit included in the driver circuit portion may be formed using various CMOS circuits, PMOS circuits, or NMOS circuits. Although this embodiment shows a driver integrated type in which the driver circuit is formed over the substrate, the driver circuit is not necessarily formed over the substrate, and the driver circuit can be formed outside, not over the substrate.

The pixel portion 502 is formed of a plurality of pixels each of which includes a switching TFT 511, a current control TFT 512, and a first electrode 513 which is electrically connected to a wiring (a source electrode or a drain electrode) of the current control TFT 512. Note that an insulator 514 is formed to cover end portions of the first electrode 513. Here, the insulator 514 is formed using a positive photosensitive acrylic resin. Note also that the first electrode 513 is used as an anode in this embodiment.

The insulator 514 preferably has a curved surface with curvature at an upper end portion or a lower end portion thereof in order to obtain favorable coverage by a film which is to be stacked over the insulator 514. For example, in the case of using a positive photosensitive acrylic resin as a material for the insulator 514, the insulator 514 preferably has a curved surface with a curvature radius (0.2 μm to 3 μm) at the upper end portion. Note that the insulator 514 can be foamed using either a negative photosensitive resin or a positive photosensitive resin. It is possible to use, without limitation to an organic compound, either an organic compound or an inorganic compound such as silicon oxide or silicon oxynitride.

An EL layer 515 and a second electrode 516 are stacked over the first electrode 513. The EL layer 515 can have any of the structures described in the above embodiments, and can include an organic EL material of one embodiment of the present invention. Note that the first electrode 513 is used as an anode and a second electrode 516 is used as a cathode in this embodiment.

A light-emitting element 517 is formed of a stacked structure of the first electrode 513, the EL layer 515, and the second electrode 516. For the first electrode 513, the EL layer 515, and the second electrode 516, the materials described in Embodiment 2 can be used. Although not illustrated, the second electrode 516 is electrically connected to an FPC 508 which is an external input terminal.

Although the cross-sectional view of FIG. 5B illustrates only one light-emitting element 517, a plurality of light-emitting elements is arranged in a matrix in the pixel portion 502. Light-emitting elements which provide three kinds of light emission (R, and B) are selectively formed in the pixel portion 502, whereby a light-emitting device capable of full color display can be fabricated. Alternatively, a light-emitting device which is capable of full color display may be fabricated by a combination with color filters.

Further, the sealing substrate 506 is attached to the element substrate 501 with the sealant 505, whereby a light-emitting element 517 is provided in a space 518 surrounded by the element substrate 501, the sealing substrate 506, and the sealant 505. The space 518 may be filled with an inert gas (such as nitrogen or argon), or the sealant 505.

An epoxy-based resin is preferably used for the sealant 505. It is preferable that such a material do not transmit moisture or oxygen as much as possible. As the sealing substrate 506, a glass substrate, a quartz substrate, or a plastic substrate formed of fiberglass reinforced plastic (FRP), polyvinyl fluoride (PVF), polyester, acrylic, or the like can be used.

As described above, an active matrix light-emitting device can be obtained.

Note that the structure described in this embodiment can be combined as appropriate with any of the structures described in the other embodiments.

(Embodiment 7)

In this embodiment, an electronic device which partly includes the light-emitting device of one embodiment of the present invention which is described in the above embodiments will be described. Examples of the electronic device include cameras such as video cameras and digital cameras, goggle type displays, navigation systems, audio replay devices (e.g., car audio systems and audio systems), computers, game machines, portable information terminals (e.g., mobile computers, mobile phones, smartphones, portable game machines, e-book readers, and tablet terminals), and image replay devices in which a recording medium is provided (specifically, devices that are capable of replaying recording media such as digital versatile discs (DVDs) and equipped with a display device that can display an image). Specific examples of these electronic devices will be described with reference to FIGS. 6A to 6D and FIGS. 7A to 7D.

Figure 6A:
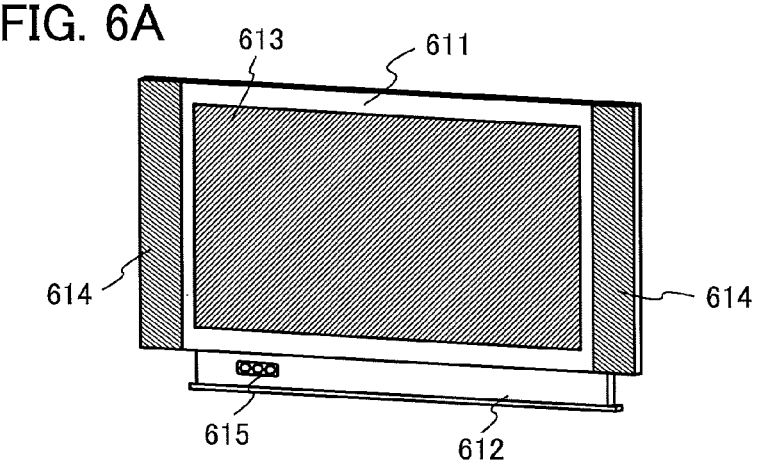
FIGS. 6A to 6D each illustrate an electronic device according to one embodiment of the present invention.

FIG. 6A illustrates a television set according to one embodiment of the present invention, which includes a housing 611, a supporting base 612, a display portion 613, speaker portions 614, video input terminals 615, and the like. In this television set, the light-emitting device of one embodiment of the present invention can be applied to the display portion 613. Since the light-emitting device of one embodiment of the present invention has high reliability and a long lifetime, by the application of the light-emitting device of one embodiment of the present invention, a television set with excellent light-emitting characteristics and high reliability can be obtained.

Figure 6B:
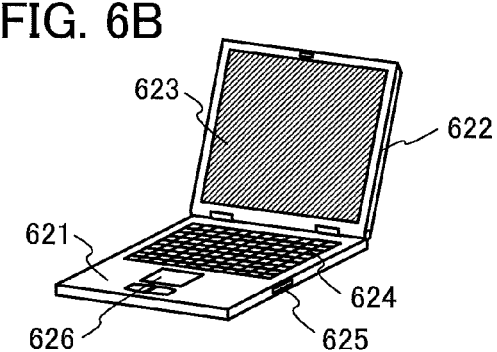

FIG. 6B illustrates a computer according to one embodiment of the present invention, which includes a main body 621, a housing 622, a display portion 623, a keyboard 624, an external connection port 625, a pointing device 626, and the like. In this computer, the light-emitting device of one embodiment of the present invention can be applied to the display portion 623. Since the light-emitting device of one embodiment of the present invention has high reliability and a long lifetime, by the application of the light-emitting device of one embodiment of the present invention, a computer with excellent light-emitting characteristics and high reliability can be obtained.

Figure 6C:
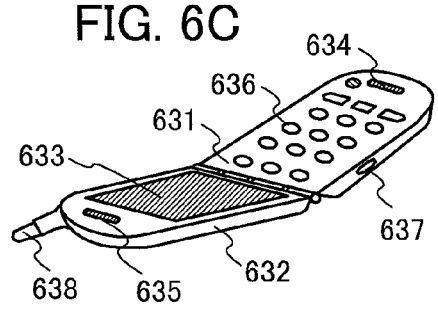

FIG. 6C illustrates a mobile phone according to one embodiment of the present invention, which includes a main body 631, a housing 632, a display portion 633, an audio input portion 634, an audio output portion 635, operation keys 636, an external connection port 637, an antenna 638, and the like. In this mobile phone, the light-emitting device of one embodiment of the present invention can be applied to the display portion 633. Since the light-emitting device of one embodiment of the present invention has high reliability and a long lifetime, by the application of the light-emitting device of one embodiment of the present invention, a mobile phone with excellent light-emitting characteristics and high reliability can be obtained.

Figure 6D:
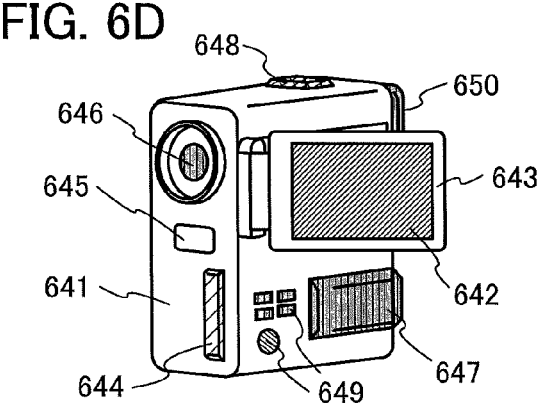

FIG. 6D illustrates a camera according to one embodiment of the present invention, which includes a main body 641, a display portion 642, a housing 643, an external connection port 644, a remote control receiving portion 645, an image receiving portion 646, a battery 647, an audio input portion 648, operation keys 649, an eyepiece portion 650, and the like. In this camera, the light-emitting device of one embodiment of the present invention can be applied to the display portion 642. Since the light-emitting device of one embodiment of the present invention has high reliability and a long lifetime, by the application of the light-emitting device of one embodiment of the present invention, a camera with excellent light-emitting characteristics and high reliability can be obtained.

FIGS. 7A to 7D illustrate examples of mobile terminals according to one embodiment of the present invention. FIGS. 7A to 7C illustrate a mobile terminal 5000, and 7D illustrates a mobile terminal 6000.

FIGS. 7A to 7C are a front view, a side view, and a rear view of the mobile terminal 5000, respectively. FIG. 7D is a front view of the mobile terminal 6000.

The mobile terminal 5000 includes a housing 5001, a display portion 5003, a power button 5005, a front camera 5007, a rear camera 5009, a first external connection terminal 5011, a second external connection terminal 5013, and the like.

In addition, the display portion 5003 is incorporated in the housing 5001 and can be used as a touch panel. For example, e-mailing or schedule management can be performed by touching an icon 5015 and the like on the display portion 5003. Further, the front camera 5007 is incorporated on the front side of the housing 5001, whereby an image on the user's side can be taken. The rear camera 5009 is incorporated in the rear side of the housing 5001, whereby an image on the opposite side of the user can be taken. Further, the housing 5001 includes the first external connection terminal 5011 and the second external connection terminal 5013. For example, sound can be output to an earphone or the like through the first external connection terminal 5011, and data can be moved through the second external connection terminal 5013.

The mobile terminal 6000 in FIG. 7D includes a first housing 6001, a second housing 6003, a hinge portion 6005, a first display portion 6007, a second display portion 6009, a power button 6011, a first camera 6013, a second camera 6015, and the like.

The first display portion 6007 is incorporated in the first housing 6001. The second display portion 6009 is incorporated in the second housing 6003. For example, the first display portion 6007 and the second display portion 6009 are used as a display panel and a touch panel, respectively. A user can select images, enter characters, and so on by touching an icon 6019 displayed on the second display portion 6009 or a keyboard 6021 (actually, a keyboard image displayed on the second display portion 6009) while looking at a text icon 6017 displayed on the first display portion 6007.

Alternatively, the first display portion 6007 and the second display portion 6009 may be a touch panel and a display panel, respectively; the first display portion 6007 and the second display portion 6009 may be touch panels.

The first housing 6001 and the second housing 6003 are connected to each other and open and close on the hinge portion 6005. In such a structure, the first display portion 6007 incorporated in the first housing 6001 and the second display portion 6009 incorporated in the second housing 6003 are preferably made to face each other in carrying the mobile terminal 6000, in which case the surfaces of the first display portion 6007 and the second display portion 6009 (e.g., plastic substrates) can be protected.

Alternatively, the first housing 6001 and the second housing 6003 may be separated by the hinge portion 6005 (so-called convertible type). Thus, the application range of the mobile terminal 6000 can be extended: for example, the first housing 6001 is used in a vertical orientation and the second housing 6003 is used in a horizontal orientation.

Further, the first camera 6013 and the second camera 6015 can take 3D images.

The mobile terminal 5000 and the mobile terminal 6000 may send and receive data wirelessly. For example, through wireless internet connection, desired data can be purchased and downloaded.

The mobile terminals 5000 and 6000 can have other functions such as a function of displaying various kinds of data (e.g., a still image, a moving image, and a text image), a function of displaying a calendar, a date, the time, or the like on the display portion, a touch-input function of operating or editing the data displayed on the display portion by touch input, and a function of controlling processing by various kinds of software (programs). A detector such as a photodetector capable of optimizing display luminance in accordance with the amount of outside light or a sensor for detecting inclination, like a gyroscope or an acceleration sensor, can be included.

The light-emitting device of one embodiment of the present invention can be applied to the display portion 5003 of the mobile terminal 5000, the first display portion 6007 of the mobile terminal 6000, and/or the second display portion 6009 of the mobile terminal 6000. Since the light-emitting device of one embodiment of the present invention has high reliability and a long lifetime, by the application of the light-emitting device of one embodiment of the present invention, a mobile terminal with excellent light-emitting characteristics and high reliability can be obtained.

As described above, the applicable range of the light-emitting device of one embodiment of the present invention is so wide that the light-emitting device can be applied to electronic devices in a variety of fields. With the use of the light-emitting device of one embodiment of the present invention, an electronic device with excellent light-emitting characteristics, high reliability, and a long lifetime can be obtained.

The light-emitting device of one embodiment of the present invention can also be used as a lighting device. Specific examples of the lighting device are described with reference to FIGS. 8A to 8C.

Figure 8A:
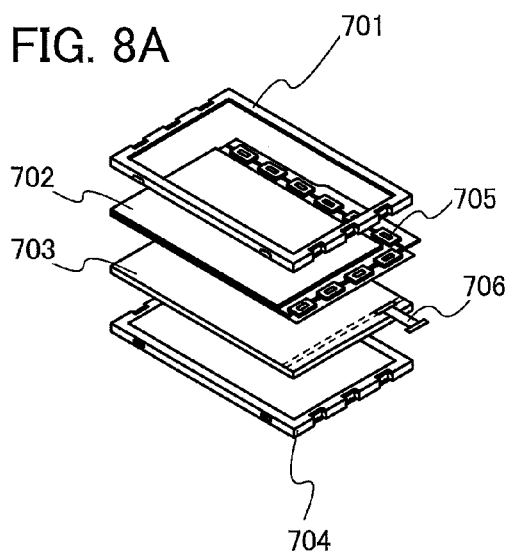
FIGS. 8A to 8C illustrate lighting devices and electronic devices according to one embodiment of the present invention.

FIG. 8A illustrates an example of a liquid crystal display device using the light-emitting device of one embodiment of the present invention as a backlight. The liquid crystal display device illustrated in FIG. 8A includes a housing 701, a liquid crystal panel 702, a backlight 703, and a housing 704. The liquid crystal panel 702 is connected to a driver IC 705. The light-emitting device of one embodiment of the present invention is used as the backlight 703, and current is supplied through a terminal 706. By using the light-emitting device of one embodiment of the present invention as a backlight of a liquid crystal display device as described above, a backlight with high reliability and a long lifetime can be obtained. Moreover, since the light-emitting device of one embodiment of the present invention is a lighting device for surface light emission and the enlargement of the light-emitting device is possible, the backlight can be made larger. Thus, a larger-area liquid crystal display device with low power consumption can be obtained.

Figure 8B:
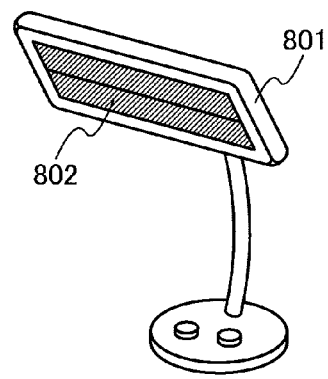

Next, FIG. 8B illustrates an example in which the light-emitting device of one embodiment of the present invention is used for a desk lamp which is a lighting device. The desk lamp illustrated in FIG. 8B includes a housing 801 and a light source 802, and the light-emitting device of one embodiment of the present invention is used as the light source 802. By the application of the light-emitting device of one embodiment of the present invention, a desk lamp with excellent light-emitting characteristics and high reliability can be obtained.

Figure 8C:
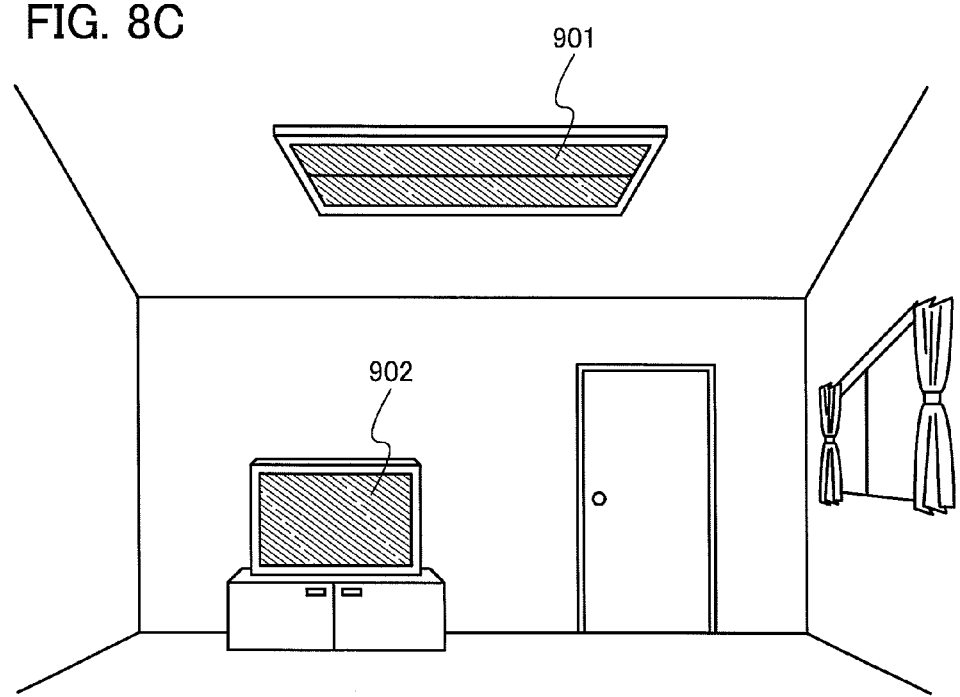

FIG. 8C illustrates an example in which the light-emitting device of one embodiment of the present invention is used for an indoor lighting device 901. Since the light-emitting device of one embodiment of the present invention can also have a larger area, the light-emitting device of one embodiment of the present invention can be used as a lighting system having a large area. Since the light-emitting device of one embodiment of the present invention has high reliability and a long lifetime, by the application of the light-emitting device of one embodiment of the present invention, a lighting device with high reliability can be obtained. In a room where the light-emitting device of one embodiment of the present invention is used for the indoor lighting device 901 as described above, a television set 902 of one embodiment of the present invention as described with reference to FIG. 6A can be installed so that public broadcasting and movies can be watched.

Note that the structure described in this embodiment can be used in combination with any of the structures described in the other embodiments, as appropriate.

EXAMPLE 1

Synthesis Example 1

Synthesis Example 1 specifically illustrates a synthesis example of bis[2-(benzofuro[3,2-d]pyrimidin-4-yl-κN3)phenyl-κC](2,4-pentanedionato-κ²O,O')iridium(III) (abbreviation: Ir(pbfpm)₂(acac)), the organometallic complex according to the present invention which is represented by the structural formula (100) in Embodiment 1. A structure of Ir(pbfpm)₂(acac) is illustrated below.

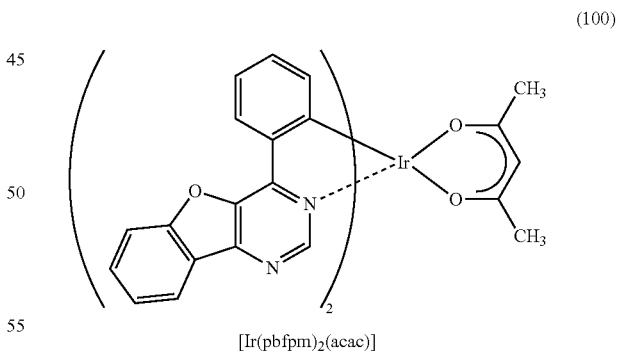

(100)

[Ir(pbfpm)₂(acac)]

Step 1: Synthesis of
4-Phenylbenzofuro[3,2-d]pyrimidine (abbreviation: Hpbfpm)

First, 2.42 g of 4-chlorobenzofuro[3,2-d]pyrimidine, 2.19 g of phenylboronic acid, 1.89 g of sodium carbonate, 0.10 g of bis(triphenylphosphine)palladium(II)dichloride (abbreviation: Pd(PPh₃)₂Cl₂), 20 mL of water, and 20 mL of acetonitrile were put into a recovery flask equipped with a reflux pipe, and the air in the flask was replaced with argon. This reaction container was heated by 60-minute microwave irradiation (2.45 GHz, 100 W). After that, the obtained residue was suction-filtered with water and washed with hexane. The obtained solid was purified by flash column chromatography using a developing solvent in which the ratio of hexane to ethyl acetate was 2:1, so that Hpbfpm, which was the pyrimidine derivative to be produced, was obtained as a white powder in a yield of 45%. Note that the microwave irradiation was performed using a microwave synthesis system (Discover, manufactured by CEM Corporation). A synthesis scheme of Step 1 is illustrated in (d-1) below.

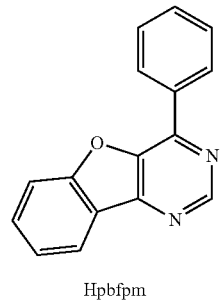

Hpbfpm

Step 2: Synthesis of Di-μ-chloro-tetrakis[2-(benzofuro[3,2-d]pyrimidin-4-yl-κN3)phenyl-κC]diiridium (III) (abbreviation: [Ir(pbfpm)₂Cl]₂)

Next, 15 mL of 2-ethoxyethanol, 5 mL of water, 1.32 g of Hpbfpmg obtained in Step 1 above, and 0.78 g of iridium chloride hydrate (IrCl₃.H₂O) were put into a recovery flask equipped with a reflux pipe, and the air in the flask was replaced by argon. After that, microwave irradiation (2.45 GHz, 100 W) was performed for 1 hour to cause a reaction. The solvent was distilled off, and then the obtained residue was suction-filtered and washed with ethanol to give a dinuclear complex [Ir(pbfpm)₂Cl]₂ as a reddish brown powder in a yield of 88%. A synthesis scheme of Step 2 is illustrated in (d-2) below.

(d-1)

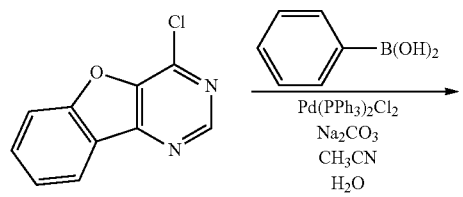

(d-2)

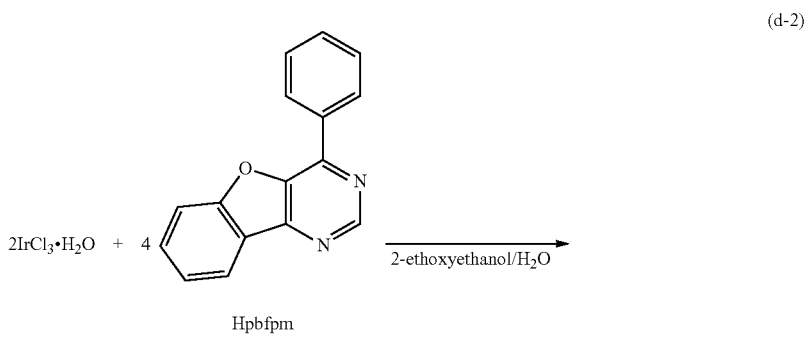

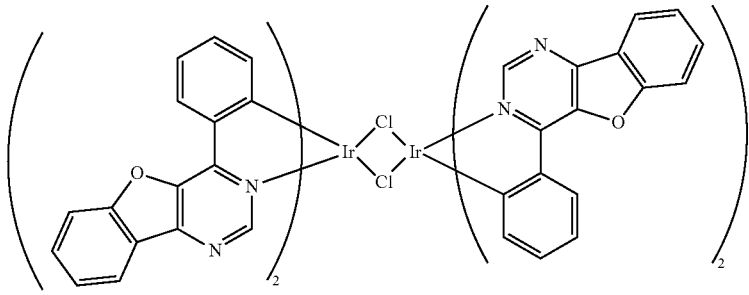

[Ir(pbfpm)₂Cl]₂

Step 3: Synthesis of Bis[2-(benzofuro[3,2-d]pyrimidin-4-yl-κN3)phenyl-κC](2,4-pentanedionato-κ²O, O')iridium(III) (abbreviation: Ir(pbfpm)₂(acac)

Figure 10:
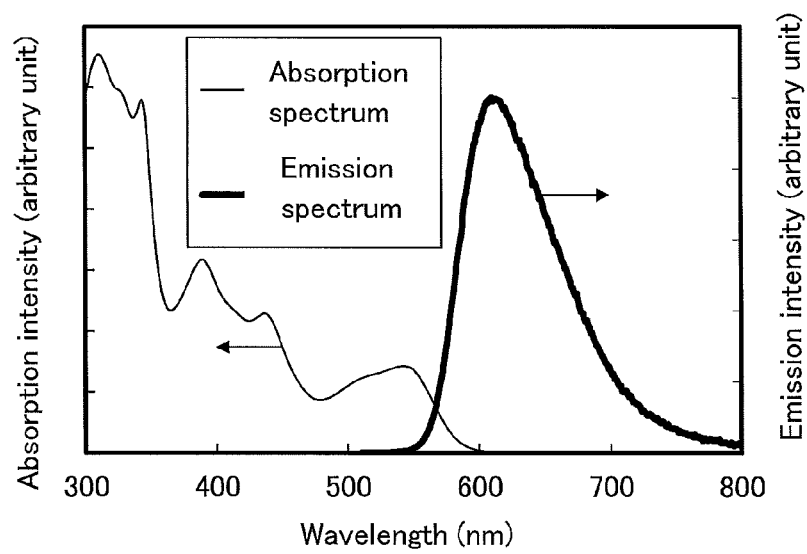
FIG. 10 shows an ultraviolet-visible absorption spectrum and an emission spectrum of Ir(pbfpm)$_2$(acac), which is an organometallic complex according to one embodiment of the present invention, in a dichloromethane solution.

Further, 30 mL of 2-ethoxyethanol, 1.66 g of the dinuclear complex [Ir(pbfpm)₂Cl]₂ obtained in Step 2 above, 0.36 g of acetylacetone, and 1.30 g of sodium carbonate were put into a recovery flask equipped with a reflux pipe and the inside air of the flask was replaced with argon. Then, microwave irradiation (2.45 GHz, 120 W) was performed for 60 minutes. Further, 0.24 g of acetylacetone was added, and the reaction container was heated by microwave irradiation under conditions of 110° C. and 120 W for 1 hour. The solvent was distilled off, and the obtained residue was suction-filtered with ethanol. The obtained solid was washed with water and ethanol The obtained solid was purified by flash column chromatography using a developing solvent in which the ratio of hexane to ethyl acetate was 2:1. After that, recrystallization was carried out with a mixed solvent of dichloromethane and ethanol, so that Ir(pbfpm)₂(acac), which is an organometallic complex according to the present invention, was obtained as a red powder in a yield of 6%. A synthesis scheme of Step 3 is illustrated in (d-3) below.

tometer (V-550, produced by JASCO Corporation) using a dichloromethane solution (0.090 mmol/L) at room temperature. Further, an emission spectrum of Ir(pbfpm)₂(acac) was measured. The emission spectrum was measured with a fluorescence spectrophotometer (FS920, produced by Hamamatsu Photonics K.K.) using a degassed dichloromethane solution (0.090 mmol/L) at room temperature. FIG. 10 shows the measurement results. In FIG. 10, the horizontal axis represents wavelength and the vertical axes represent molar absorption coefficient and emission intensity.

As shown in FIG. 10, Ir(pbfpm)₂(acac), which is an organometallic complex according to the present invention, has an emission peak at 610 nm, and reddish orange light emission was observed from the dichloromethane solution.

Further, the absolute quantum yield of Ir(pbfpm)₂(acac) was measured. After the concentration was adjusted with toluene as a solvent so as to be $1.0\times10^{-5}$ mol/L, the absolute quantum yield was measured at room temperature with an absolute PL quantum yield measurement system (C9920-02, produced by Hamamatsu Photonics Corporation). As a result, the absolute quantum yield was 83%, which indicates high emission efficiency.

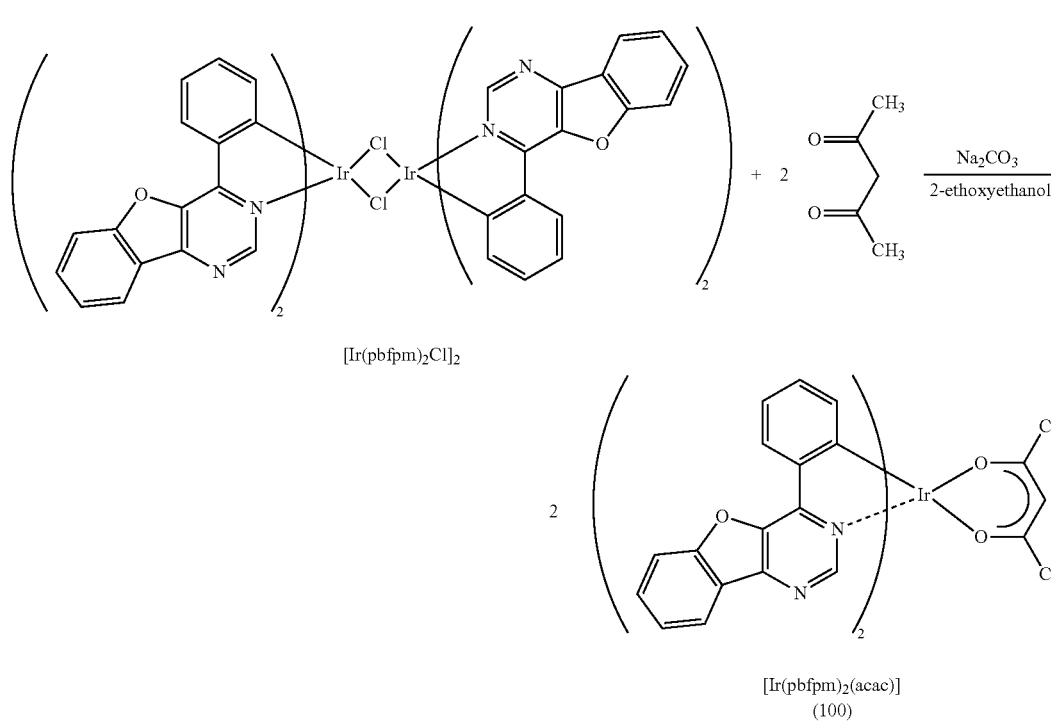

[Ir(pbfpm)₂Cl]₂

[Ir(pbfpm)₂(acac)]
(100)

Figure 9:
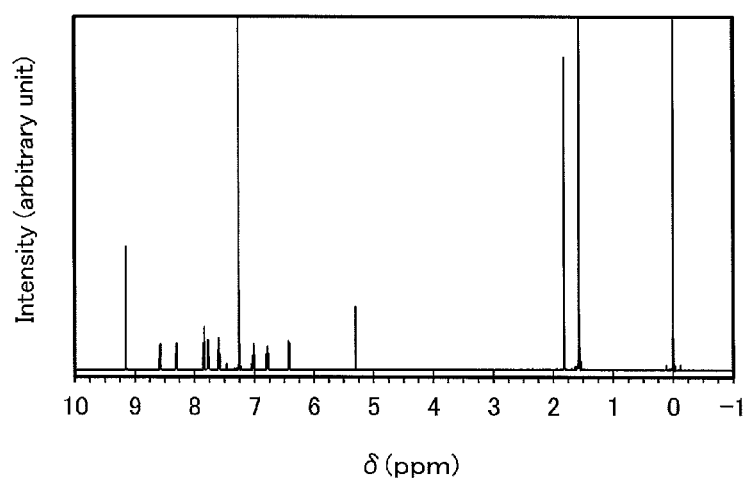
FIG. 9 is a $^1$H NMR chart of Ir(pbfpm)$_2$(acac), which is an organometallic complex according to one embodiment of the present invention.

Note that results of the analysis in which the red powder obtained in Step 3 above was analyzed by nuclear magnetic resonance spectrometry (¹H-NMR) are given below. The ¹H NMR chart is shown in FIG. 9. These results revealed that Ir(pbfpm)₂(acac), the organometallic complex according to the present invention which is represented by the above structural formula (100), was obtained in Synthesis Example 1.

¹H-NMR. δ (CDCl₃): 1.82 (s, 6H), 5.30 (s, 1H), 6.42 (d, 2H), 6.79 (t, 2H), 7.02 (t, 2H), 7.60 (t, 2H), 7.78 (t, 2H), 7.85 (d, 2H), 8.31 (d, 2H), 8.57 (d, 2H), 9.15 (s, 2H).

Next, an analysis of Ir(pbfpm)₂(acac) was conducted by an ultraviolet-visible absorption spectrometry. The UV spectrum was measured with an ultraviolet-visible spectropho-

EXAMPLE 2

Synthesis Example 2

Synthesis Example 2 specifically illustrates a synthesis example of bis[2-(benzofuro[3,2-d]pyrimidin-4-yl-κN3)-4,6-dimethylphenyl-κC](2,2',6,6'-tetramethyl-3,5-heptanedionato-κ²O,O')iridium(III) (abbreviation: Ir(dmpbfpm)₂(dpm)), the organometallic complex according to the present invention which is represented by the structural formula (101) in Embodiment 1. A structure of Ir(dmpbfpm)₂(dpm) is illustrated below.

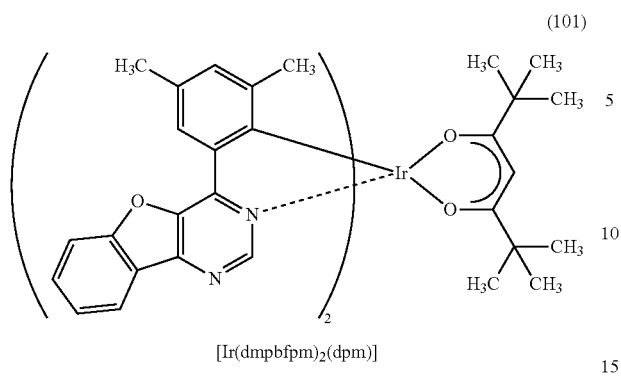

[Ir(dmpbfpm)₂(dpm)] (101)

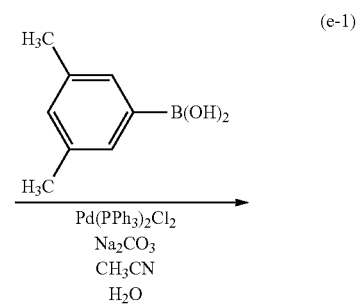
(e-1)

Step 1: Synthesis of 4-(3,5-Dimethylphenyl)benzofuro[3,2-d]pyrimidine (abbreviation: Hdmpbfpm)

First, 4.02 g of 4-chlorobenzofuro[3,2-d]pyrimidine, 4.52 g of 3,5-dimethylphenylboronic acid, 3.21 g of sodium carbonate, 0.17 g of bis(triphenylphosphine)palladium(II) dichloride (abbreviation: Pd(PPh₃)₂Cl₂), 20 mL of water, and 20 mL of acetonitrile were put into a recovery flask equipped with a reflux pipe, and the air in the flask was replaced with argon. This reaction container was subjected to microwave irradiation (2.45 GHz, 100 W) for 60 minutes. Further, 0.75 g of 3,5-dimethylphenylboronic acid, 0.53 g of sodium carbonate, and 0.043 g of Pd(PPh₃)₂Cl₂ were added to the mixture, and the reaction container was heated again by 60-minute microwave irradiation (2.45 GHz, 100 W). After that, water was added to this solution and extraction with dichloromethane was carried out. The obtained solution of the extract was washed with water and saturated brine and dried with magnesium sulfate. After the drying, the solution was filtered. The solvent of this solution was distilled off, and then the obtained residue was purified by flash column chromatography using a developing solvent in which the ratio of dichloromethane to ethyl acetate was 10:1, so that Hdmpbfpm, which was the pyrimidine derivative to be produced, was obtained as a white powder in a yield of 74%. Note that the microwave irradiation was performed using a microwave synthesis system (Discover, manufactured by CEM Corporation). A synthesis scheme of Step 1 is illustrated in (e-1) below.

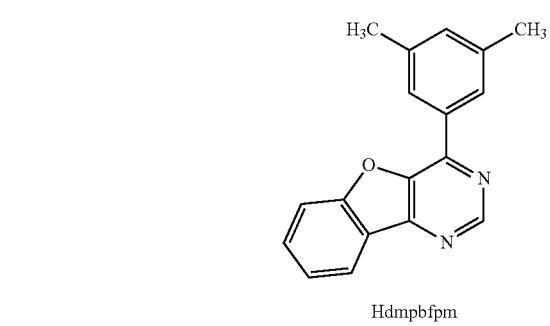

Hdmpbfpm

Step 2: Synthesis of Di-μ-chloro-tetrakis[2-(benzofuro[3,2-d]pyrimidin-4-yl-κN3)-4,6-dimethylphenyl-κC]d iiridium(III) (abbreviation: [Ir(dmpbfpm)₂Cl]₂)

Next, 15 mL of 2-ethoxyethanol, 5 mL of water, 2.47 g of Hdmpbfpm obtained in Step 1 above, and 1.30 g of iridium chloride hydrate (IrCl₃.H₂O) were put into a recovery flask equipped with a reflux pipe, and the air in the flask was replaced with argon. Then, the mixture was heated by 30-minute microwave irradiation (2.45 GHz, 100 W). The solvent was distilled off, and then the obtained residue was suction-filtered and washed with ethanol to give a dinuclear complex [Ir(dmpbfpm)₂Cl]₂ as a reddish brown powder in a yield of 92%. A synthesis scheme of Step 2 is illustrated in (e-2) below.

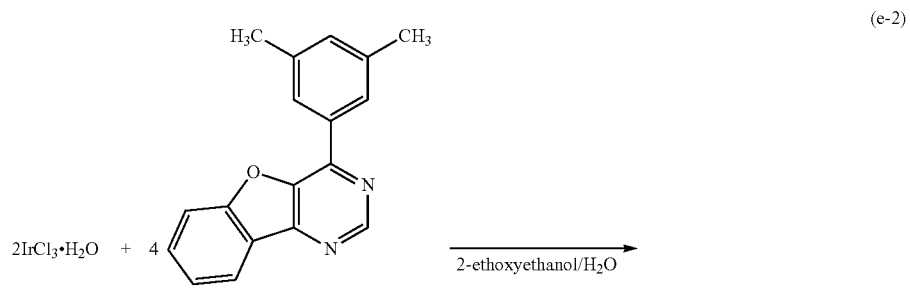
(e-2)

Hdmpbfpm

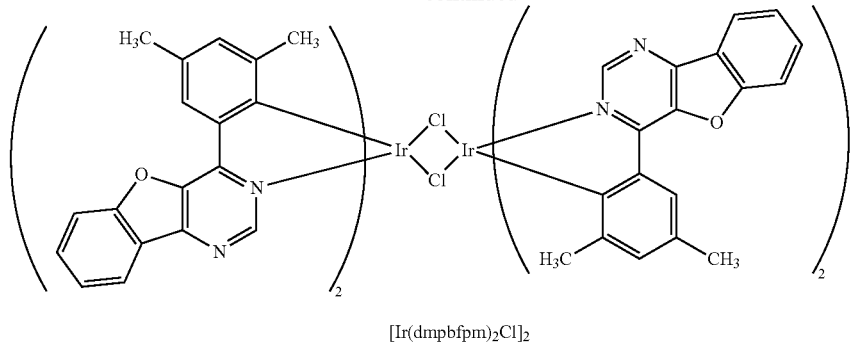

[Ir(dmpbfpm)₂Cl]₂

Step 3: Synthesis of Bis[2-(benzofuro[3,2-d]pyrimidin-4-yl-κN3)-4,6-dimethylphenyl-κC](2,2',6,6'-tetramethyl-3,5-heptanedionato-κ²O,O')iridium(III) (abbreviation: Ir(dmpbfpm)₂(dpm))

Further, 30 mL of 2-ethoxyethanol, 3.09 g of [Ir(dmpbfpm)₂ Cl]₂ which is the dinuclear complex obtained in Step 2 above, 1.10 g of dipivaloylmethane, and 2.10 g of sodium carbonate were put into a recovery flask equipped with a reflux pipe, and the air in the flask was replaced with argon. Then, microwave irradiation (2.45 GHz, 120 W) was performed for 60 minutes. Here, 0.55 g of dipivaloylmethane was added to the mixture, the air in the flask was replaced with argon, and the reaction container was irradiated with microwaves under conditions of 110° C. and 200 W for 1 hour. Furthermore, 0.55 g of dipivaloylmethane was added to the mixture, the air in the flask was replaced with argon, and the mixture was heated to 110° C. by 60-minute microwave irradiation (2.45 GHz, 200 W). After that, the solvent was distilled off, and the obtained residue was suction-filtered with ethanol. The obtained solid was washed with water and ethanol. Here, 2.45 g of the obtained solid, 0.55 g of dipivaloylmethane, and 1.11 g of sodium carbonate were put into a recovery flask equipped with a reflux pipe, and the air in the flask was replaced with argon. After that, the mixture was heated to 110° C. by 60-minute microwave irradiation (2.45 GHz, 200 W). Here, 0.55 g of dipivaloylmethane was added to the mixture, the air in the flask was replaced with argon, and the reaction container was irradiated with microwaves under conditions of 110° C. and 200 W for 1 hour. After that, the solvent was distilled off, and the obtained residue was suction-filtered with ethanol. The obtained solid was washed with water and ethanol. This solid was dissolved in dichloromethane, and the mixture was filtered through a filter aid in which Celite, alumina, and Celite were stacked in this order. The solvent of this solution was distilled off, and the obtained residue was purified by flash column chromatography using a developing solvent in which the ratio of hexane to ethyl acetate was 5:1. After that, recrystallization was carried out with a mixed solvent of dichloromethane and ethanol, and then the mixture was purified by flash column chromatography using a developing solvent in which the ratio of hexane to ethyl acetate was 2:1. After that, recrystallization was carried out with a mixed solvent of dichloromethane and ethanol, so that Ir(dmpbfpm)₂(dpm), which is an organometallic complex according to the present invention, was obtained as a red powder in a yield of 5%. A scheme of the synthesis of Step 3 is illustrated in (e-3) below.

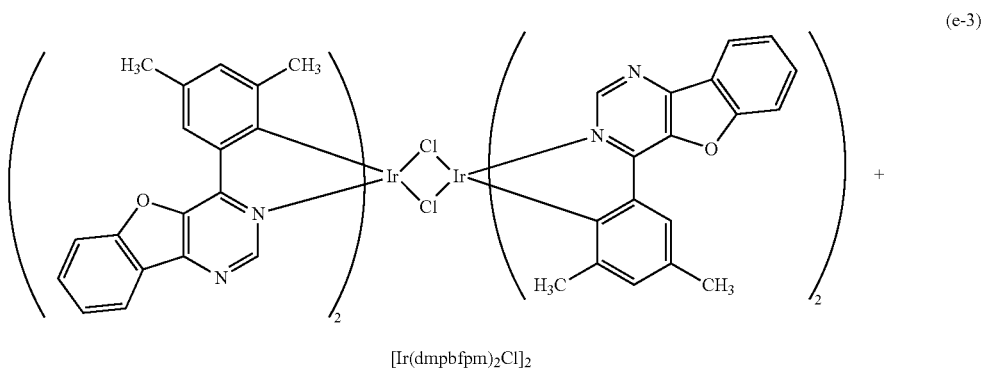

(e-3)

[Ir(dmpbfpm)₂Cl]₂

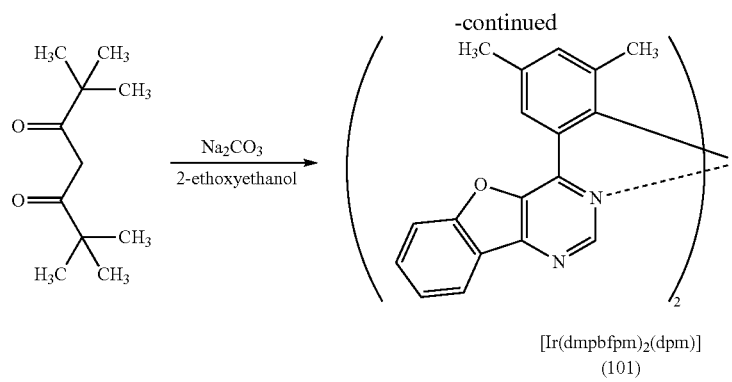

[Ir(dmpbfpm)$_2$(dpm)]
(101)

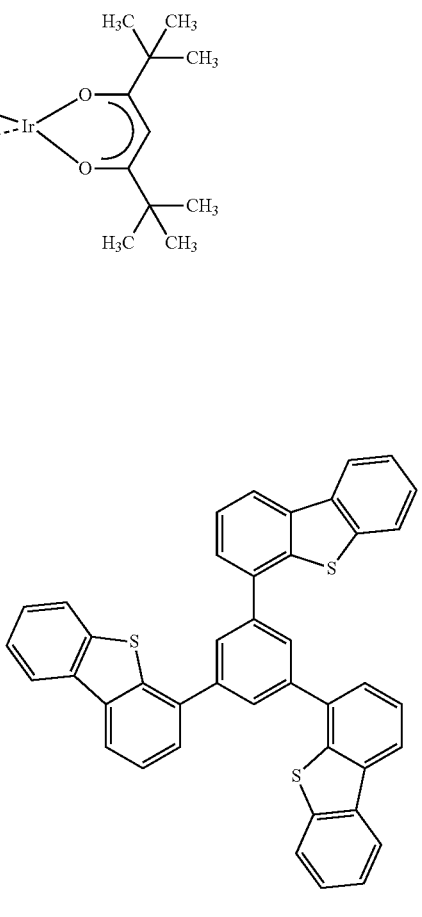

DBT3P-II

Figure 11:
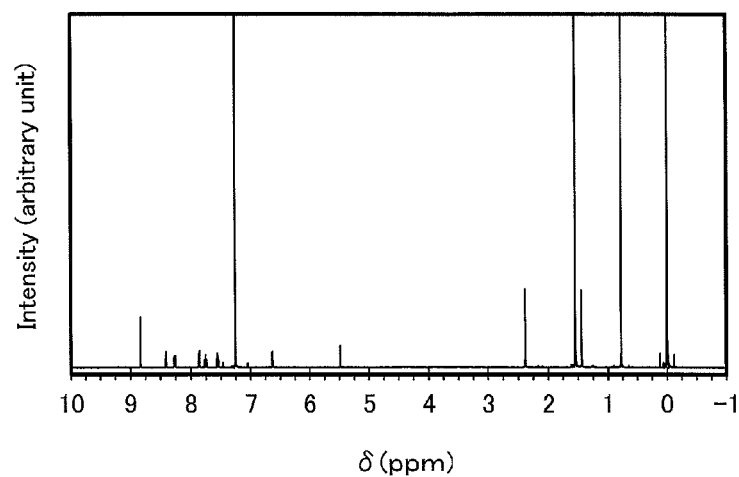
FIG. 11 is a $^1$H NMR chart of Ir(dmpbfpm)$_2$(dpm), which is an organometallic complex according to one embodiment of the present invention.

Note that results of the analysis in which the red powder obtained in Step 3 above was analyzed by nuclear magnetic resonance spectrometry ($^1$H-NMR) are given below. The $^1$H NMR chart is shown in FIG. 11. These results revealed that Ir(dmpbfpm)$_2$(dpm), the organometallic complex according to the present invention which is represented by the above structural formula (101), was obtained in Synthesis Example 2.

$^1$H-NMR. δ (CDCl$_3$): 0.78 (s, 18H), 1.49 (s, 6H), 2.39 (s, 6H), 5.49 (s, 1H), 6.63 (s, 2H), 7.56 (t, 2H), 7.76 (t, 2H), 7.87 (d, 2H), 8.27 (d, 2H), 8.41 (s, 2H), 8.83 (s, 2H).

Figure 12:
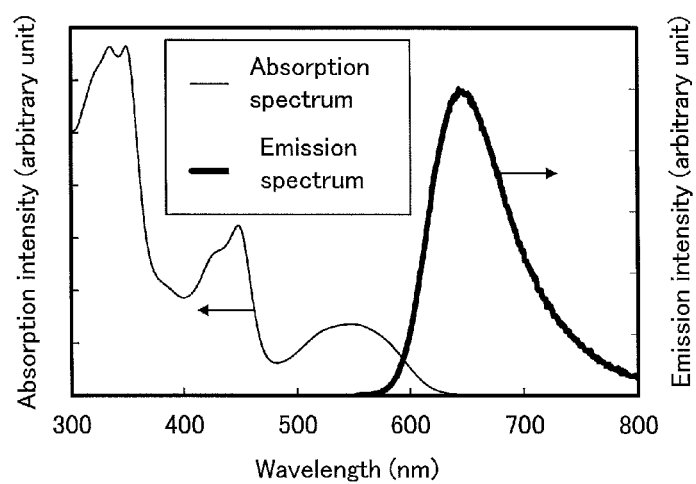
FIG. 12 shows an ultraviolet-visible absorption spectrum and an emission spectrum of Ir(dmpbfpm)$_2$(dpm), which is an organometallic complex according to one embodiment of the present invention, in a dichloromethane solution.

Next, an analysis of Ir(dmpbfpm)$_2$(dpm) was conducted by an ultraviolet-visible (UV) absorption spectrometry. The UV spectrum was measured with an ultraviolet-visible spectrophotometer (V-550, produced by JASCO Corporation) using a dichloromethane solution (0.072 mmol/L) at room temperature. Further, an emission spectrum of Ir(dmpbfpm)$_2$(dpm) was measured. The emission spectrum was measured with a fluorescence spectrophotometer (FS920, produced by Hamamatsu Photonics K.K.) using a degassed dichloromethane solution (0.072 mmol/L) at room temperature. FIG. 12 shows the measurement results. In FIG. 12, the horizontal axis represents wavelength and the vertical axes represent molar absorption coefficient and emission intensity.

As shown in FIG. 12, Ir(dmpbfpm)$_2$(dpm), which is an organometallic complex according to the present invention, has an emission peaks at 643 nm, and red light emission was observed from the dichloromethane solution.

Further, the absolute quantum yield of Ir(dmpbfpm)$_2$(dpm) was measured. After the concentration was adjusted with toluene as a solvent so as to be $1.0 \times 10^{-5}$ mol/L, the absolute quantum yield was measured at room temperature with an absolute PL quantum yield measurement system (C9920-02, produced by Hamamatsu Photonics Corporation). As a result, the absolute quantum yield was 85%, which indicates high emission efficiency.

EXAMPLE 3

Figure 13:
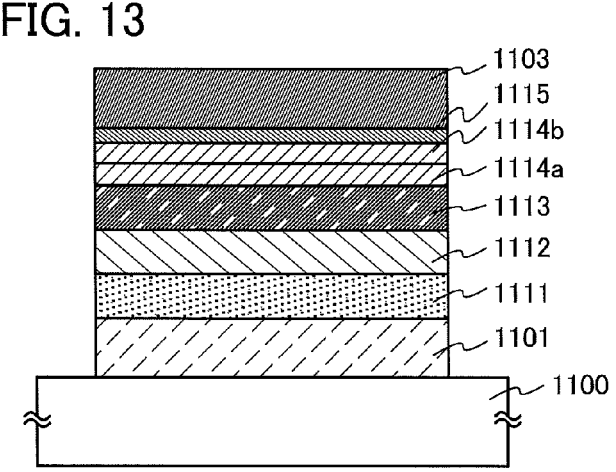
FIG. 13 illustrates a light-emitting element of an example.

In this example, a light-emitting element of one embodiment of the present invention (light-emitting element 1) is described with reference to FIG. 13. Chemical formulae of materials used in this example are shown below.

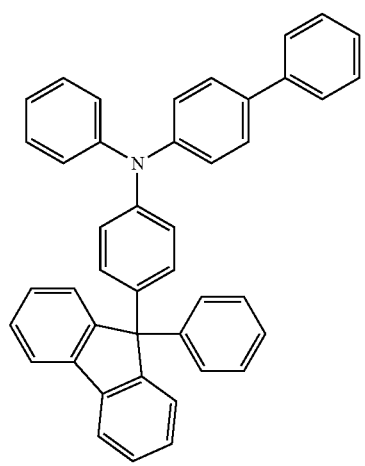

BPAFLP

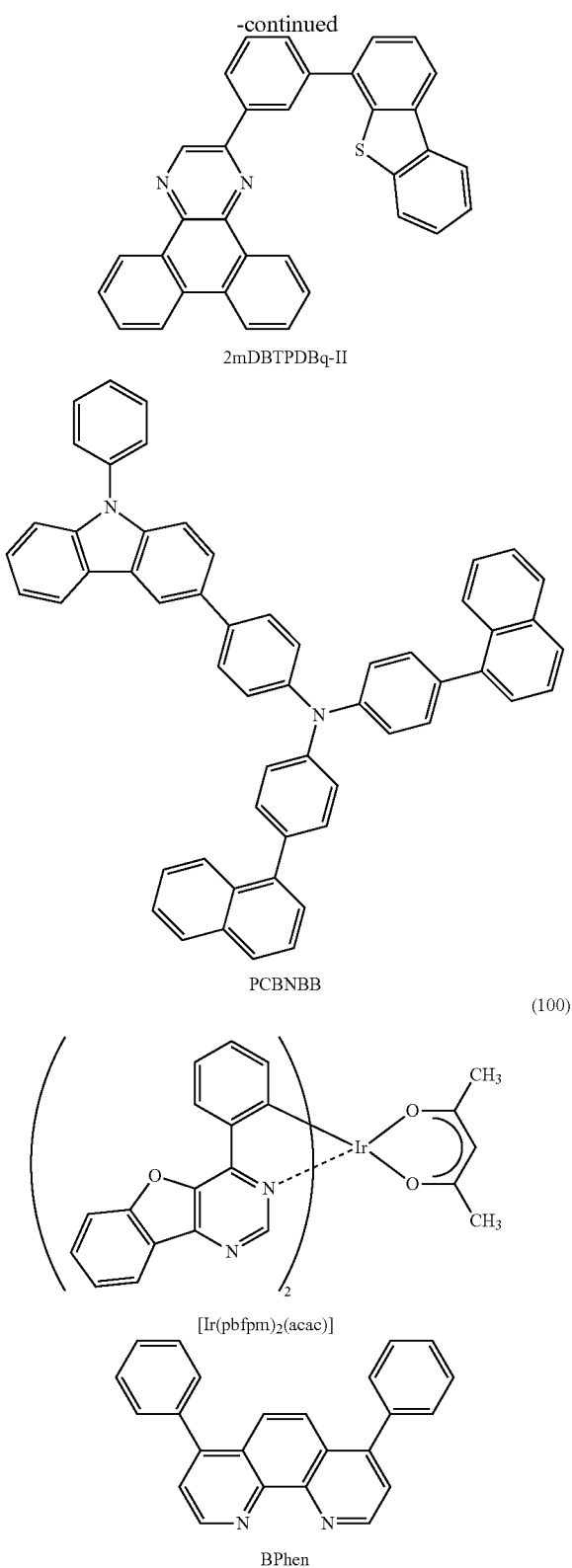

(100)

A method of fabricating the light-emitting element 1 of this example is described below.

(Light-Emitting Element 1)

First, an indium oxide-tin oxide compound containing silicon or silicon oxide (ITO-SiO$_2$, hereinafter abbreviated to ITSO) was deposited over a substrate 1100 by a sputtering method, so that a first electrode 1101 was formed. Note that the composition of the target used is as follows: In$_2$O$_3$:SnO$_2$:SiO$_2$=85:10:5 (wt %). The thickness of the first electrode 1101 was set to 110 nm and the electrode area was set to 2 mm×2 mm. Here, the first electrode 1101 is an electrode that functions as an anode of the light-emitting element.

Next, as pretreatment for forming the light-emitting element over the substrate 1100, the surface of the substrate was washed with water, baked at 200° C. for 1 hour, and subjected to UV ozone treatment for 370 seconds.

After that, the substrate was transferred into a vacuum evaporation apparatus where the pressure was reduced to about 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa. Then, 4,4',4''-(benzene-1,3,5-triyl)tri(dibenzothiophene) (abbreviation: DBT3P-II) and molybdenum oxide were co-evaporated to form a hole-injection layer 1111 over the first electrode 1101. The thickness of the hole-injection layer 1111 was set to 40 nm, and the weight ratio of DBT3P-II to molybdenum oxide was adjusted to 4:2 (=DBT3P-II:molybdenum oxide).

Next, over the hole-injection layer 1111, a film of 4-phenyl-4'-(9-phenylfluoren-9-yl)triphenylamine (abbreviation: BPAFLP) was formed to a thickness of 20 nm; so that a hole-transport layer 1112 was formed.

Further, 2-[3-(dibenzothiophen-4-yl)phenyl]dibenzo[f,h]quinoxaline (abbreviation: 2mDBTPDBq-II), 4,4'-di(1-naphthyl)-4''-(9-phenyl-9H-carbazol-3-yl)triphenylamine (abbreviation: PCBNBB), and bis[2-(benzofuro[3,2-d]pyrimidin-4-yl-κN3)phenyl-κC](2,4-pentanedionato-κ$^2$O,O)iridium(III) (abbreviation: Ir(pbfpm)$_2$(acac)) synthesized in Example 1 were co-evaporated to form a light-emitting layer 1113 over the hole-transport layer 1112. Here, the weight ratio of 2mDBTPDBq-II to PCBNBB and Ir(pbfpm)$_2$(acac) was adjusted to 0.8:0.2:0.025 (=2mDBTPDBq-II:PCBNBB:Ir(pbfpm)$_2$(acac)). The thickness of the light-emitting layer 1113 was set to 40 nm.

Note that Ir(pbfpm)$_2$(acac) is an organometallic complex of one embodiment of the present invention and was used as a guest material (dopant) in the light-emitting layer 1113.

Next, over the light-emitting layer 1113, a film of 2mDBTPDBq-II was formed to a thickness of 10 nm to farm a first electron-transport layer 1114a.

After that, over the first electron-transport layer 1114a, a bathophenanthroline (abbreviation: BPhen) film was formed to a thickness of 20 nm, so that a second electron-transport layer 1114b was formed.

Further, over the second electron-transport layer 1114b, a lithium fluoride (LiF) film was formed to a thickness of 1 nm by evaporation, whereby an electron-injection layer 1115 was formed.

Lastly, an aluminum film was formed to a thickness of 200 nm by evaporation as a second electrode 1103 functioning as a cathode. Thus, the light-emitting element 1 of this example was fabricated.

Table 1 shows an element structure of the light-emitting element 1 formed as described above.

TABLE 1

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 1 | ITSO 110 nm | DBT3P-II:MoOx (= 4:2) 40 nm | BPAFLP 20 nm | ※1 | 2mDBTPDHq-II 10 nm | BPhen 20 nm | LiF 1 nm | Al 200 nm |

※1:2mDBTPDBq-II:PCBNBB:Ir(pbfpm)$_2$(acac) = (0.8:0.2:0.025) 40 nm

Then, in a glove box containing a nitrogen atmosphere, the light-emitting element 1 was sealed so as not to be exposed to the air (specifically, a sealant was applied onto an outer edge of the element and heat treatment was performed at 80° C. for 1 hour at the time of sealing). After that, operation characteristics of the light-emitting element 1 were measured. Note that the measurements were carried out at room temperature (in an atmosphere kept at 25° C.).

Figure 14:
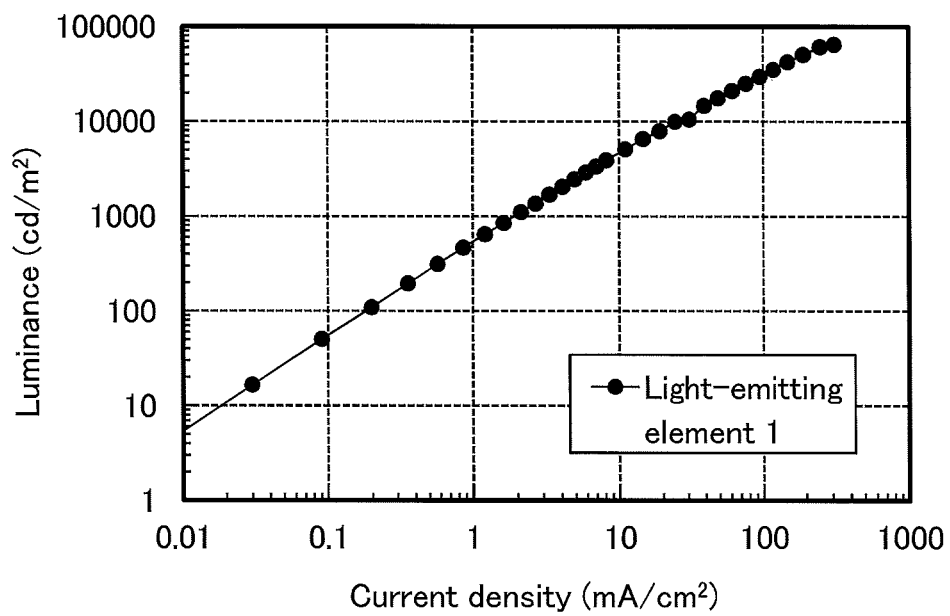
FIG. 14 shows luminance versus current density characteristics of a light-emitting element 1.
Figure 15:
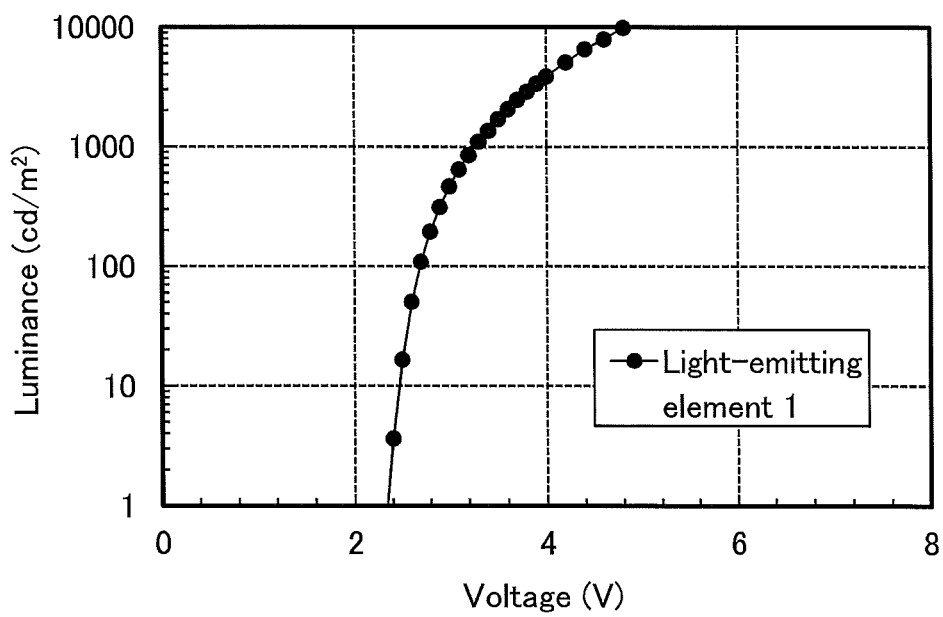
FIG. 15 shows luminance versus voltage characteristics of the light-emitting element 1.
Figure 16:
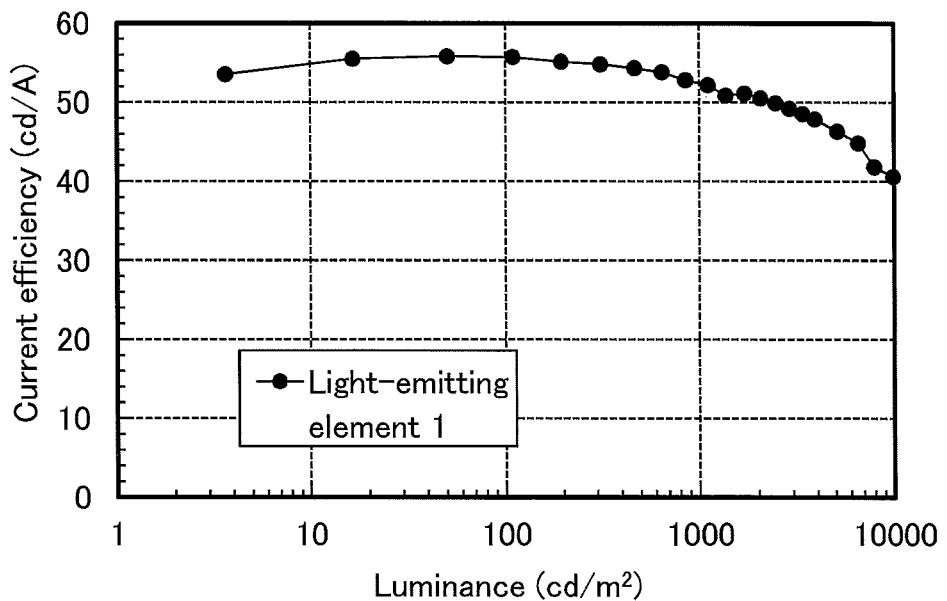
FIG. 16 shows current efficiency versus luminance characteristics of the light-emitting element 1.
Figure 17:
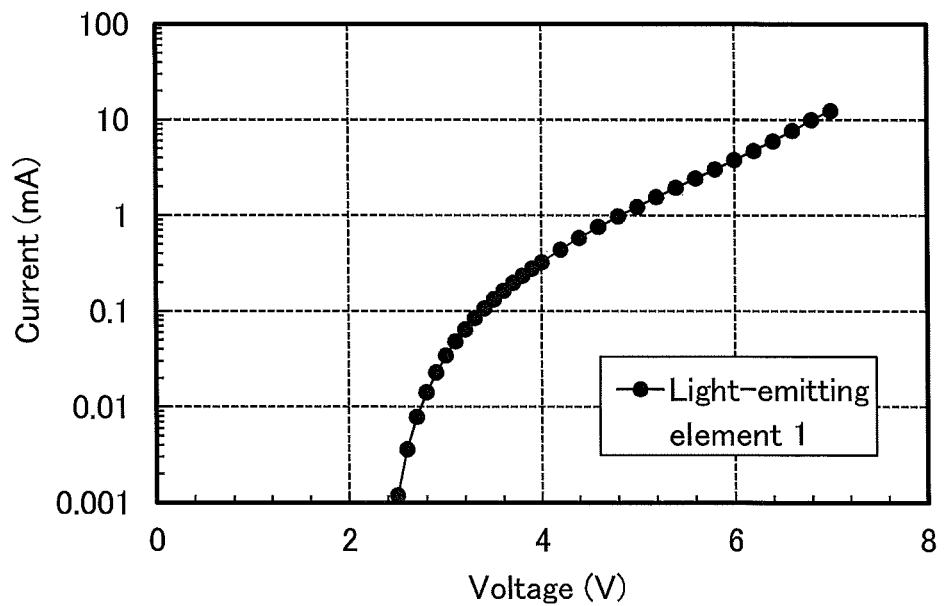
FIG. 17 shows current versus voltage characteristics of the light-emitting element 1.

FIG. 14 shows luminance versus current density characteristics of the light-emitting element 1. In FIG. 14, the horizontal axis represents current density (mA/cm$^2$) and the vertical axis represents luminance (cd/m$^2$). Further, FIG. 15 shows luminance versus voltage characteristics of the light-emitting element 1. In FIG. 15, the horizontal axis represents voltage (V) and the vertical axis represents luminance (cd/m$^2$). In addition, FIG. 16 shows current efficiency versus luminance characteristics of the light-emitting element 1. In FIG. 16, the horizontal axis represents luminance (cd/m$^2$) and the vertical axis represents current efficiency (cd/A). In addition, FIG. 17 shows current versus voltage characteristics of the light-emitting element 1. In FIG. 17, the horizontal axis represents voltage (V) and the vertical axis represents current (mA).

FIG. 14 and FIG. 16 show that the light-emitting element 1 is a light-emitting element with high efficiency. Further, FIG. 14, FIG. 15, and FIG. 17 show that the light-emitting element 1 is a light-emitting element with low drive voltage and low power consumption.

Next, Table 2 shows the voltage (V), current density (mA/cm$^2$), CIE chromaticity coordinates (x, y), luminance (cd/m$^2$), current efficiency (cd/A), and external quantum efficiency (%) of the light-emitting element 1 at a luminance of 1104 cd/m$^2$.

TABLE 2

| | Voltage (V) | Current density (mA/cm$^2$) | CIE chromaticity coordinates | | Luminance (cd/m$^2$) | Current efficiency (cd/A) | External quantum efficiency (%) |
|---|---|---|---|---|---|---|---|
| | | | x | y | | | |
| Light-emitting element 1 | 3.3 | 2.1 | 0.60 | 0.40 | 1104 | 52 | 26 |

Figure 18:
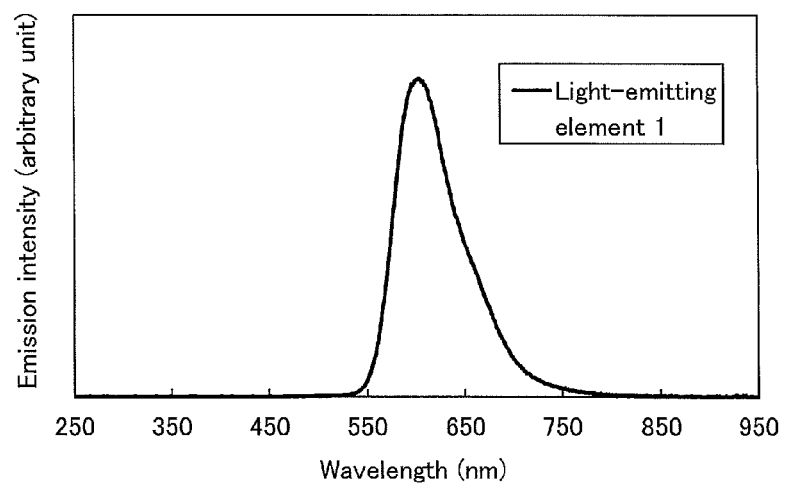
FIG. 18 shows an emission spectrum of the light-emitting element 1.

FIG. 18 shows an emission spectrum when a current was supplied at a current density of 2.5 mA/cm$^2$ to the light-emitting element 1. As shown in FIG. 18, the emission spectrum of the light-emitting element 1 has a peak at 603 nm.

In addition, as shown in Table 2, the CIE chromaticity coordinates of the light-emitting element 1 were (x, y)=(0.60, 0.40) at a luminance of 1104 cd/m$^2$. These results show that light originating from the dopant was obtained.

The above demonstrates that the light-emitting element 1 in which Ir(pbfpm)$_2$(acac), which is an organometallic complex of one embodiment of the present invention, is used for the light-emitting layer can efficiently emit light in the red wavelength region. This means that Ir(pbfpm)$_2$(acac) can be suitably used as a guest material which emits light in the red wavelength region.

Next, the light-emitting element 1 was subjected to reliability tests. Results of the reliability tests were shown in FIG. 19.

Figure 19:
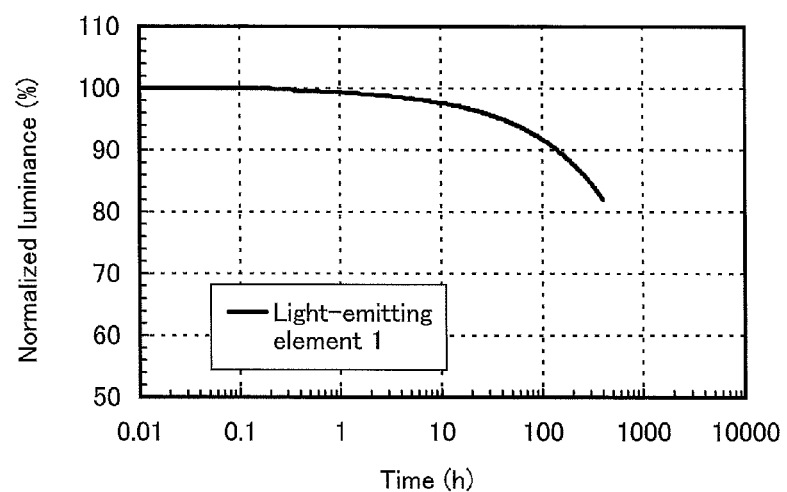
FIG. 19 shows normalized luminance versus driving time characteristics of the light-emitting element 1.

In the reliability tests, the light-emitting element 1 was driven under the conditions where the initial luminance was 5000 cd/m$^2$ and the current density was constant. The results are shown in FIG. 19. The horizontal axis represents driving time (h) of the element and the vertical axis represents normalized luminance (%) on the assumption that the initial luminance is 100%. FIG. 19 shows that the normalized luminance of the light-emitting element 1 after 400 hours is 82%.

FIG. 19 shows that the light-emitting element 1 has a long lifetime.

The above results show that the light-emitting element 1 in which Ir(pbfpm)$_2$(acac), which is an organometallic complex according to the present invention, is used for the light-emitting layer has high efficiency, low driving voltage, low power consumption, and a long lifetime.

EXAMPLE 4

In this example, a light-emitting element of one embodiment of the present invention (light-emitting element 2) is described with reference to FIG. 13. Chemical formulae of materials used in this example are shown below.

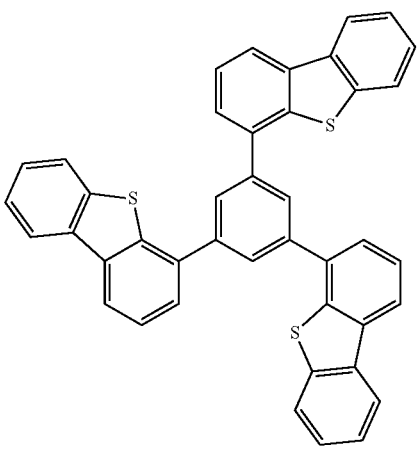

DBT3P-II

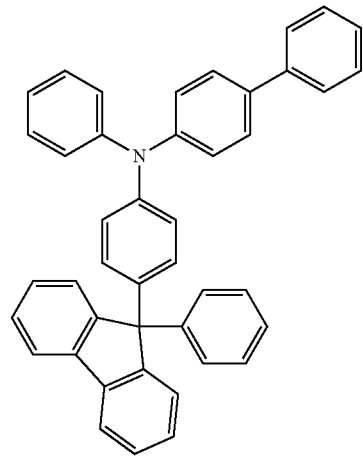

BPAFLP

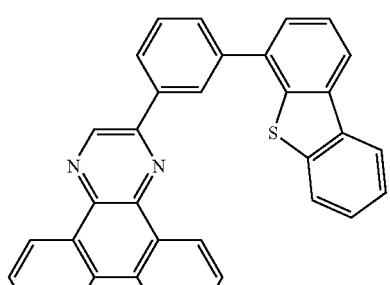

2mDBTPDBq-II

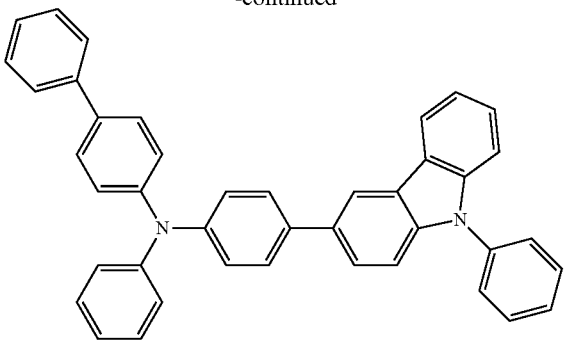

PCBA1BP

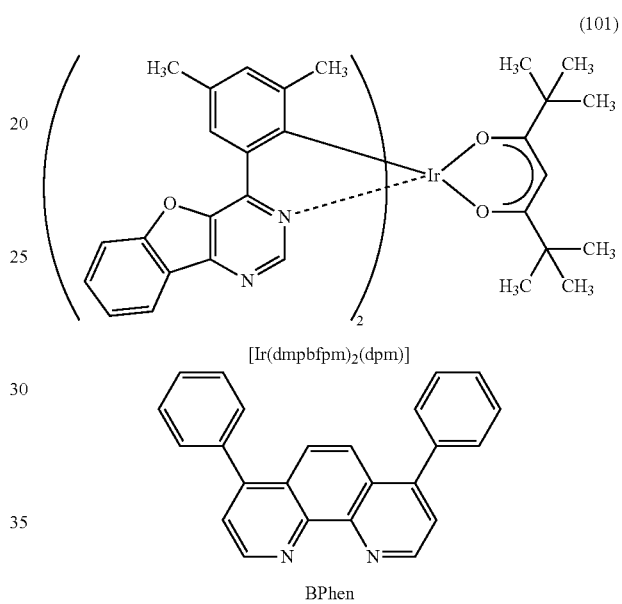

[Ir(dmpbfpm)$_2$(dpm)] (101)

BPhen

A method of fabricating the light-emitting element 2 of this example is described below.

(Light-Emitting Element 2)

First, an indium oxide-tin oxide compound containing silicon or silicon oxide (ITSO) was deposited over the substrate 1100 by a sputtering method, so that the first electrode 1101 was formed. Note that the composition of the target used was as follows: In$_2$O$_3$:SnO$_2$:SiO$_2$=85:10:5 (wt %). The thickness of the first electrode 1101 was set to 110 nm and the electrode area was set to 2 mm×2 mm. Here, the first electrode 1101 is an electrode that functions as an anode of the light-emitting element.

Next, as pretreatment for forming the light-emitting element over the substrate 1100, the surface of the substrate was washed with water, baked at 200° C. for 1 hour, and subjected to UV ozone treatment for 370 seconds.

After that, the substrate was transferred into a vacuum evaporation apparatus where the pressure was reduced to about 10$^{-4}$ Pa, and subjected to vacuum baking at 170° C. for 30 minutes in a heating chamber of the vacuum evaporation apparatus, and then the substrate 1100 was cooled down for about 30 minutes.

Next, the substrate 1100 provided with the first electrode 1101 was fixed to a substrate holder in the vacuum evaporation apparatus so that a surface on which the first electrode 1101 was provided faced downward. The pressure in the vacuum evaporation apparatus was reduced to about 10$^{-4}$ Pa.

Then, DBT3P-II and molybdenum oxide were co-evaporated to form the hole-injection layer 1111 over the first electrode 1101. The thickness of the hole-injection layer 1111 was set to 30 nm, and the weight ratio of DBT3P-II to molybdenum oxide was adjusted to 4:2 (=DBT3P-II:molybdenum oxide).

Next, BPAFLP was formed to a thickness of 20 nm over the hole-injection layer 1111, whereby the hole-transport layer 1112 was formed.

Further, 2mDBTPDBq-II, 4-phenyl-4'-(9-phenyl-9H-carbazol-3-yl)triphenylamine (abbreviation: PCBA1BP), and bis[2-(benzofuro[3,2-d]pyrimidin-4-yl-κN3)-4,6-dimethylphenyl-κC](2,2',6,6'-tetramethyl-3,5-heptanedionato-κ$^2$O, O')iridium(III) (abbreviation: Ir(dmpbfpm)$_2$(dpm)) synthesized in Example 2 were co-evaporated to form the light-emitting layer 1113 over the hole-transport layer 1112. Here, the weight ratio of 2mDBTPDBq-II to PCBA1BP and Ir(dmpbfpm)$_2$(dpm) was adjusted to 0.8:0.2:0.025 (=2mDBTPDBq-II:PCBA1BP:Ir(dmpbfpm)$_2$(dpm)). The thickness of the light-emitting layer 1113 was set to 40 nm.

Note that Ir(dmpbfpm)$_2$(dpm) is an organometallic complex of one embodiment of the present invention and was used as a guest material (dopant) in the light-emitting layer 1113.

Next, over the light-emitting layer 1113, a film of 2mDBT-PDBq-II was formed to a thickness of 20 nm to form the first electron-transport layer 1114*a*.

After that, over the first electron-transport layer 1114*a*, a BPhen film was formed to a thickness of 20 nm, so that the second electron-transport layer 1114*b* was formed.

Further, over the second electron-transport layer 1114*b*, a lithium fluoride (LiF) film was formed to a thickness of 1 nm by evaporation, whereby the electron-injection layer 1115 was formed.

Lastly, an aluminum film was formed to a thickness of 200 nm by evaporation as the second electrode 1103 functioning as a cathode. Thus, the light-emitting element 2 of this example was fabricated.

Table 3 shows an element structure of the light-emitting element 2 formed as described above.

TABLE 3

| | First electrode | Hole-injection layer | Hole-transport layer | Light-emitting layer | First electron-transport layer | Second electron-transport layer | Electron-injection layer | Second electrode |
|---|---|---|---|---|---|---|---|---|
| Light-emitting element 2 | ITSO 110 nm | DBT3P-II:MoOx (= 4:2) 30 nm | BPAFLP 20 nm | ※1 | 2mDBTPDBq-II 20 nm | BPhen 20 nm | LiF 1 nm | Al 200 nm |

※1:2mDBTPDBq-II:PCBA1BP:Ir(dmpbfpm)$_2$(dpm) = (0.8:0.2:0.025) 40 nm

Then, in a glove box containing a nitrogen atmosphere, the light-emitting element 2 was sealed so as not to be exposed to the air (specifically, a sealant was applied onto an outer edge of the element and heat treatment was performed at 80° C. for 1 hour at the time of sealing). After that, operation characteristics of the light-emitting element 2 were measured. Note that the measurements were carried out at room temperature (in an atmosphere kept at 25° C.).

Figure 20:
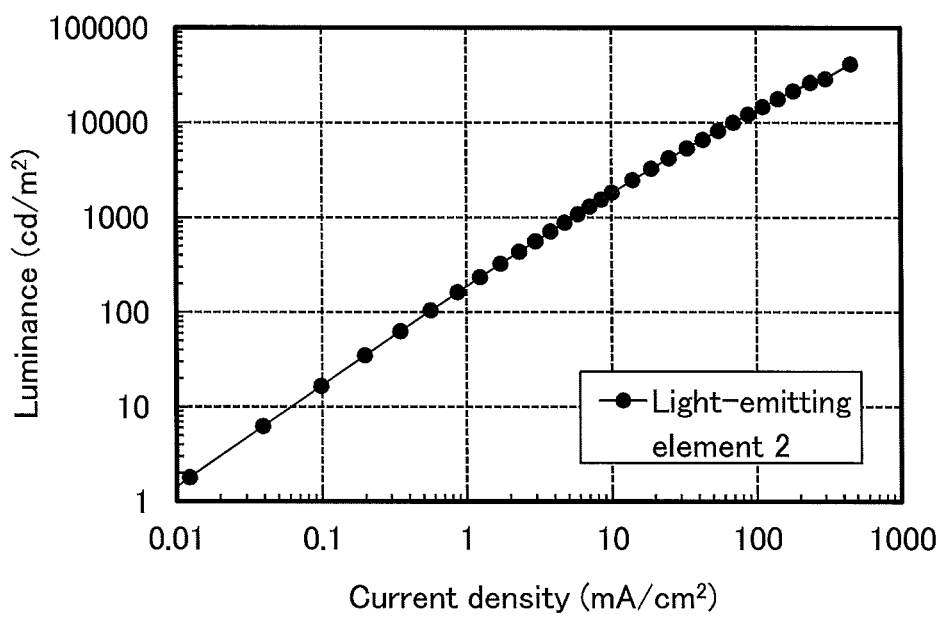
FIG. 20 shows luminance versus current density characteristics of a light-emitting element 2.
Figure 21:
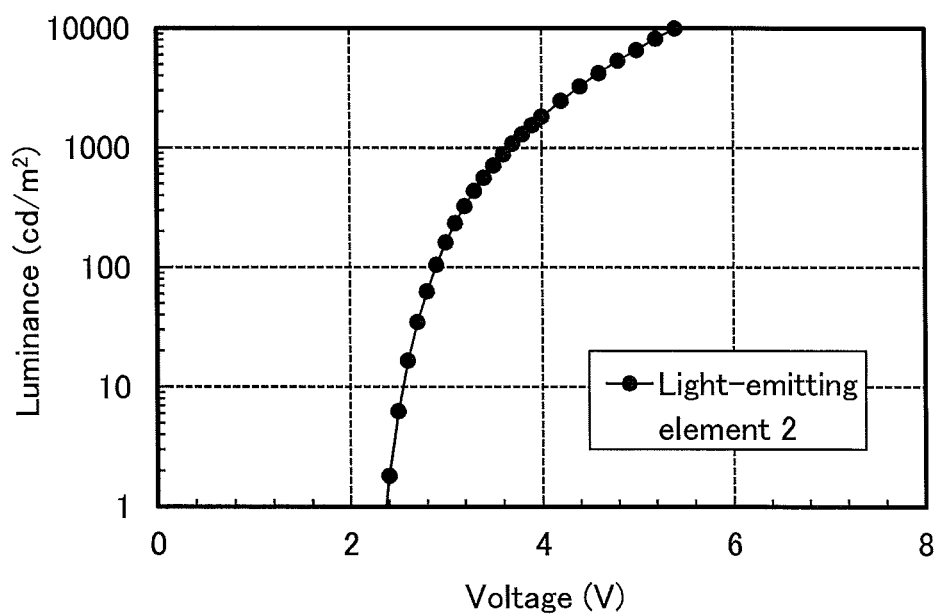
FIG. 21 shows luminance versus voltage characteristics of the light-emitting element 2.
Figure 22:
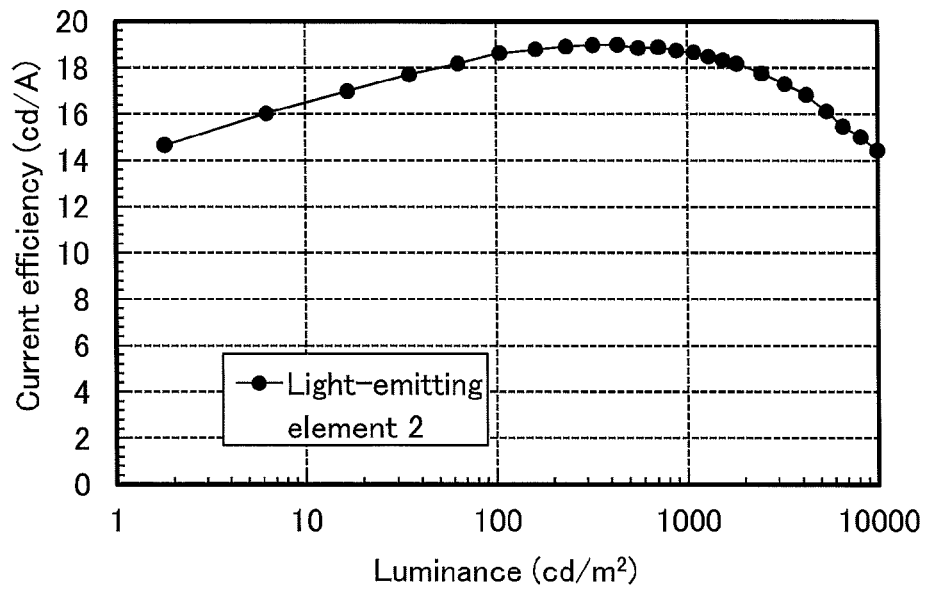
FIG. 22 shows current efficiency versus luminance characteristics of the light-emitting element 2.
Figure 23:
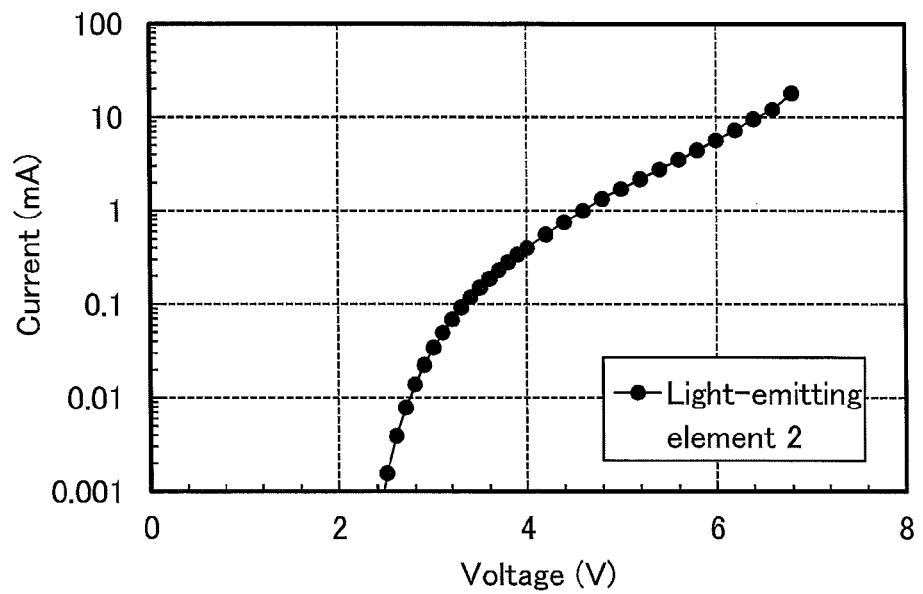
FIG. 23 shows current versus voltage characteristics of the light-emitting element 2.

FIG. 20 shows luminance versus current density characteristics of the light-emitting element 2. In FIG. 20, the horizontal axis represents current density (mA/cm$^2$) and the vertical axis represents luminance (cd/m$^2$). Further, FIG. 21 shows luminance versus voltage characteristics of the light-emitting element 2. In FIG. 21, the horizontal axis represents voltage (V) and the vertical axis represents luminance (cd/m$^2$). In addition, FIG. 22 shows current efficiency versus luminance characteristics of the light-emitting element 2. In FIG. 22, the horizontal axis represents luminance (cd/m$^2$) and the vertical axis represents current efficiency (cd/A). In addition, FIG. 23 shows current versus voltage characteristics of the light-emitting element 2. In FIG. 23, the horizontal axis represents voltage (V) and the vertical axis represents current (mA).

FIG. 20 and FIG. 22 show that the light-emitting element 2 is a light-emitting element with high efficiency. Further, FIG. 20, FIG. 21, and FIG. 23 show that the light-emitting element 2 is a light-emitting element with low drive voltage and low power consumption.

Next, Table 4 shows the voltage (V), current density (mA/cm$^2$), CIE chromaticity coordinates (x, y), luminance (cd/m$^2$), current efficiency (cd/A), and external quantum efficiency (%) of the light-emitting element 2 at a luminance of 1081 cd/m$^2$.

TABLE 4

| | Voltage | Current density | CIE chromaticity coordinates | | Luminance | Current efficiency | External quantum efficiency |
|---|---|---|---|---|---|---|---|
| | (V) | (mA/cm$^2$) | x | y | (cd/m$^2$) | (cd/A) | % |
| Light-emitting element 2 | 3.7 | 5.8 | 0.67 | 0.33 | 1081 | 19 | 20 |

Figure 24:
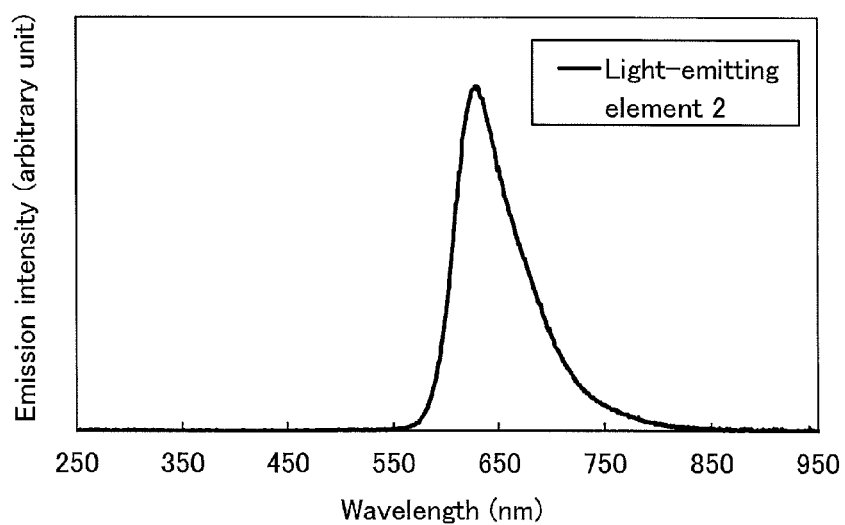
FIG. 24 shows an emission spectrum of the light-emitting element 2.

FIG. 24 shows an emission spectrum when a current was supplied at a current density of 2.5 mA/cm$^2$ to the light-emitting element 2. As shown in FIG. 24, the emission spectrum of the light-emitting element 2 has a peak at 630 nm.

In addition, as shown in Table 4, the CIE chromaticity coordinates of the light-emitting element 2 were (x, y)=(0.67, 0.33) at a luminance of 1081 cd/m$^2$. These results show that light originating from the dopant was obtained.

The above demonstrates that the light-emitting element 2 in which Ir(dmpbfpm)$_2$(dpm), which is an organometallic complex of one embodiment of the present invention, is used for the light-emitting layer can efficiently emit light in the red wavelength region. This means that Ir(dmpbfpm)$_2$(dpm) can be suitably used as a guest material which emits light in the red wavelength region.

Next, the light-emitting element 2 was subjected to reliability tests. Results of the reliability tests were shown in FIG. 25.

Figure 25:
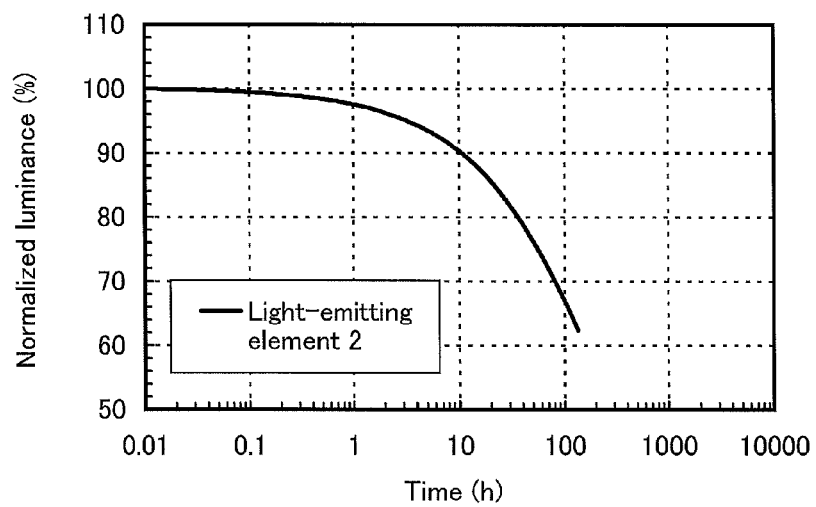
FIG. 25 shows normalized luminance versus driving time characteristics of the light-emitting element 2.

In the reliability tests, the light-emitting element 2 was driven under the conditions where the initial luminance was 5000 cd/m² and the current density was constant. The results are shown in FIG. 25. The horizontal axis represents driving time (h) of the element and the vertical axis represents normalized luminance (%) on the assumption that the initial luminance is 100%. FIG. 25 shows that the normalized luminance of the light-emitting element 2 after 140 hours is 62%.

FIG. 25 shows that the light-emitting element 2 is a light-emitting element with a long lifetime.

The above results show that the light-emitting element 2 in which Ir(dmpbfpm)₂(dpm), which is an organometallic complex of one embodiment of the present invention, is used for the light-emitting layer is a light-emitting element having high efficiency, low drive voltage, low power consumption, and a long lifetime.

This application is based on Japanese Patent Application serial No. 2012-126045 filed with the Japan Patent Office on Jun. 1, 2012, the entire contents of which are hereby incorporated by reference.

What is claimed is:

1. A light-emitting element comprising an organometallic complex comprising a benzofuropyrimidine derivative,
   wherein the benzofuropyrimidine derivative is coordinated to a metal, and
   wherein the benzofuropyrimidine derivative has an aryl group at a 4-position.

2. The light-emitting element according to claim 1,
   wherein nitrogen at a 3-position of the benzofuropyrimidine derivative is coordinated to the metal, and
   wherein the aryl group is bonded to the metal.

3. The light-emitting element according to claim 1, wherein the metal is a Group 9 element or a Group 10 element.

4. The light-emitting element according to claim 1, wherein the metal is iridium.

5. A display device comprising the light-emitting element according to claim 1.

6. An electronic device comprising the light-emitting element according to claim 1.

7. A lighting device comprising the light-emitting element according to claim 1.

8. An organometallic complex comprising a structure represented by a general formula (G1),

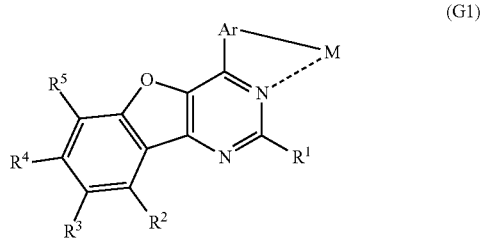

(G1)

wherein R¹ represents hydrogen or a substituted or unsubstituted alkyl group having 1 to 6 carbon atoms,
wherein R² to R⁵ separately represent any of hydrogen, a substituted or unsubstituted alkyl group having 1 to 6 carbon atoms, a substituted or unsubstituted monocyclic saturated hydrocarbon having 5 to 7 carbon atoms, a substituted or unsubstituted polycyclic saturated hydrocarbon having 7 to 10 carbon atoms, and a substituted or unsubstituted aryl group having 6 to 13 carbon atoms,
wherein Ar represents a substituted or unsubstituted arylene group having 6 to 10 carbon atoms, and
wherein M represents a Group 9 element or a Group 10 element.

9. The organometallic complex according to claim 8,
wherein the structure is represented by a general formula (G2), and

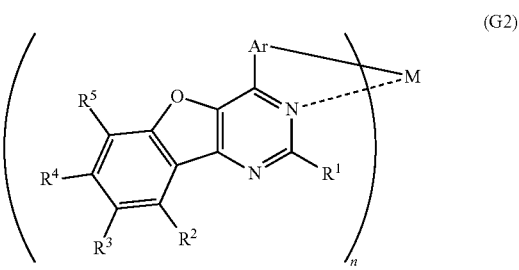

(G2)

wherein n is 3 when the M is the Group 9 element, or n is 2 when the M is the Group 10 element.

10. The organometallic complex according to claim 8, wherein the structure is represented by a general formula (G3),

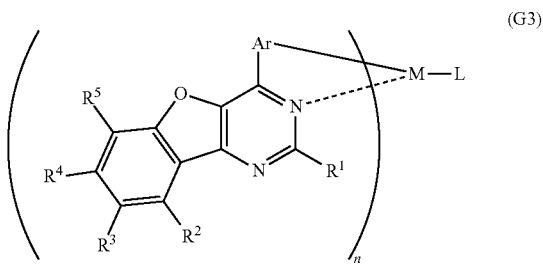

(G3)

wherein n is 2 when the M is the Group 9 element, or n is 1 when the M is the Group 10 element, and wherein L represents a monoanionic ligand.

11. The organometallic complex according to claim 10, wherein the monoanionic ligand is represented by any of general formulae (L1) to (L7),

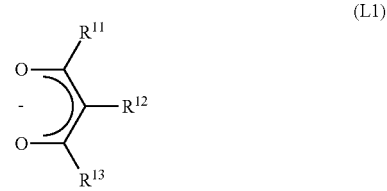

(L1)

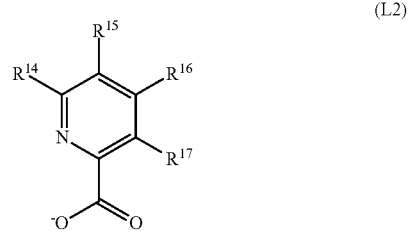

(L2)

-continued

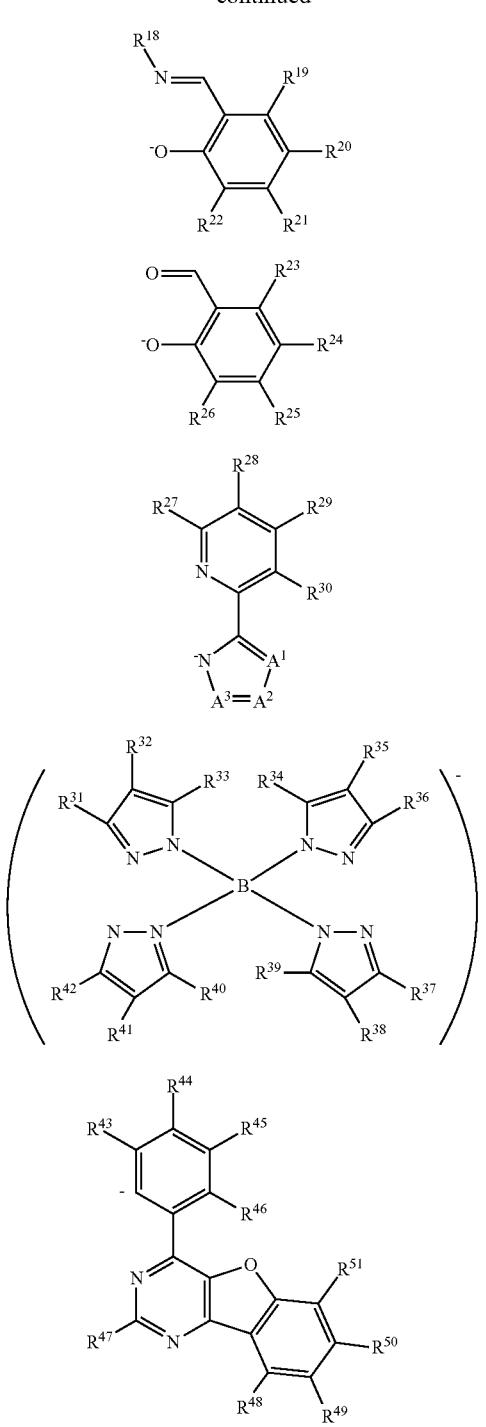

wherein R$^{11}$ to R$^{51}$ separately represent any of hydrogen, a substituted or unsubstituted alkyl group having 1 to 6 carbon atoms, a halogen group, a vinyl group, a substituted or unsubstituted haloalkyl group having 1 to 6 carbon atoms, a substituted or unsubstituted alkoxy group having 1 to 6 carbon atoms, and a substituted or unsubstituted alkylthio group having 1 to 6 carbon atoms, and wherein A$^1$ to A$^3$ separately represent any of nitrogen, sp$^2$ hybridized carbon bonded to hydrogen, and sp$^2$ hybridized carbon bonded to any of an alkyl group having 1 to 6 carbon atoms, a halogen group, a haloalkyl group having 1 to 6 carbon atoms, and a phenyl group.

12. The organometallic complex according to claim 8, wherein the organometallic complex is represented by a structural formula (100),

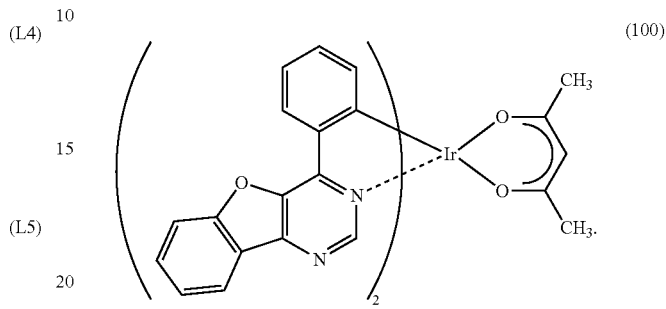

13. The organometallic complex according to claim 8, wherein the organometallic complex is represented by a structural formula (101),

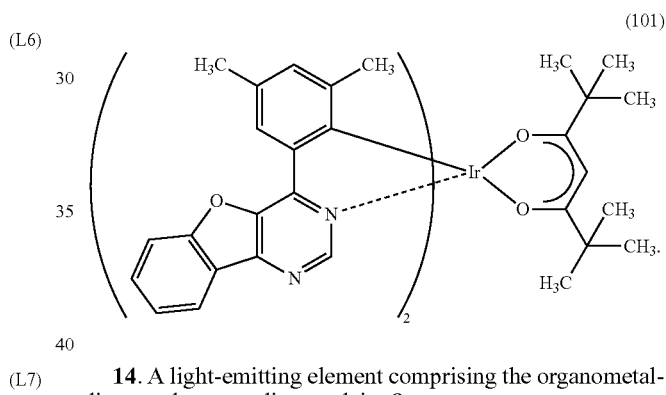

14. A light-emitting element comprising the organometallic complex according to claim 8.

15. A display device comprising the light-emitting element according to claim 14.

16. An electronic device comprising the light-emitting element according to claim 14.

17. A lighting device comprising the light-emitting element according to claim 14.

18. An organometallic complex comprising a benzofuropyrimidine derivative,
wherein the benzofuropyrimidine derivative is coordinated to a metal, and
wherein the benzofuropyrimidine derivative has an aryl group at a 4-position.

19. The organometallic complex according to claim 18,
wherein nitrogen at a 3-position of the benzofuropyrimidine derivative is coordinated to the metal, and
wherein the aryl group is bonded to the metal.

20. The organometallic complex according to claim 18, wherein the metal is a Group 9 element or a Group 10 element.

21. The organometallic complex according to claim 18, wherein the metal is iridium.

* * * * *

UNITED STATES PATENT AND TRADEMARK OFFICE
CERTIFICATE OF CORRECTION

| | | |
|---|---|---|
| PATENT NO. | : 8,921,549 B2 | Page 1 of 1 |
| APPLICATION NO. | : 13/905783 | |
| DATED | : December 30, 2014 | |
| INVENTOR(S) | : Hideko Inoue et al. | |

It is certified that error appears in the above-identified patent and that said Letters Patent is hereby corrected as shown below:

In the Specification:

Column 28, Line 42; Change "Ir(dlnpm)$_2$" to --Ir(d1npm)$_2$--.

Column 28, Line 45; Change "(2,3,5-triPhenylpyrazinato)" to --(2,3,5-triphenylpyrazinato)--.

Column 29, Line 3; Change "berizothiazolato]" to --benzothiazolato]--.

Column 29, Line 29; Change "115; a" to --115, a--.

Column 33, Line 65; Change "team" to --term--.

Column 34, Line 35; Change "454E" to --454G,--.

Column 34, Line 49; Change "450G" to --450G,--.

Column 34, Line 58; Change "450G" to --450G,--.

Column 35, Line 57; Change "450G and" to --450G, and--.

Column 36, Line 36; Change "450G light" to --450G, light--.

Column 36, Line 57; Change "454G respectively." to --454G, respectively.--.

Column 37, Line 28; Change "ofR, G and B." to --of R, G, and B.--.

Column 38, Line 36; Change "foamed" to --formed--.

Column 38, Line 59; Change "(R, and B)" to --(R, G, and B)--.

Column 44, Line 21; Change "(IrCl$_3$.H$_2$0)" to --(IrCl$_3$·H$_2$0)--.

Column 45, Line 16; Change "ethanol The" to --ethanol. The--.

Column 54, Line 34; Change "of 20 nm; so" to --of 20 nm, so--.

Column 54, Lines 40 to 41; Change "pentanedionato-$\kappa^2$O,O)iridium(111)" to --pentanedionato-$\kappa^2$O,O')iridium(III)--.

Column 54, Line 52; Change "farm" to --form--.

Column 56, Line 42; Change "603 nm" to --603 nm.--.

Signed and Sealed this
Ninth Day of June, 2015

Michelle K. Lee
*Director of the United States Patent and Trademark Office*